US009545216B2

(12) United States Patent
D'Angelo et al.

(10) Patent No.: US 9,545,216 B2
(45) Date of Patent: Jan. 17, 2017

(54) CATHETER BALLOON METHODS AND APPARATUS EMPLOYING SENSING ELEMENTS

(75) Inventors: Robert D'Angelo, Woodbridge, CT (US); Bassel de Graff, San Juan (TT); Kevin Dowling, Westford, MA (US); Roozbeh Ghaffari, Cambridge, MA (US); Lauren Klinker, Somerville, MA (US); Stephen P. Lee, Cambridge, MA (US); Cliff Liu, Randolph, MA (US); Yung-Yu Hsu, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 900 days.

(21) Appl. No.: 13/568,022

(22) Filed: Aug. 6, 2012

(65) Prior Publication Data

US 2013/0150693 A1    Jun. 13, 2013

Related U.S. Application Data

(60) Provisional application No. 61/515,713, filed on Aug. 5, 2011, provisional application No. 61/526,516, filed
(Continued)

(51) Int. Cl.
*A61B 18/18*        (2006.01)
*A61B 5/053*        (2006.01)
(Continued)

(52) U.S. Cl.
CPC .............. *A61B 5/0538* (2013.01); *A61B 5/036* (2013.01); *A61B 5/0422* (2013.01);
(Continued)

(58) Field of Classification Search
CPC ................... A61B 18/1492; A61B 2018/0022; A61B 2018/00214; A61B 2018/00577; A61B 2018/0016; A61B 5/0422; A61B 18/02; A61B 18/24; A61B 2018/00285; A61B 2018/00267; A61B 2018/00797; A61B 2018/1861; A61B 5/0538; A61B 2562/01
(Continued)

(56) References Cited

U.S. PATENT DOCUMENTS 3,716,861 A    2/1973 Root
3,805,427 A    4/1974 Epstein
(Continued)

FOREIGN PATENT DOCUMENTS

JP          10-500333         1/1998
WO    WO 2005/122285 A2    12/2005
(Continued)

OTHER PUBLICATIONS

Demura et al., "Immobilization of Glucose Oxidase with *Bombyx Mori* Silk Fibroin by Only Stretching Treatment and its Application to Glucose Sensor," Biotechnology and Bioengineering, vol. 33, 598-603 (6 pages) (1989).
(Continued)

*Primary Examiner* — Joseph Stoklosa
*Assistant Examiner* — Brian M Antiskay
(74) *Attorney, Agent, or Firm* — Nixon Peabody LLP

(57) ABSTRACT

An apparatus for medical diagnosis and/or treatment is provides. The apparatus includes a flexible substrate forming an inflatable body and a plurality of sensing elements disposed on the flexible substrate. The plurality of sensing elements are disposed about the inflatable body such that the sensing elements are disposed at areas of minimal curvature of the inflatable body in a deflated state.

45 Claims, 64 Drawing Sheets

Related U.S. Application Data on Aug. 23, 2011, provisional application No. 61/661,221, filed on Jun. 18, 2012.

(51) Int. Cl.

| | | |
|---|---|---|
| *A61B 5/03* | (2006.01) | |
| *A61B 18/02* | (2006.01) | |
| *A61B 18/20* | (2006.01) | |
| *A61N 7/02* | (2006.01) | |
| *A61B 5/00* | (2006.01) | |
| *A61B 5/042* | (2006.01) | |
| *A61B 5/04* | (2006.01) | |
| *A61M 29/00* | (2006.01) | |
| *A61B 18/00* | (2006.01) | |
| *A61B 18/14* | (2006.01) | |
| *A61B 18/24* | (2006.01) | |
| *A61B 17/00* | (2006.01) | |
| *A61N 7/00* | (2006.01) | |

(52) U.S. Cl.
CPC ............ *A61B 5/6853* (2013.01); *A61B 18/02* (2013.01); *A61B 18/18* (2013.01); *A61B 18/20* (2013.01); *A61N 7/02* (2013.01); *A61B 5/6858* (2013.01); *A61B 18/1492* (2013.01); *A61B 18/24* (2013.01); *A61B 2017/00526* (2013.01); *A61B 2018/0016* (2013.01); *A61B 2018/0022* (2013.01); *A61B 2018/00577* (2013.01); *A61B 2018/00642* (2013.01); *A61B 2018/00773* (2013.01); *A61B 2018/00791* (2013.01); *A61B 2018/00839* (2013.01); *A61B 2018/00875* (2013.01); *A61B 2018/0212* (2013.01); *A61B 2090/065* (2016.02); *A61B 2562/046* (2013.01); *A61B 2562/125* (2013.01); *A61B 2562/222* (2013.01); *A61N 7/022* (2013.01); *A61N 2007/0078* (2013.01); *Y10T 29/49002* (2015.01); *Y10T 156/1089* (2015.01)

(58) Field of Classification Search
USPC ............... 600/372–377, 380–381, 393, 460, 481, 600/508–509; 604/96.01, 97.01, 99.01, 103.1; 606/20–52
See application file for complete search history.

(56) References Cited

U.S. PATENT DOCUMENTS

| | | | |
|---|---|---|---|
| 5,817,008 A | 10/1998 | Rafert et al. | |
| 5,907,477 A | 5/1999 | Tuttle et al. | |
| 6,063,046 A | 5/2000 | Allum | |
| 6,784,844 B1 | 8/2004 | Boakes et al. | |
| 6,869,431 B2 * | 3/2005 | Maguire | A61B 18/00 604/103 |
| 7,265,298 B2 | 9/2007 | Maghribi | |
| 7,302,751 B2 | 12/2007 | Hamburgen | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |
| 7,557,367 B2 | 7/2009 | Rodgers | |
| 7,618,260 B2 | 11/2009 | Daniel et al. | |
| 7,622,367 B1 | 11/2009 | Nuzzo | |
| 7,759,167 B2 | 7/2010 | Vanfleteren | |
| 7,960,246 B2 | 6/2011 | Flamand | |
| 7,982,296 B2 | 7/2011 | Nuzzo | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rodgers | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rodgers | |
| 8,664,699 B2 | 3/2014 | Nuzzo | |
| 8,679,888 B2 | 3/2014 | Rodgers | |
| 8,729,524 B2 | 5/2014 | Rodgers | |
| 8,754,396 B2 | 6/2014 | Rogers | |
| 8,865,489 B2 | 10/2014 | Rodgers | |
| 8,886,334 B2 | 11/2014 | Ghaffari | |
| 8,905,772 B2 | 12/2014 | Rodgers | |
| 8,920,411 B2 * | 12/2014 | Gelbart | A61B 5/028 606/34 |
| 9,012,784 B2 | 4/2015 | Arora | |
| 2002/0094701 A1 | 7/2002 | Biegelsen et al. | |
| 2002/0113739 A1 | 8/2002 | Howard | |
| 2003/0214408 A1 | 11/2003 | Grajales | |
| 2004/0192082 A1 | 9/2004 | Wagner | |
| 2004/0243204 A1 | 12/2004 | Maghribi | |
| 2005/0096513 A1 | 5/2005 | Ozguz | |
| 2006/0038182 A1 | 2/2006 | Rodgers | |
| 2006/0264767 A1 | 11/2006 | Shennib | |
| 2006/0286785 A1 | 12/2006 | Rogers | |
| 2007/0123756 A1 | 5/2007 | Kitajima et al. | |
| 2008/0046080 A1 | 2/2008 | Vanden Bulcke | |
| 2008/0139894 A1 | 6/2008 | Szydlo-Moore et al. | |
| 2008/0157235 A1 | 7/2008 | Rodgers | |
| 2008/0204021 A1 | 8/2008 | Leussler et al. | |
| 2008/0259576 A1 | 10/2008 | Johnson et al. | |
| 2009/0000377 A1 | 1/2009 | Shipps et al. | |
| 2009/0048556 A1 | 2/2009 | Durand | |
| 2009/0107704 A1 | 4/2009 | Vanfleteren | |
| 2009/0261828 A1 | 10/2009 | Nordmeyer-Massner | |
| 2009/0294803 A1 | 12/2009 | Nuzzo | |
| 2009/0322480 A1 | 12/2009 | Benedict et al. | |
| 2010/0002402 A1 | 1/2010 | Rodgers | |
| 2010/0036258 A1 * | 2/2010 | Dietz | A61B 8/12 600/466 |
| 2010/0059863 A1 | 3/2010 | Rogers | |
| 2010/0072577 A1 | 3/2010 | Nuzzo | |
| 2010/0087782 A1 | 4/2010 | Ghaffari | |
| 2010/0090824 A1 | 4/2010 | Rowell et al. | |
| 2010/0116526 A1 | 5/2010 | Arora | |
| 2010/0178722 A1 | 7/2010 | De Graff | |
| 2010/0245011 A1 | 9/2010 | Chatzopoulos et al. | |
| 2010/0271191 A1 | 10/2010 | De Graff | |
| 2010/0298895 A1 | 11/2010 | Ghaffari | |
| 2010/0317132 A1 | 12/2010 | Rodgers | |
| 2010/0321161 A1 | 12/2010 | Isabell | |
| 2011/0034912 A1 | 2/2011 | De Graff | |
| 2011/0054583 A1 | 3/2011 | Litt | |
| 2011/0101789 A1 | 5/2011 | Salter et al. | |
| 2011/0121822 A1 | 5/2011 | Parsche | |
| 2011/0140897 A1 | 6/2011 | Purks et al. | |
| 2011/0184320 A1 | 7/2011 | Shipps | |
| 2011/0215931 A1 | 9/2011 | Callsen | |
| 2011/0218756 A1 | 9/2011 | Callsen | |
| 2011/0218757 A1 | 9/2011 | Callsen | |
| 2011/0220890 A1 | 9/2011 | Nuzzo | |
| 2011/0277813 A1 | 11/2011 | Rodgers | |
| 2012/0016258 A1 | 1/2012 | Webster et al. | |
| 2012/0051005 A1 | 3/2012 | Vanfleteren | |
| 2012/0052268 A1 | 3/2012 | Axisa | |
| 2012/0065937 A1 | 3/2012 | De Graff | |
| 2012/0087216 A1 | 4/2012 | Keung et al. | |
| 2012/0092178 A1 | 4/2012 | Callsen | |
| 2012/0092222 A1 | 4/2012 | Kato et al. | |
| 2012/0157804 A1 | 6/2012 | Rodgers | |
| 2012/0172697 A1 | 7/2012 | Urman | |
| 2012/0226130 A1 | 9/2012 | De Graff | |
| 2012/0244848 A1 | 9/2012 | Ghaffari | |
| 2012/0256308 A1 | 10/2012 | Helin | |
| 2012/0316455 A1 | 12/2012 | Rahman et al. | |
| 2012/0327608 A1 | 12/2012 | Rodgers | |
| 2013/0035576 A1 * | 2/2013 | O'Grady | A61B 5/04884 600/373 |
| 2013/0041235 A1 | 2/2013 | Rogers et al. | |
| 2013/0099358 A1 | 4/2013 | Elolampi | |
| 2013/0100618 A1 | 4/2013 | Rogers | |
| 2013/0118255 A1 | 5/2013 | Callsen | |

(56) References Cited

U.S. PATENT DOCUMENTS

| | | |
|---|---|---|
| 2013/0150693 A1 | 6/2013 | D'Angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma et al. |
| 2013/0225965 A1 | 8/2013 | Ghaffari |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville et al. |
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |

FOREIGN PATENT DOCUMENTS

| | | |
|---|---|---|
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Notification of Reasons for Refusal dated Jul. 8, 2016 from Japanese Patent Application No. 2014-525091 with English Translation, 11 pages.

\* cited by examiner

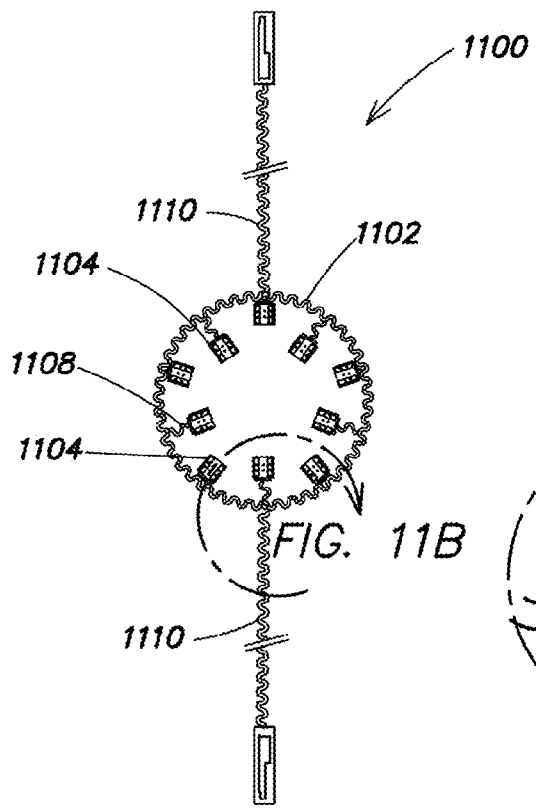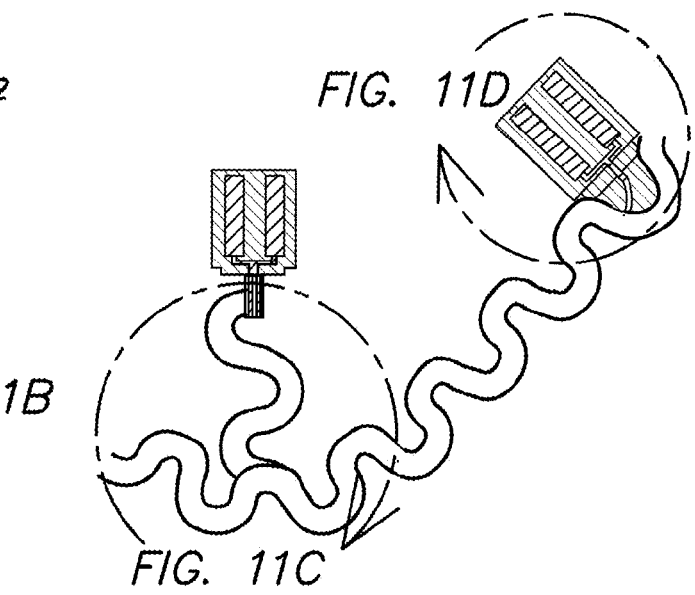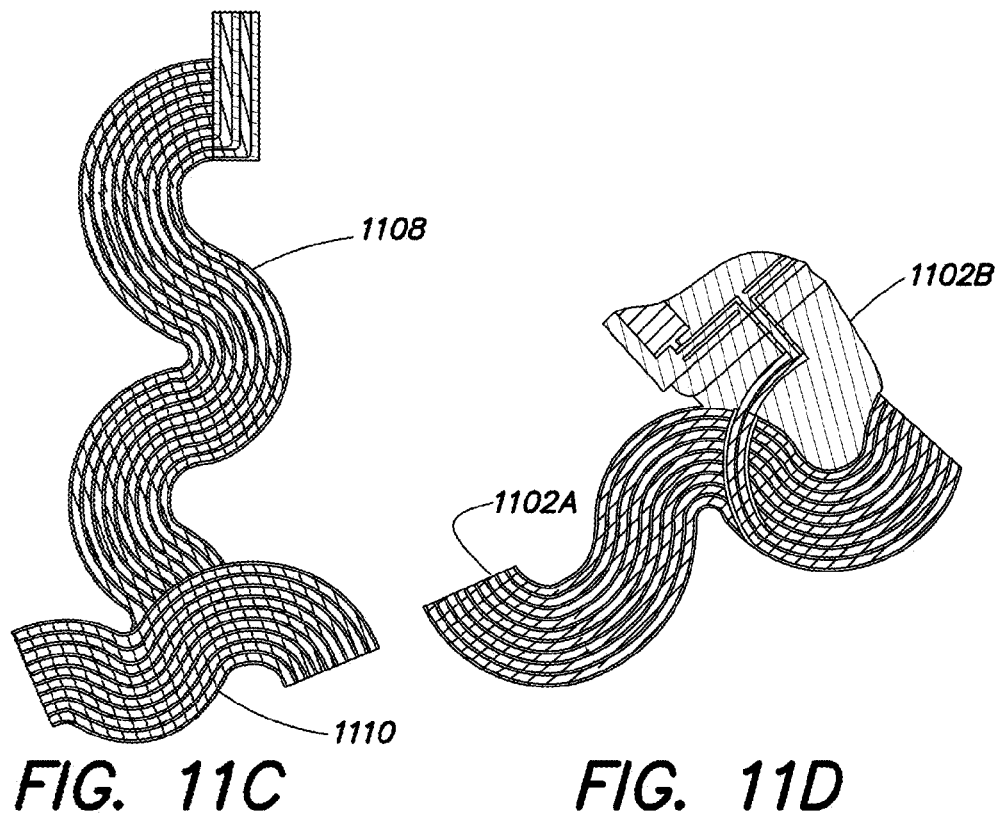
FIG. 11A
FIG. 11B
FIG. 11C
FIG. 11D

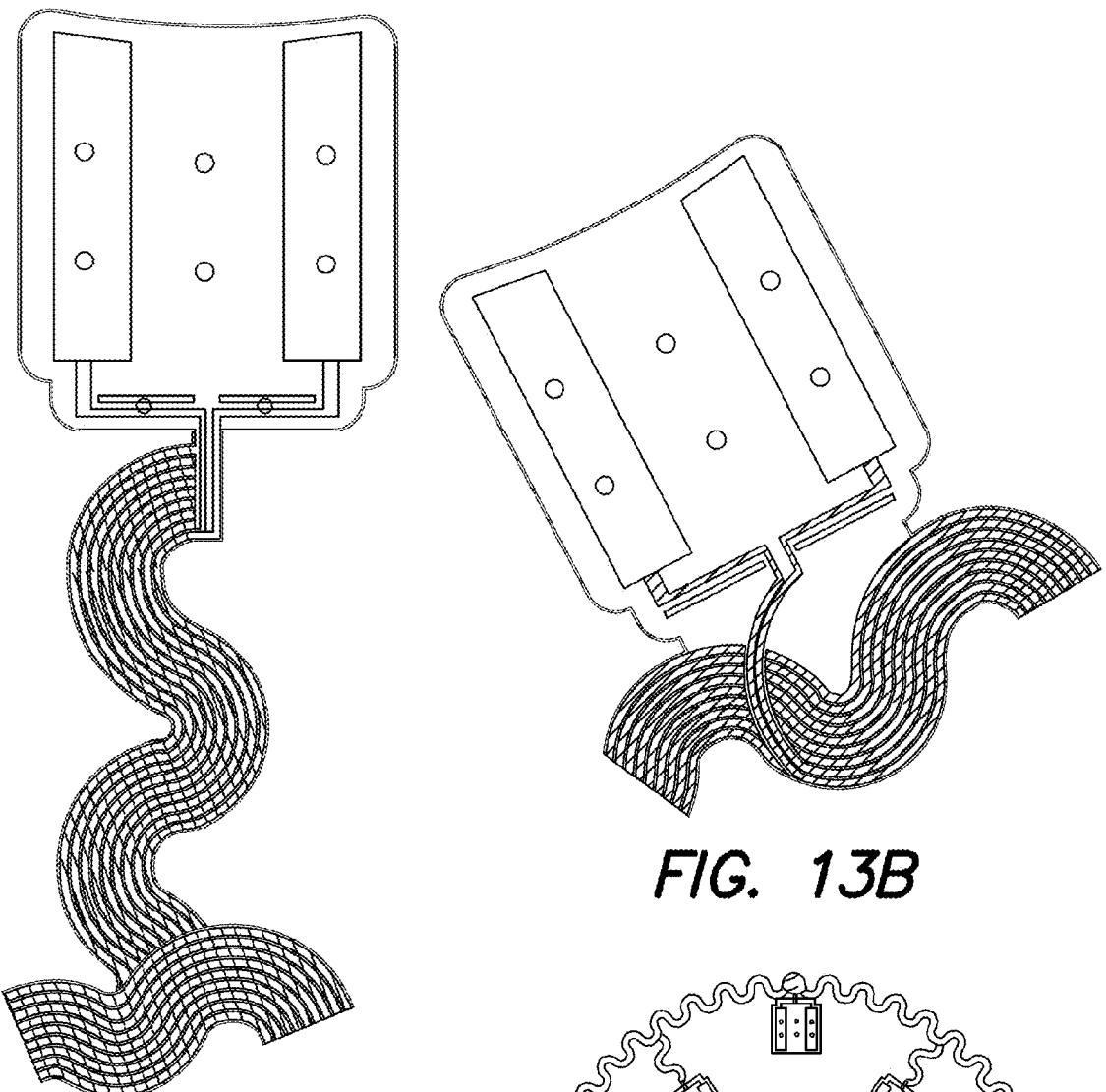
FIG. 13B
FIG. 13A
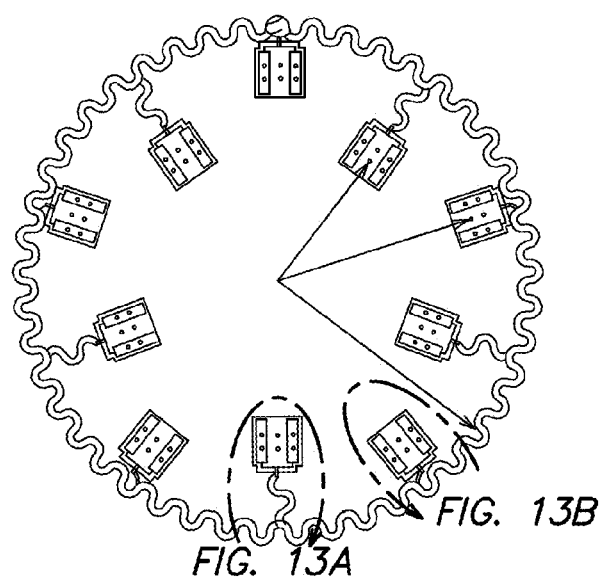
FIG. 13C

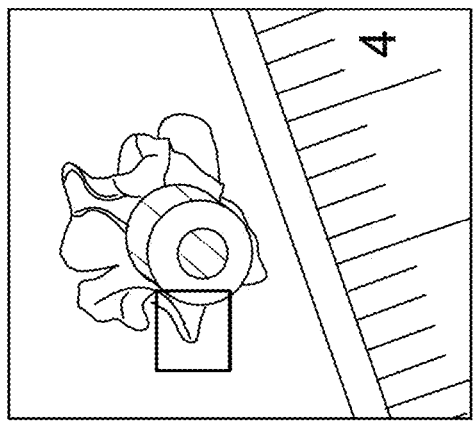
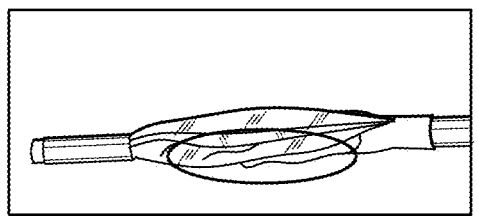
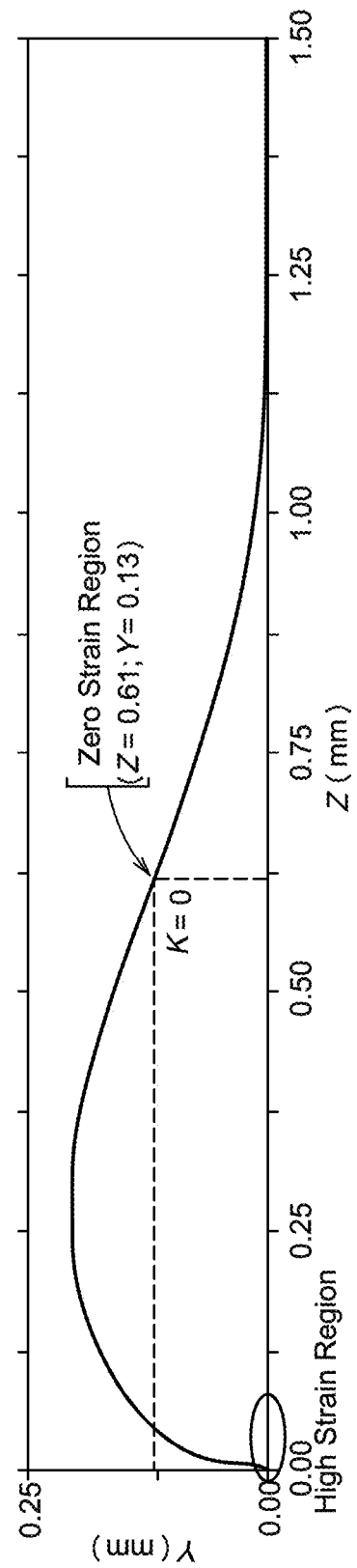
FIG. 20

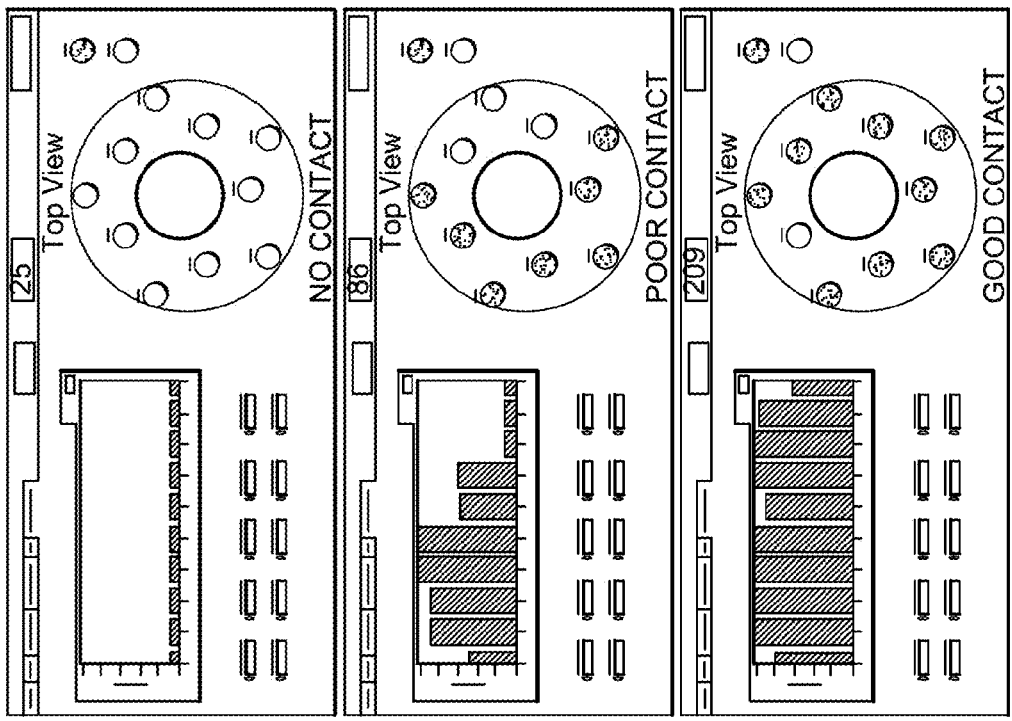
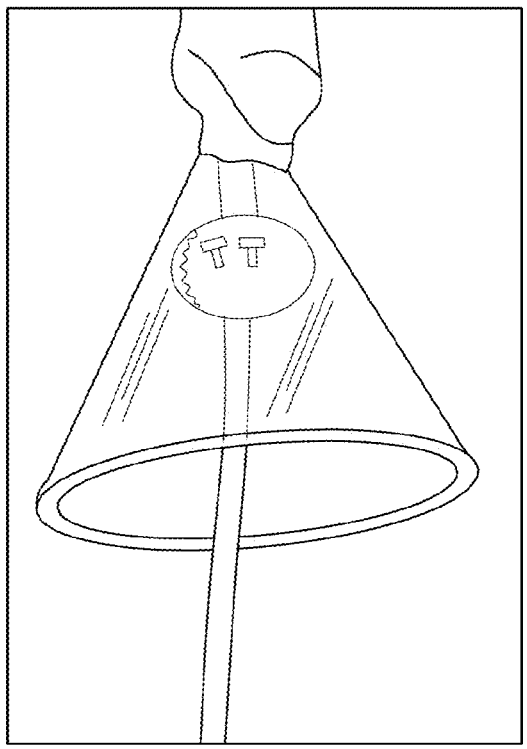
FIG. 49

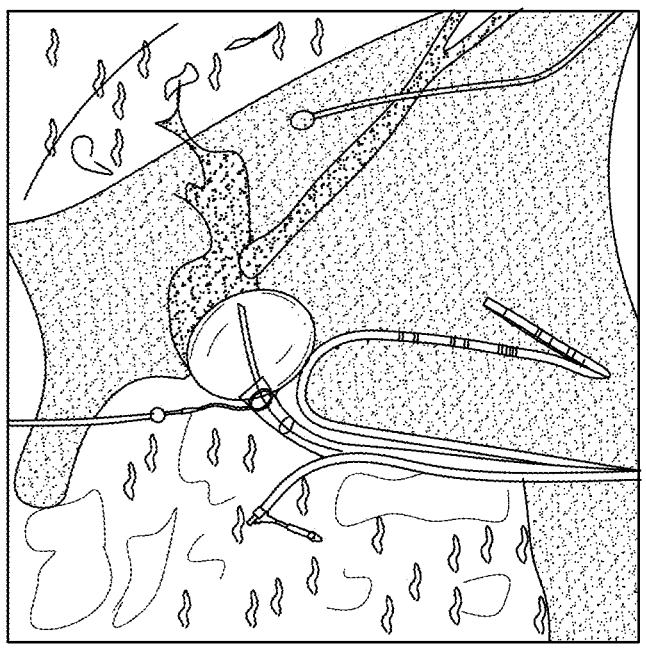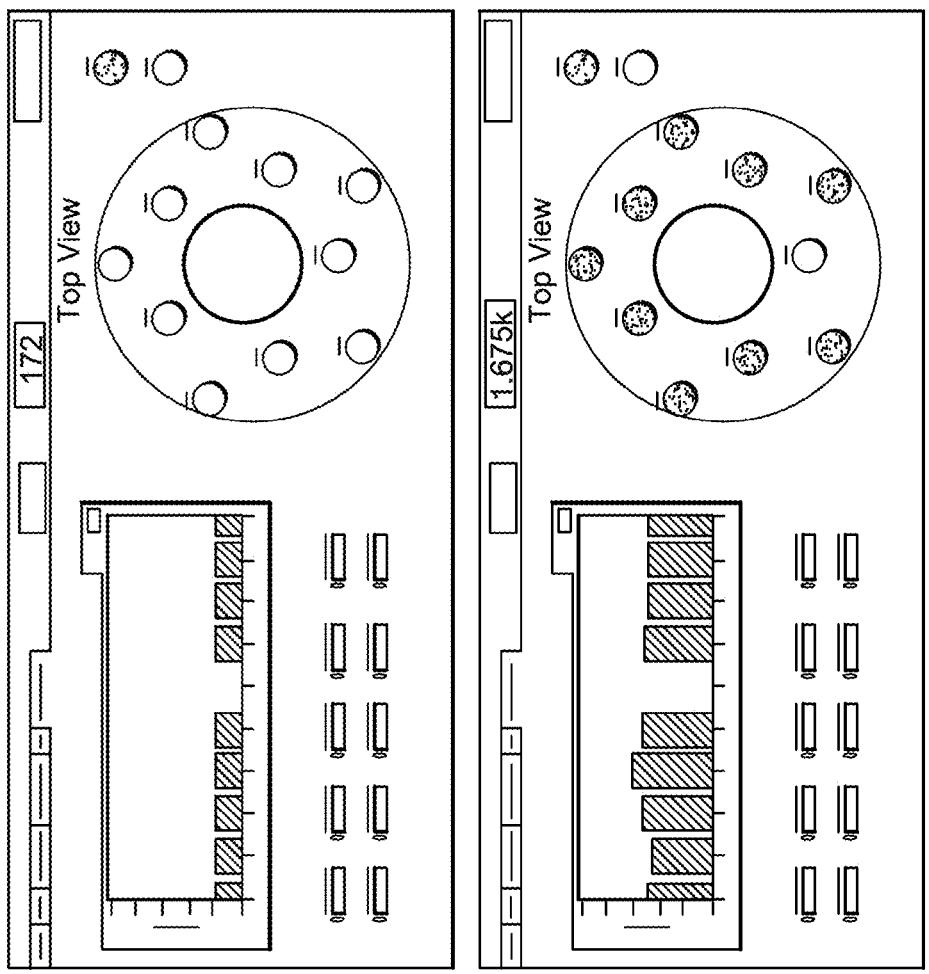
FIG. 50

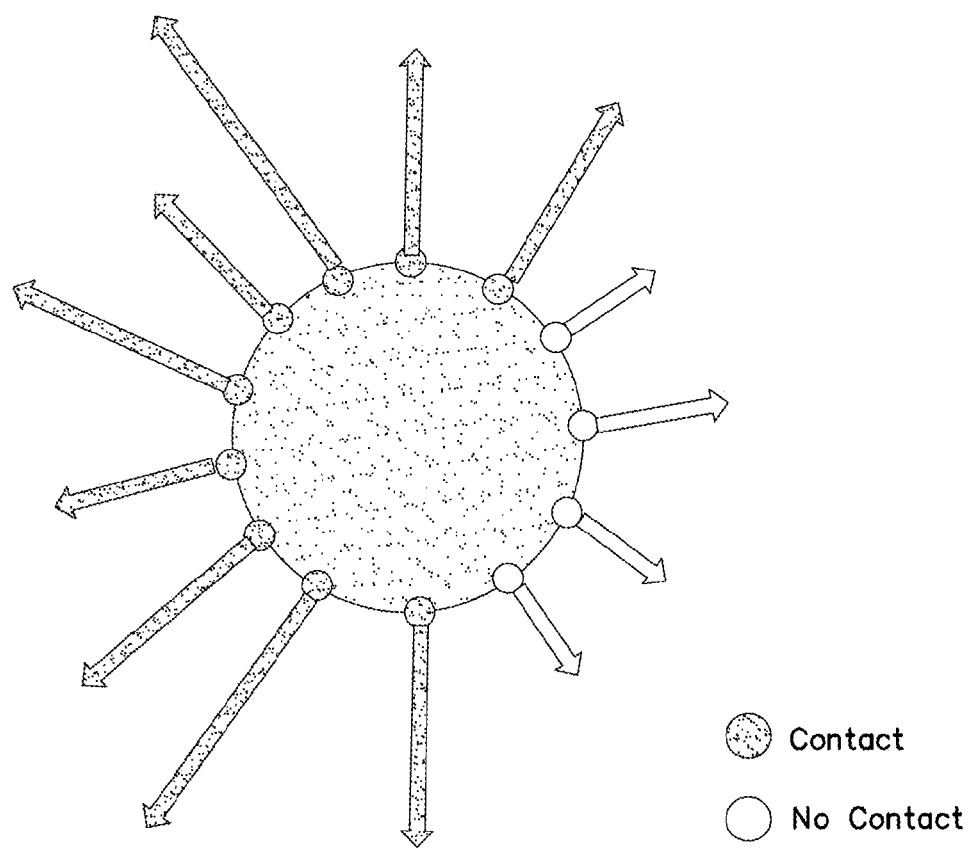
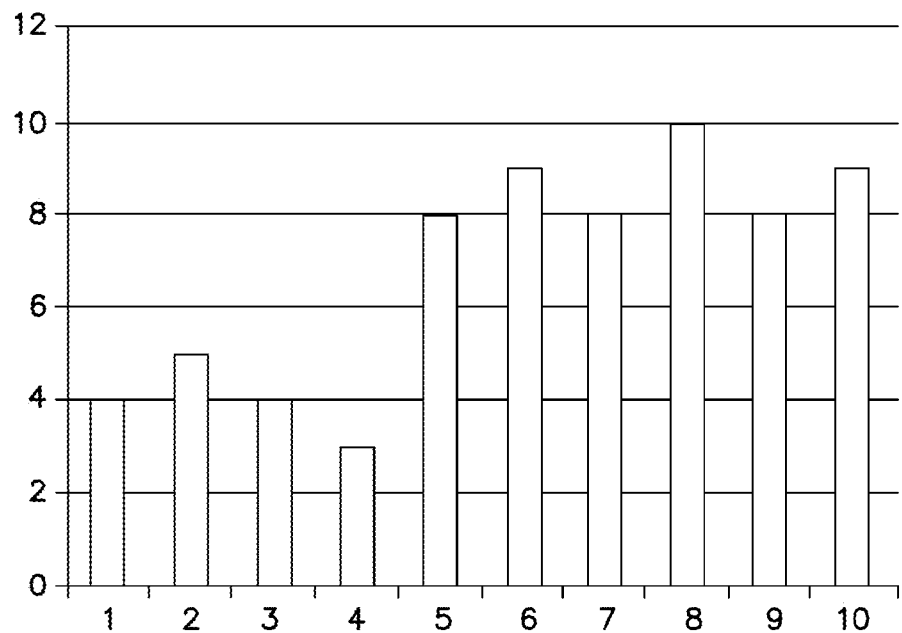
FIG. 53

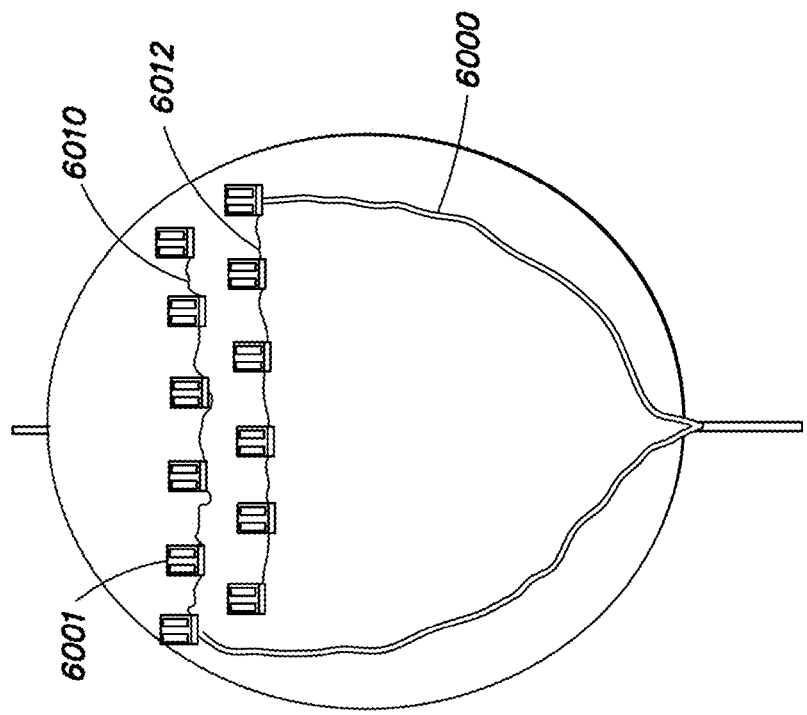
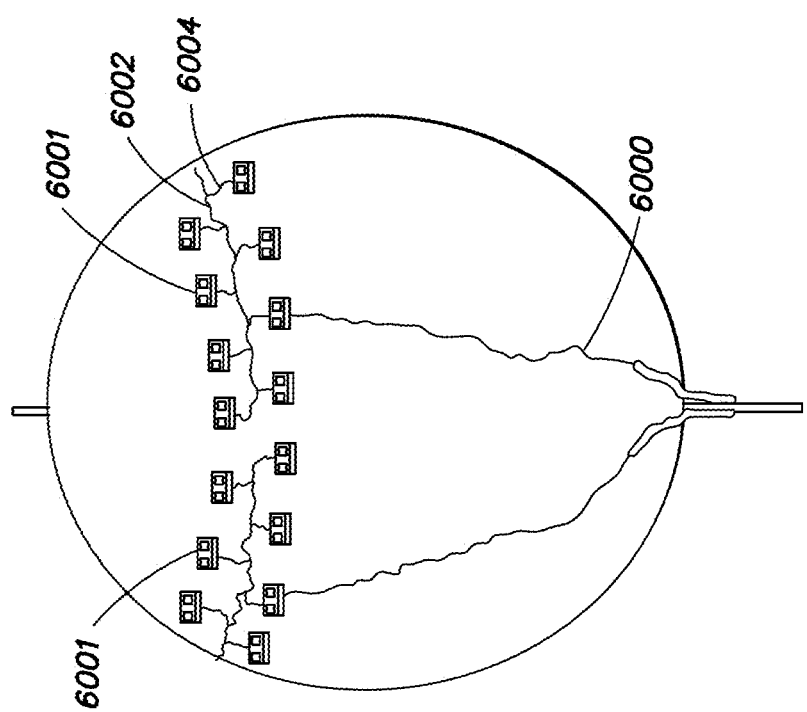
FIG. 60B
FIG. 60A

CATHETER BALLOON METHODS AND APPARATUS EMPLOYING SENSING ELEMENTS

CROSS-REFERENCES TO RELATED APPLICATIONS

This application claims priority to U.S. provisional application Ser. No. 61/515,713, filed Aug. 5, 2011, entitled "Catheter Balloon Methods and Apparatus Employing Lumen Contact Sensors," U.S. provisional application Ser. No. 61/526,516, filed Aug. 23, 2011, entitled "Endocardial Catheter Methods and Apparatus," and U.S. provisional application Ser. No. 61/661,221, filed Jun. 18, 2012, entitled "Conformal Impedance-Based contact Sensors on Arctic Front® Cryoballoon Catheters," each of which is hereby incorporated herein by reference in its entirety.

BACKGROUND

High quality medical sensing and imaging data has become increasingly beneficial in the diagnoses and treatment of a variety of medical conditions. The conditions can be associated with the digestive system, the cardio-circulatory system, and can include injuries to the nervous system, cancer, and the like.

For example, complex fractionated electrogram (CFAE) triggers within the right and left atria play a role in the pathogenesis of persistent and permanent atrial fibrillation, atrial flutters, and tachycardias. Radio frequency (RF) energy (delivered via point bipolar electrodes) can be used to ablate tissues to correct aberrant conduction pathways, aided by imaging data.

SUMMARY

The Inventors have recognized and appreciated that inflatable bodies that include sensing elements can provide data measurements that could beneficial medical diagnosis and/or treatment. The inventors have also recognized that such systems can be made more robust to the use in medical diagnosis and/or treatment environment, provide useful measurements of tissue states (including amount of contact with the tissue), and maintain optimal performance, if the sensing elements are selectively disposed at certain regions of the inflatable body. In view of the foregoing, various embodiments herein are directed generally to methods, apparatus and systems for medical diagnosis and/or treatment that include a flexible substrate forming an inflatable body and a plurality of sensing elements disposed on the flexible substrate, where the sensing elements are selectively disposed at certain regions of the inflatable body.

In some examples herein, an apparatus is provided for medical diagnosis and/or treatment that includes a flexible substrate forming an inflatable body and a plurality of sensing elements disposed on the flexible substrate. The plurality of sensing elements is disposed about the inflatable body such that the sensing elements are disposed at areas of minimal curvature of the inflatable body in a deflated state.

The present disclosure provides some examples of an apparatus for medical diagnosis and/or treatment that include a flexible substrate forming an inflatable body, a coupling bus disposed about a region of the inflatable body, and a plurality of sensing elements disposed on the flexible substrate. The plurality of sensing elements are coupled to the coupling bus and the plurality of sensing elements are disposed about a portion of a circumference of the inflatable body such that the sensor elements are disposed at areas of minimal curvature of the inflatable body in a deflated state.

The coupling bus may be a serpentine bus and the serpentine bus may electrically couple the plurality of sensing elements.

In some examples, the apparatus includes an encapsulation material disposed over substantially a portion of the coupling bus. The encapsulation material may include a polyurethane.

In some examples, the apparatus includes a shaft coupled to the inflatable body, a flex board disposed over or inside the shaft, a plurality of wires connected to the flex board to provide and/or obtain electrical signals to the flex board, and an intermediate bus electrically coupled to a flex board and to the plurality of sensors. The plurality of sensing elements may include at least one of a pressure sensor or an impedance sensor.

The shaft may include a cryoablation device, a laser ablation device, a high intensity ultrasound or a RF device, in some examples.

In some examples, the sensing elements of the apparatus are disposed in a longitudinal direction along portions of the inflatable body that experience minimal strain when the inflatable body is in a deflated state.

In some examples, the coupling bus is an annular bus, and the annular bus is disposed as a ring substantially about a circumference of the inflatable body.

The coupling bus of the apparatus is a serpentine bus including a plurality of serpentine structures, in accordance with some examples.

One or more of the sensing elements of the plurality of sensing elements may include contact sensors, in some examples.

In some examples, the plurality of sensing elements is disposed about an equator of the inflatable body.

In some examples, the plurality of sensing elements is disposed proximate to a distal portion of the inflatable body.

In some examples, the plurality of sensing elements of the apparatus is disposed in helical pattern about the inflatable body.

In some examples, the apparatus includes an encapsulation layer disposed over the plurality of sensing elements. The encapsulation layer may position the sensing elements at a neutral mechanical plane.

The encapsulation layer may include a polymer, in some examples.

In some examples, the apparatus includes at least one intermediate layer disposed between the plurality of sensing elements and the inflatable body, where the at least one intermediate layer positions the sensing elements at the neutral mechanical plane.

In some examples, the inflatable body is disposed near a distal end of a catheter.

In some examples, the inflatable body is a balloon. The balloon may be cylindrical, onion-shaped, cone-shaped, dog-bone-shaped, and barrel-shaped.

The coupling bus may have a T-configuration or an annular ring structure.

In some examples, the apparatus includes an encapsulation material disposed over substantially a portion of the plurality of sensing elements. The encapsulation material may include polyurethane.

In some examples, the sensing elements are formed from a conductive material.

In some examples, the coupling bus is formed from a conductive material.

The present disclosure provides some examples of a method of fabricating an apparatus for medical diagnosis and/or treatment. The example method includes providing a coupling bus that is coupled to a plurality of sensing elements, disposing the coupling bus about a region of an inflatable body, and disposing the plurality of sensing elements about a portion of a circumference of the inflatable body such that the sensor elements are disposed at areas of minimal curvature of the inflatable body.

The method may include extracting the coupling bus and the plurality of sensing elements from a carrier substrate prior to disposing the coupling bus about the region of the inflatable body.

In some examples, the disposing the coupling bus about the region of the inflatable body includes applying the coupling bus using a dissolvable tape backing.

In some examples, the coupling bus is disposed near a distal region of the inflatable body and the plurality of sensing elements is disposed closer to a mid-portion of the inflatable body.

The present disclosure provides some examples of a method of performing a medical diagnosis and/or treatment on a tissue that include disposing in proximity to the tissue an apparatus including a flexible substrate forming an inflatable body, a coupling bus, and a plurality of sensing elements that are coupled to the coupling bus. The one or more sensing elements of the plurality of sensing elements include contact sensors. The coupling bus is disposed near a distal end of the inflatable substrate. The plurality of sensing elements is disposed about the inflatable body such that the sensing elements are disposed at areas of minimal curvature of the inflatable body. The method further includes recording a measurement of at least one sensing element of the plurality of sensing elements. The measurement provides an indication of a state of a portion of the tissue.

In some examples, the measurement provides an indication of a disease state of the portion of the tissue.

In some examples, the measurement provides an indication of a contact state of the portion of the tissue with the at least one sensing element of the plurality of sensing elements.

The present disclosure provides examples of an apparatus for displaying a representation of measurements of a plurality of sensing elements disposed about at least a portion of a circumference of an inflatable body during a medical diagnosis and/or treatment of a tissue. The apparatus includes display, a memory storing machine-readable instructions, and one or more processor units to execute the machine-readable instructions. The execution of the machine-readable instructions causes the display to display the representation of the measurements. In this example, the representation includes (i) a plurality of first indicators, each first indicator corresponding to a sensing element of the plurality of sensing elements that measures a signal below a threshold value, and (ii) a plurality of second indicators, each second indicator corresponding to a sensing element of the plurality of sensing elements that measures a signal above the threshold value.

In some examples, the measurement below the threshold value indicates that the corresponding sensing element of the plurality of sensing elements is not in contact with the tissue.

In some examples, the measurement above the threshold value indicates that at least a portion of the corresponding sensing element of the plurality of sensing elements is in contact with the tissue.

The present disclosure provides examples of an apparatus for displaying a representation of measurements of a plurality of sensing elements disposed about at least a portion of a circumference of an inflatable body during a medical diagnosis and/or treatment of a tissue. The apparatus includes a display, a memory storing machine-readable instructions, and one or more processor units to execute the machine-readable instructions. In this example, the execution of the machine-readable instructions causes the display to display the representation of the measurements. In this example, the representation includes (i) a plurality of first spatial representations, each first spatial representation corresponding to a sensing element of the plurality of sensing elements that is disposed at a first latitude of the inflatable body, and (ii) a plurality of second spatial representations, each second spatial representation corresponding to a sensing element of the plurality of sensing elements that is disposed at a second latitude of the inflatable body that is different from the first latitude.

In some examples, each of the first spatial representations or each of the second spatial representations displays a first indication if the corresponding sensing element measures a signal above a threshold value.

In some examples, each of the first spatial representations or each of the second spatial representations displays a second indication if the corresponding sensing element measures a signal below a threshold value.

The present disclosure provides examples of a stretchable electronic system. The stretchable electronic system includes a flexible annular interconnect and a first plurality of electrodes coupled to the flexible annular interconnect.

In some examples, the flexible annular interconnect has a first radius and each electrode in the first plurality of electrodes is coupled to the flexible annular interconnect via at least one flexible connector extending from the annular interconnect such that the first plurality of electrodes are positioned at a second radius distinct from the first radius.

In some examples, the flexible annular interconnect is formed from a conductive material.

In some examples, the second radius is greater than the first radius.

The stretchable electronic may include a second plurality of electrodes coupled to the flexible annular interconnect. Each electrode in the second plurality of electrodes may be coupled to the flexible annular interconnect via the at least one flexible connector extending from the annular interconnect such that the second plurality of electrodes are positioned at a third radius, distinct from the first and second radii.

In some examples, the third radius is greater than the second radius.

In some examples, the stretchable electronic system includes a flexible substrate forming an inflatable body. The flexible annular interconnect and the first plurality of electrodes may be coupled to a peripheral portion of the flexible substrate.

In some examples, the inflatable body is disposed near a distal end of a catheter.

The inflatable body may be a balloon. The balloon may be cylindrical, onion-shaped, cone-shaped, dog-bone-shaped, and barrel-shaped.

In some examples, the flexible annular interconnect comprises at least one intermediate bus for electronically connecting each electrode with an electrical source.

In some examples, the flexible annular interconnect has a serpentine morphology.

The stretchable electronic system may also include a flexible substrate forming an inflatable body coupled to the flexible annular interconnect. The flexible annular interconnect may have a T-configuration or an annular ring structure. The flexible annular interconnect may have a T-configuration or an annular ring structure.

In some examples, the stretchable electronic system includes an encapsulation material disposed over at least a portion of the flexible annular interconnect or the plurality of sensing elements. The encapsulation material may include polyurethane.

In some examples, the stretchable electronic system includes an intermediate layer disposed between the flexible annular interconnect.

The present disclosure provides examples of a system for mapping contact with a surface. The system includes an inflatable body, a plurality of electrodes coupled to the inflatable body, and an electronic display electrically coupled to the plurality of electrodes, the electronic display providing a visual representation of the spatial location of the plurality of electrodes on the inflatable body. The electronic display changes a visual attribute of an electrode in the plurality of electrodes in response to a change in an electrical signal produced by the electrode. The change in the electrical signal identifies a contact condition of the electrode with respect to the surface.

In different examples, the visual attribute is a binary representation or a quantitative representation.

The present disclosure provides examples of a stretchable electronic system that include a flexible interconnect and a plurality of impedance based electrode pairs coupled to the flexible interconnect. The electrode pairs measure impedance between two electrodes of the electrode pair.

The present disclosure provides some examples of a method of manufacturing a contact mapping balloon catheter. The method includes identifying regions of maximum curvature on the balloon of the balloon catheter when the balloon is in a deflated state and coupling a plurality of electrodes to the balloon such that the plurality of electrodes are positioned outside of the regions of maximum curvature.

In accordance with examples disclosed herein, co-locating contact sensors (electrical, pressure, thermal or otherwise) with the therapeutic facility (which may comprise any circuitry and elements to delivery ablation described herein) can reduce or eliminate the need for dyes and may reduce the time to complete the procedure. Further, example systems and apparatus disclosed herein can be implemented to both deliver the ablative therapy and the same device during the same procedure can be implemented to generate data regarding of the electrical conductivity of the site post-ablation.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS."

Kim, D. H. et al. (2010). Dissolvable films of silk fibroin for ultrathin conformal bio-integrated electronics. *Nature Materials*, 9, 511-517.

Omenetto, F. G. and D. L. Kaplan. (2008). A new route for silk. *Nature Photonics*, 2, 641-643.

Omenetto, F. G., Kaplan, D. L. (2010). New opportunities for an ancient material. *Science*, 329, 528-531.

Halsed, W. S. (1913). Ligature and suture material. *Journal of the American Medical Association*, 60, 1119-1126.

Masuhiro, T., Yoko, G., Masaobu, N., et al. (1994). Structural changes of silk fibroin membranes induced by immersion in methanol aqueous solutions. *Journal of Polymer Science*, 5, 961-968.

Lawrence, B. D., Cronin-Golomb, M., Georgakoudi, I., et al. (2008). Bioactive silk protein biomaterial systems for optical devices. *Biomacromolecules*, 9, 1214-1220.

Demura, M., Asakura, T. (1989). Immobilization of glucose oxidase with *Bombyx mori* silk fibroin by only stretching treatment and its application to glucose sensor. *Biotechnololgy and Bioengineering*, 33, 598-603.

Wang, X., Zhang, X., Castellot, J. et al. (2008). Controlled release from multilayer silk biomaterial coatings to modulate vascular cell responses. *Biomaterials*, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

Further combinations and sub-combinations of various concepts are provided below in the claims section. It should be appreciated that all combinations of such concepts and additional concepts described in greater detail below (provided such concepts are not mutually inconsistent) are contemplated as being part of the inventive subject matter disclosed herein. In particular, all combinations of subject matter appearing as numbered claims at the end of this disclosure are contemplated as being part of the inventive subject matter disclosed herein. In addition, all combinations of subject matter supported by this disclosure, including the drawings, the description and the claims, are contemplated as being part of the inventive subject matter even if not expressly recited as one of the numbered claims.

It should be appreciated that all combinations of the foregoing concepts and additional concepts described in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 11A-11D illustrate an example of a stretchable electronic system, according to the principles described herein.

FIG. 13A illustrates a magnified view of example integrated components of the electrode design of FIG. 13C, as indicated by the circular callout line 13A in FIG. 13C, according to the principles described herein.

FIG. 13B illustrates another magnified view of example integrated components of the electrode design of FIG. 13C, as indicated by the circular callout line 13B in FIG. 13C, according to the principles described herein.

FIG. 13C illustrates an electrode design, according to the principles described herein.

FIG. 20 is a graph illustrating example computation of the change in strain along a folded section of a deflated balloon, according to the principles described herein.

FIG. 49 provides a series of screen shots of an example graphical user interface demonstrating a variety of conditions simulated with a balloon catheter including integrated sensing electronics positioned in a glass heart, according to the principles described herein.

FIG. 50 provides a series of screen shots of an example graphical user interface demonstrating a variety of contact conditions with a balloon catheter including integrated sensing electronics positioned in a tissue lumen of a live pig, according to the principles described herein.

FIG. 53 demonstrates an example user interface displaying quantitative read outs of sensors disposed on a balloon catheter, according to the principles described herein.

FIGS. 60A-60B illustrates further additional examples of the sensor array, including "L" shaped arrays, according to the principles described herein.

Figure 1:
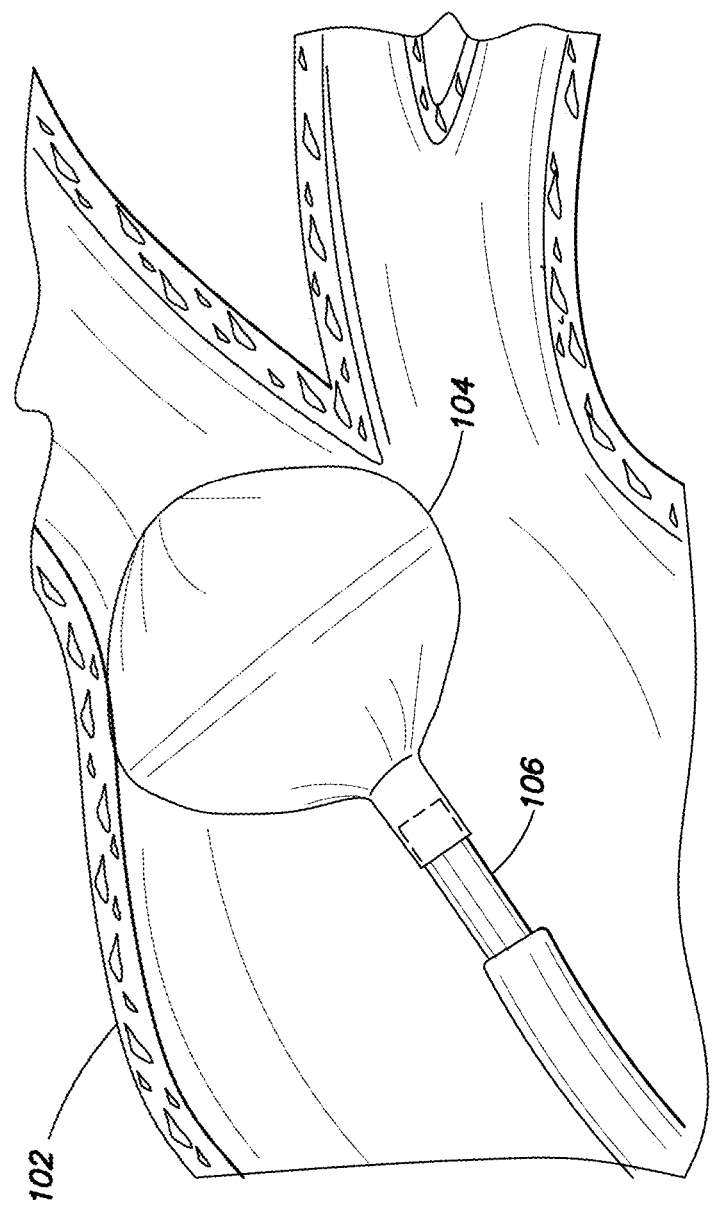
FIG. 1 illustrates an example illustration of an incomplete occlusion of the ostium or pulmonary vein by a catheter balloon, where a dye is deployed to help visualization of the incomplete occlusion according to the principles described herein.

The features and advantages of the various examples will become more apparent from the detailed description set forth below when taken in conjunction with the drawings.

DETAILED DESCRIPTION

Following below are more detailed descriptions of various concepts related to, and examples of inventive systems, methods and apparatus for use with balloon catheters and other types of catheters. The systems, methods and apparatus used for medical diagnosis and/or treatment. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but not limited to, the term "including" means including but not limited to. The term "based on" means based at least in part on.

An example system, method and apparatus described herein can be used for medical diagnosis and/or treatment. The example apparatus can include a flexible substrate that forms an inflatable body and a plurality of sensing elements disposed on the flexible substrate. The plurality of sensing elements can be disposed about the inflatable body such that the sensing elements are disposed at areas of minimal curvature of the inflatable body in a deflated state (which includes a collapsed state).

In any example described herein, an area of minimal curvature may correspond to, and/or lie proximate to, regions of low and/or minimal strain in the inflatable body in the deflated state.

In an example, the inflatable body can be formed from any suitable flexible and/or stretchable material in the art. Non-limiting examples include polyethylene terephthalate (PET), polyurethane, and nylon.

In an example, the inflatable body can be configured as an expandable portion positioned near an end of a catheter. In non-limiting examples, the inflatable body can be a balloon catheter. For example, the inflatable body can be a balloon having a cylindrical morphology, a cone shaped morphology or dog-bone shaped morphology, an "onion"-shaped morphology (i.e., a shape that can exhibit different curvatures in x- and y-directions), or a barrel-like morphology. In another example, the inflatable body may have a compound shape. For example, the inflatable body may be rounded in shape in certain portions, and include at least one portion that is flattened. In another example, the inflatable body may be configured as a flattened stretchable portion that can be expanded or collapsed. In an example implementation, such a flattened portion of the inflatable body may be deployed to make substantially full contact with a portion of a tissue, e.g., as part of a tissue lumen.

Non-limiting examples of a tissue lumen according to the principles of any of the examples described herein include the channel within a tubular tissue structure, such as but not limited to a blood vessel (including an artery or a vein), or to the cavity within a hollow portion of an organ, such as but not limited to an intestine, an oral canal, a heart, a kidney, or auditory canal, Another example system, method and apparatus described herein that can be used for medical diagnosis and/or treatment includes a flexible substrate that forms an inflatable body, a coupling bus disposed about a region of the inflatable body, and a plurality of sensing elements disposed on the flexible substrate. The plurality of sensing elements are coupled to the coupling bus. Also, the plurality of sensing elements are disposed about a portion of a circumference of the inflatable body such that the sensor elements are disposed at areas of minimal curvature of the inflatable body in a deflated state (which includes a collapsed state).

In an example, the coupling bus is disposed near a distal region of the inflatable body and the plurality of sensing elements are disposed closer to a mid-portion of the inflatable body.

In another example, the coupling bus is disposed near a mid-portion of the inflatable body and the plurality of sensing elements are disposed closer to a distal region of the inflatable body.

An example electronic structure according to the principles herein includes a coupling bus and a plurality of sensing elements that are coupled to the coupling bus. In an example, the plurality of sensing elements can be configured to extend to substantially the same distance or radius from the coupling bus. In another example, one or more sensing element of the plurality of sensing elements can be configured to extend a different distance from the coupling bus than that of the other sensing elements of the plurality of sensing elements. For example, a number of the plurality of sensors can extend to a first distance of radius from the coupling bus, while the remaining sensors can all extend to a second distance or radius greater than the first. In yet another example, the plurality of sensing elements can extend to three different distances or radii from the coupling bus.

In an example, the coupling bus can include conductive portions that facilitate electrical communication between the sensing elements and an external circuit. For applications where a high conductivity is beneficial, a metal or metal alloy may be used, including but not limited to aluminum or a transition metal (including copper, silver, gold, platinum, zinc, nickel, chromium, or palladium, or any combination thereof) and any applicable metal alloy, including alloys with carbon. Suitable conductive materials may include a semiconductor-based conductive material, including a silicon-based conductive material, indium tin oxide, or Group III-IV conductor (including GaAs).

In another example, the coupling bus can include such conductive portions and also non-conductive portions. Such non-conductive portions can be used to achieve a symmetric shape and/or weight distribution of the coupling bus, to introduce a mechanical stability to the coupling bus-sensing elements system, to reduce or eliminate a strain at a junction between a connector from the sensing element and the coupling bus, to encapsulate the conductive portions for performance, electrical and or mechanical stability, and/or to isolate the conductive portions from an external strain applied to the system during use in a medical diagnostic and/or treatment procedure. The non-conductive portion can be a polymeric material, such as but not limited to a polyimide, a polyethylene terephthalate (PET), or a polyeurethane. Other non-limiting examples of applicable polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer herein can be a DYMAX® polymer (Dymax Corporation, Torrington, Conn.). or other UV curable polymer.

In an example, the coupling bus can be shaped as an annular ring structure, an oval structure, a polygonal structure, such as but not limited to a pentagonal, hexagonal or octagonal structure, or other closed-loop structure. In another example, the coupling bus can be a structure with arms or other extending open-loop structure that can be wrapped around at least a portion of an inflatable body. The coupling bus according to a system, apparatus and method herein can be configured to wrap around, or otherwise encircle, at least partially a portion of an inflatable body.

In an example, the plurality of sensing elements can include one or more of multiple sensor types, such as but not limited to, impedance sensors (including bipole electrodes), lateral strain sensors, temperature sensors, intracardiac electrogram (EGM) sensors, light-emitting diodes (LEDs), including micro-LEDs, transistors (including switches), multiplexors, recording electrodes, radiofrequency (RF) electrodes (including RF ablation electrodes), temperature sensors, and/or contact sensors (including impedance-based contact sensors).

In an example, the plurality of sensing elements can include combinations of different sensor types. In an example, the plurality of sensing elements can include components such as pacing electrodes, EGM electrodes, and bipolar electrodes. In another example, the plurality of sensing elements can include components such as impedance electrodes and contact sensing electrodes. In another example, the plurality of sensing elements can include power control components such as components that can perform ablation. In another example, the plurality of sensing elements can include active components such as components that can provide for local signal amplification, e.g., for buffering or to provide signal gain. In any example where the sensing elements include active components, the activation of the active component and the measurements from the active component can be multiplexed.

In any example according to the principles described herein, the sensing elements, including electrodes, can be formed as conformal components, to conform to a shape and/or movement of a surface over which they are disposed, including in flexibility and/or stretchability.

In an example, the sensing elements can be coupled to the coupling bus using at least one flexible connector. In an example, each sensing element can be coupled to the coupling bus using a respective flexible connector. In another example, two or more of the sensing elements can be coupled to the coupling bus by a single flexible connector.

Another example system, method and apparatus described herein that can be used for medical diagnosis and/or treatment includes a flexible substrate that forms an expandable body and a plurality of sensing elements disposed on the flexible substrate. The plurality of sensing elements can be disposed about the expandable body such that the sensing elements are disposed at areas of minimal strain of the expandable body when in an unexpanded state.

Methods for fabricating an apparatus for medical diagnosis and/or treatment are also described. An example method includes providing a coupling bus that is coupled to a plurality of sensing elements, disposing the coupling bus about a region of an inflatable body, and disposing the plurality of sensing elements about a portion of a circumference of the inflatable body such that the sensor elements are disposed at areas of minimal curvature of the inflatable body.

In various examples, the coupling bus can be disposed near a mid-portion of an inflatable body, for examples, near an equator of an inflatable body. In other examples, the coupling bus can be disposed at a position away from the mid-portion of the inflatable body, for example, near a distal portion of the inflatable body. Regardless of the location of the coupling bus relative to the inflatable body, the stretchable electronic system can be configured such that the sensing elements are positioned at regions of minimal curvature of the inflatable body in the deflated state according to the principles described herein.

An example method for fabricating an apparatus for medical diagnosis and/or treatment can include extracting the coupling bus and the plurality of sensing elements from a carrier substrate prior to disposing the coupling bus about the region of the inflatable body. In an example method, disposing the coupling bus about the region of the inflatable body can include applying the coupling bus using a dissolvable tape backing.

According to the principles described herein, a stretchable electronic system is also provided. The stretchable electronic system includes at least one flexible annular interconnect and a plurality of electrodes coupled to the at least one flexible annular interconnect. The at least one flexible interconnect can be configured similarly to the coupling bus described above, including being formed from similar materials or combinations of materials, in similar shapes, and/or with similar electrical and/or mechanical properties.

In an example, the plurality of electrodes elements can include one or more of bipole electrodes, intracardiac electrogram (EGM) electrodes, recording electrodes, and radiofrequency (RF) electrodes (including RF ablation electrodes).

In an example, the at least one flexible annular interconnect has a first radius and each electrode in the first plurality of electrodes is coupled to the at least one flexible annular interconnect via a respective flexible connector extending from the annular interconnect such that the first plurality of electrodes are positioned at a second radius distinct from the first radius. The second radius can be greater than or less than the first radius.

In another example, the at least one flexible annular interconnect can include a second plurality of electrodes coupled to the at least one flexible annular interconnect, each electrode in the second plurality of electrodes coupled to the at least one flexible annular interconnect via a flexible connector extending from the annular interconnect such that the second plurality of electrodes are positioned at a third radius, distinct from the first and second radii. The third radius can be greater than the second radius.

In an example, the stretchable electronic system can include a flexible substrate forming an inflatable body, the at least one flexible annular interconnect and the first plurality of electrodes coupled to a peripheral portion of the flexible substrate. In an example, the at least one flexible annular interconnect can include at least one intermediate bus to electronically connect each electrode with an electrical source. The at least one flexible annular interconnect can be configured in a serpentine morphology. In an example, the stretchable electronic can further include a flexible substrate forming an inflatable body coupled to the at least one flexible annular interconnect.

In an example, any system or apparatus according to the principles described herein may be entirely or at least partially encapsulated by an encapsulating material, such as a polymer material (including any of the polymer materials described herein). An encapsulating material can be any material that can be used to laminate, planarize, or encase at least one component of a system or apparatus described herein, including any electronic or other type of component. For example, a method of fabricating any system or apparatus according to the principles described herein can further include encapsulating the system or apparatus. In an example, an encapsulating material can be disposed over, or otherwise applied to, an apparatus that includes the flexible substrate forming the inflatable body and the plurality of sensing elements disposed on the flexible substrate, or a stretchable electronic system that includes a flexible annular interconnect and a plurality of electrodes coupled to the flexible annular interconnect, where the stretchable electronic system is disposed on an inflatable body. In various examples, an encapsulating material can be disposed over, or otherwise applied to, solely to the plurality of sensing elements, the coupling bus, and/or the stretchable electronic system that includes the flexible annular interconnect and the plurality of electrodes. In an example, a polyurethane can be used as the encapsulating material. In another example, the encapsulating material can be the same material as the material for the flexible substrate. Encapsulating any portion of the systems or apparatus described herein can be useful to enhance the mechanical stability and robustness of the system or apparatus, or to maintain electronic performance of the electronic components of the system or apparatus against a stress or strain applied to the system or apparatus during use.

In an example, any of the systems or apparatus according to the principles herein can be disposed on the inflatable body such that a functional layer of the system or apparatus lies at a neutral mechanical plane (NMP) or neutral mechanical surface (NMS) of the system or apparatus. The NMP or NMS lies at the position through the thickness of the device layers for the system or apparatus where any applied strains are minimized or substantially zero. In an example, the functional layer of a system or apparatus according to the principles described herein includes the plurality of sensing elements, the coupling bus, and/or the stretchable electronic system that includes the flexible annular interconnect and the plurality of electrodes.

The location of the NMP or NMS can be changed relative to the layer structure of the system or apparatus through introduction of materials that aid in strain isolation in various layers of the system or apparatus. In various examples, polymer materials described herein can be introduced to serve as strain isolation materials. For example, the encapsulating material described hereinabove can be used to position the NMP or NMS, e.g., by varying the encapsulating material type and/or layer thickness. For example, the thickness of encapsulating material disposed over the functional layers described herein may be modified (i.e., decreased or increased) to depress the functional layer relative to the overall system or apparatus thickness, which can vary the position of the NMP or NMS relative to the functional layer. In another example, the type of encapsulating, including any differences in the elastic (Young's) modulus of the encapsulating material.

In another example, at least a partial intermediate layer of a material capable of providing strain isolation can be disposed between the functional layer and the flexible substrate to position the NMP or NMS relative to the functional layer. In an example, the intermediate layer can be formed from any of the polymer materials described herein, aerogel materials or any other material with applicable elastic mechanical properties.

Based on the principles described herein, the NMP or NMS can be positioned proximate to, coincident with or adjacent to a layer of the system or apparatus that includes the strain-sensitive component, such as but not limited to the functional layer. The layer can be considered "strain-sensitive" if it is prone to fractures or its performance can be otherwise impaired in response to a level of applied strain. In an example where the NMP or NMS is proximate to a strain-sensitive component rather than coincident with it, the position of the NMP or NMS may still provide a mechanical benefit to the strain-sensitive component, such as substantially lowering the strain that would otherwise be exerted on the strain-sensitive component in the absence of strain isolation layers. In various examples, the NMS or NMP layer is considered proximate to the strain-sensitive component that provides at least 10%, 20%, 50% or 75% reduction in strain in the strain-sensitive component for a given applied strain, e.g., where the inflatable body is inflated.

In various examples, the encapsulating material and/or the intermediate layer material may be disposed at positions coincident with the strain-sensitive component, including in the functional layer. For example, portions of the encapsulating material and/or the intermediate layer material may be interspersed with the strain-sensitive component, including at positions within the functional layer.

In an example, a system, apparatus and method herein can be used to detect and/or quantify an amount of contact between an inflatable body and a tissue lumen. The locations and/or degree of contact between the inflatable body and the tissue lumen can be determined based on a measurement of one or more of the sensing elements and/or the electrodes described herein. In an example, the stretchable electronic system described herein can be used to determine a location and/or degree of contact between a tissue lumen and an inflatable body on which the stretchable electronic system is disposed.

As a non-limiting example, a system, apparatus and method herein can be used to detect and/or quantify an amount of contact between an inflatable body and a tissue lumen at different positions of the inflatable body relative to the tissue lumen. In an example, the system, apparatus and method include detecting a degree of contact between select sensing elements or electrodes disposed on the inflatable body and the tissue lumen, and re-positioning the inflatable body to achieve a desired degree of contact between the inflatable body and the tissue lumen. As a non-limiting example, the degree of contact between the inflatable body and a tissue lumen can be used to determine suitability of conditions for administering a therapy, or to determine a degree of occlusion, or to reduce or eliminate the occlusion, including a blockage or closing of a blood vessel or hollow portion of an organ. The system, apparatus and method can be based on an apparatus that includes the flexible substrate forming the inflatable body and the plurality of sensing elements disposed on the flexible substrate, or a stretchable electronic system that includes a flexible annular interconnect and a plurality of electrodes coupled to the flexible annular interconnect, where the stretchable electronic system is disposed on an inflatable body.

In an example, a system, apparatus and method herein can be used to administer a type of therapy to tissue during a medical diagnosis and/or treatment. The system, apparatus and method can be based on an apparatus that includes the flexible substrate forming the inflatable body and the plurality of sensing elements disposed on the flexible substrate, or a stretchable electronic system that includes a flexible annular interconnect and a plurality of electrodes coupled to the flexible annular interconnect, where the stretchable electronic system is disposed on an inflatable body. For example, any of the inflatable bodies described herein may be disposed near a distal portion of a catheter, and a type of therapy may be introduced to a region of tissue during the medical diagnosis and/or treatment. In an example, the type of therapy may be introduced through a shaft of the catheter. In an example, the therapy may be an ablative therapy and/or a drug administration. Non-limiting examples of ablative therapy include cryo-ablation, laser ablation, and high intensity ultrasound.

An example method of performing a medical diagnosis and/or treatment on a tissue includes disposing in proximity to the tissue an apparatus that includes a flexible substrate forming an inflatable body, a coupling bus, and a plurality of sensing elements that are coupled to the coupling bus. The one or more sensing elements of the plurality of sensing elements include contact sensors. The coupling bus is disposed near a distal end of the inflatable substrate, and the plurality of sensing elements are disposed about the inflatable body such that the sensing elements are disposed at areas of minimal curvature of the inflatable body. The method includes recording a measurement of at least one sensing element of the plurality of sensing elements. The measurement provides an indication of a state of a portion of the tissue.

In an example, the measurement can be used to provide an indication of a disease state of the portion of the tissue. In another example, the measurement can be used to provide an indication of a contact state of the portion of the tissue with the at least one sensing element of the plurality of sensing elements.

An example instrument and user interface is also described herein that can be used to display a representation of measurements of a plurality of sensing elements or electrodes that are positioned proximate to a tissue lumen. In an example, a instrument and user interface described herein also can be used for mapping contact between a plurality of sensing elements or electrodes with a tissue lumen. The measurement or mapping data can be used to provide a representation of a degree of contact between an inflatable body supporting the plurality of sensing elements or electrodes and the tissue lumen. An example instrument and/or user interface can be used with any of the example systems, methods or apparatus described herein.

Example apparatus are also described for displaying a representation of measurements of a plurality of sensing elements disposed about at least a portion of a circumference of an inflatable body during a medical diagnosis and/or treatment of a tissue. In this example, the display apparatus includes a display, a memory storing machine-readable instructions, and one or more processor units to execute the machine-readable instructions. Execution of the machine-readable instructions causes the display to display the representation of the measurements. The representation includes a plurality of first indicators and a plurality of second indicators. Each first indicator corresponds to a sensing element of the plurality of sensing elements that measures a signal below a threshold value. Each second indicator corresponding to a sensing element of the plurality of sensing elements that measures a signal above the threshold value.

In an example, a measurement below the threshold value can be used as an indication that the corresponding sensing element of the plurality of sensing elements is not in contact with the tissue.

In an example, a measurement above the threshold value can be used as an indication that at least a portion of the corresponding sensing element of the plurality of sensing elements is in contact with the tissue.

In an example, a measurement below a first threshold value can be used to indicate a state of "no contact" or "no measurement" for a sensing element. In another example, a measurement above a second threshold value can be used to indicate a state of "contact" or "measurement" for a sensing element. In another example, a measurement between the first threshold value and the second threshold value can be used to indicate a state of "poor contact" or "poor measurement" for a sensing element.

An example apparatus is also described for displaying a representation of measurements of a plurality of sensing elements disposed about at least a portion of a circumference of an inflatable body during a medical diagnosis and/or treatment of a tissue. The display apparatus includes a display, a memory storing machine-readable instructions, and one or more processor units to execute the machine-readable instructions. Execution of the machine-readable instructions causes the display to display the representation of the measurements. The representation can include a plurality of first spatial representations and a plurality of second spatial representations. Each first spatial representation corresponds to a sensing element of the plurality of sensing elements that is disposed at a first latitude of the inflatable body. The latitude can be specified relative to the distal end of the inflatable body. Each second spatial representation corresponds to a sensing element of the plurality of sensing elements that is disposed at a second latitude of the inflatable body that is different from the first latitude, In an example, each of the first spatial representations or each of the second spatial representations displays a first indication if the corresponding sensing element measures a signal above a threshold value. In another example, each of the first spatial representations or each of the second spatial representations displays a second indication if the corresponding sensing element measures a signal below a threshold value.

In an example, a system described herein can be used for mapping contact with a surface. The system includes an inflatable body, plurality of electrodes coupled to the inflatable body, an electronic display electrically coupled to the plurality of electrodes. The electronic display provides a visual reproduction of the spatial location of the plurality of electrodes on the inflatable body. The electronic display also changes a visual attribute of an electrode in the plurality of electrodes in response to a change in an electrical signal produced by the electrode, where the change in the electrical signal can be used to identify a contact condition of the electrode with respect to the surface.

In an example, the visual attribute can be a binary representation or a quantitative representation.

In another example, a stretchable electronic system is described that includes a flexible interconnect, and a plurality of impedance based electrode pairs coupled to the flexible interconnect. The electrode pairs are configured to measure impedance between two electrodes of the electrode pair.

In an example, a method of manufacturing a contact mapping balloon catheter is also described. The example method includes identifying regions of maximum curvature on the balloon of the balloon catheter when the balloon is in a deflated state, and coupling a plurality of electrodes to the balloon such that the plurality of electrodes are positioned outside of the regions of maximum curvature.

The present disclosure also describes various non-limiting example implementations of the stretchable electronic systems, methods and apparatus described herein. In an example, the example systems described herein relate to various stretchable electronic systems and apparatus that couple a catheter that includes an inflatable body with conformal electronics to detect (and in some examples, quantify) an amount of contact between the inflatable body and a tissue lumen. The locations and/or degree of contact between the inflatable body and the tissue lumen can be determined based on a measurement of one or more components of the conformal electronic system and the tissue lumen.

In an example, the catheter can be, but is not limited to, a balloon catheter. In an example, the systems and apparatus described herein can be implemented to guide a user (e.g., a clinician) in the delivery of ablation therapy to the lumen of a subject.

For example, the tissue can be cardiac tissue, and the lumen can be the pulmonary veins of a subject.

In a non-limiting example, the ablation therapy can be performed in connection with the treatment of atrial fibrillation. Balloon catheters, including those configured for cryoablation, and may be used to treat patients afflicted with atrial fibrillation. The balloon may be deployed and positioned at the pulmonary vein, and refrigerant may be delivered thereby for cryotherapy through pulmonary vein isolation. To increase efficacy of cryotherapy, the pulmonary veins may be occluded to substantially reduce the heat sink resulting from blood flow. A degree of occlusion during cryotherapy may be assessed by injecting contrast media through the catheter's central lumen while simultaneously using x-ray imaging to obtain information on the balloon-tissue interface. Example systems and apparatus described herein can be implemented for occlusion assessment, assessment of other medical conditions, and/or assessment of treatment progress, without the employment of contrast media and/or x-ray imaging.

The systems disclosed herein provide sensing feedback to the physician on the degree of contact between an inflatable body and with tissue through the integration of impedance-based contact sensors directly on the surface of the inflatable body.

As described further herein, example results of in a live porcine models demonstrates that systems, apparatus and methods according to the examples herein can be implemented to provide real-time guidance to a user (such as a physician) during use as part of a medical diagnosis and/or treatment. For example, systems, apparatus and methods can be implemented to guide a user on how to adjust the inflatable body to achieve optimal occlusion of a tissue lumen (including the pulmonary vein). A medical diagnostic and/or treatment procedure performed using systems, apparatus and methods of assessing occlusion described herein may be completed without exposing a subject to x-rays.

The present disclosure describe example results that show the utility of contact sensing in connection with medical diagnostic and/or treatment procedures using an inflatable and/or expandable body, including cryoballoon ablation procedures.

Example systems and apparatus disclosed herein permit integration of components, including one or more electrodes, photodiodes, thermistors, micro-LEDs, and/or force sensors, or arrays of electrodes, photodiodes, thermistors, micro-LEDs, and/or force sensors, which may be deployed on flexible substrates. The systems and apparatus according to the principles herein can have a wide range of applications in the medical device industry.

In an example, the sensing elements describe herein can include one or more impedance-based contact sensors. In an application where a system, method or apparatus herein can be used to assess occlusion of a lumen, such as but not limited to an artery or a vein (including the pulmonary vein). The work done in connection with these developments demonstrate examples of a novel and practical approach for integrating conformal sensors and associated circuitry on an inflatable surface, including the balloon of a cryoablation balloon and other related medical devices.

An example therapy based on cryothermal energy represents an alternative ablation therapy to radio frequency (RF) energy for treating certain conditions, including cardiac arrhythmias. A cryoballoon system is capable of delivering cryothermal energy through the transition of nitrous oxide from liquid to gaseous phase. In this example implementation, the transition of nitrous oxide from liquid to gaseous phase may be caused by an increase in pressure and a concomitant decrease in temperature to −50° C. during the cryoablative procedure. The pulmonary vein ostium may be the structural target for ablation in paroxysmal AF patients. Achieving occlusion near the antrum of the pulmonary veins assists with achieving effective lesion formation with cryoballoons.

Contiguous, permanent lesions may be formed when the pulmonary veins are all circumferentially occluded by the cryoballoon. Blood flow due to small gaps between the balloon surface and a PV can cause local heating during cryoablation and could give rise to poor lesion formation. To assess good occlusion, contrast dye may be injected through the guide-wire lumen and x-ray imaging may be used to visualize the flow of dye passing along the balloon. The limitations of contrast dye injection include poor image resolution to identify the exact location of the leaks in 3D space. Moreover, exposure to x-ray and ionizable contrast agents pose health risks to patients.

Examples of inflatable bodies are described herein relative to a type of balloon catheter. However, the inflatable bodies applicable to the systems, methods and apparatus herein as not so limited. It is to be understood that the principles herein apply to any type of inflatable body (including an expandable body) on which stretchable electronic systems described herein can be disposed.

FIG. 1 illustrates an example use of a system or apparatus herein for an incomplete occlusion of the tissue lumen 102 (e.g., ostium or pulmonary vein) by an inflatable body (here it is catheter balloon 104) positioned near a distal end of a catheter, according to the principles described herein. The example catheter balloon 104 shown in FIG. 1 has an "onion" shape described herein. The example catheter of FIG. 1 includes a shaft 106. In an example, an ablative therapy can be introduced through shaft 106. According to the principles herein, the plurality of sensing elements, the coupling bus, and/or the stretchable electronic system that includes the flexible annular interconnect and the plurality of electrodes can be disposed about the catheter balloon 104.

The plurality of sensing elements and/or the plurality of electrodes described herein can be formed as sets of nano-membrane sensors and conformal electronics that can be used to perform a medical diagnosis and/or treatment as described herein. That is, the plurality of sensing elements and/or the plurality of electrodes described herein can be disposed on the inflatable body (here catheter balloon 104 of FIG. 1) without substantially changing the mechanics and/or thermal profiles of the inflatable body.

In an example, the creation and implementation of highly conformal arrays of impedance-based contact sensors on balloon catheters are described herein. Various examples of the systems herein include arrays of bipolar electrodes that are configured in a circumferential orientation on the balloon surface. The use of sensor arrays on an inflatable body as described herein can be used to provide an insight into localized mechanical interactions of the inflatable body and tissue, which can be poorly visualized with point sensing techniques. A system according to the principles herein can provide for high sensitivity contact sensing and provide insight into occlusion, thermal interactions, and gap localization on the inflatable body (e.g., a cryoballoon).

A pressure sensor that measures pulmonary vein pressure can be introduced into a lumen prior to and following occlusion. Changes in pressure caused by occlusion can be assessed. This approach may not facilitate assessing localized activity at different quadrants of the inflatable body (e.g., the catheter balloon) that align with the anatomy of the lumen.

The systems, methods and apparatus described herein provide design strategies and fabrication techniques to achieve high performance stretchable electronics systems that are also flexible and that can be seamlessly integrated with inflatable bodies. The stretchable electronics systems can include the plurality of sensing elements, the coupling bus, the flexible annular interconnect and/or the plurality of electrodes. The stretchable electronics systems can be fabricated using inorganic semiconductor processes.

In an example, the sensing elements, the coupling bus, and/or the stretchable electronic system that includes the flexible annular interconnect and the plurality of electrodes may be fabricated on a rigid and/or brittle substrate and then applied to the surface of the inflatable body. That is, various forms of high performance electronics may be fabricated on the rigid and brittle surfaces of semiconductor wafers or metallic wires in formats that are inherently low density may be incompatible with establishing intimate physical coupling with the complex topologies of the atria and ventricles due to their rigidity. Various electronic systems may be further limited by their inability to offer simple modes of functionality that do not allow real-time mapping over multiple sensor nodes. The systems, methods and apparatus described herein provide technology to integrate thin, conformal arrays of sensory electronics on inflatable bodies, including deformable substrates such as silicone or polyurethane balloon skins. The integrated systems and apparatus described herein permit electrical, thermal, and chemical sensing components to be implemented on the surface of inflatable bodies.

Figure 2A:
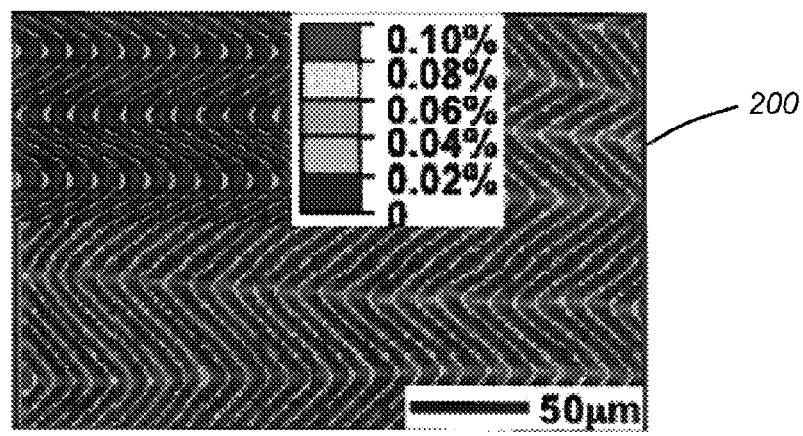
FIGS. 2A-2C show example scanning electron microscope images with different stretchable design according to the principles described herein.
Figure 2B:
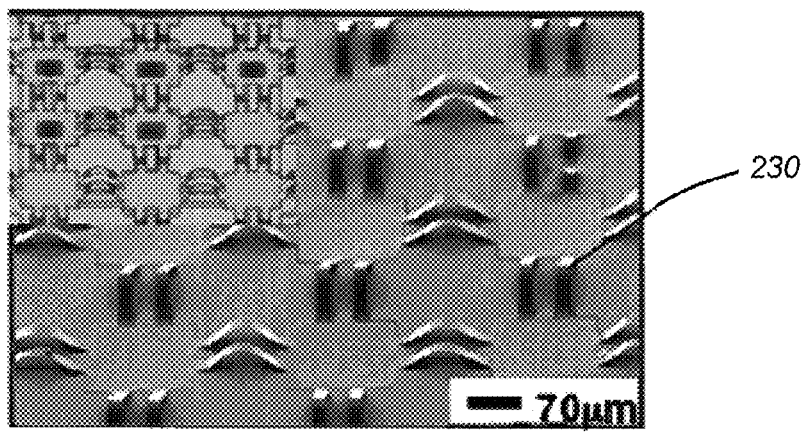
Figure 2C:
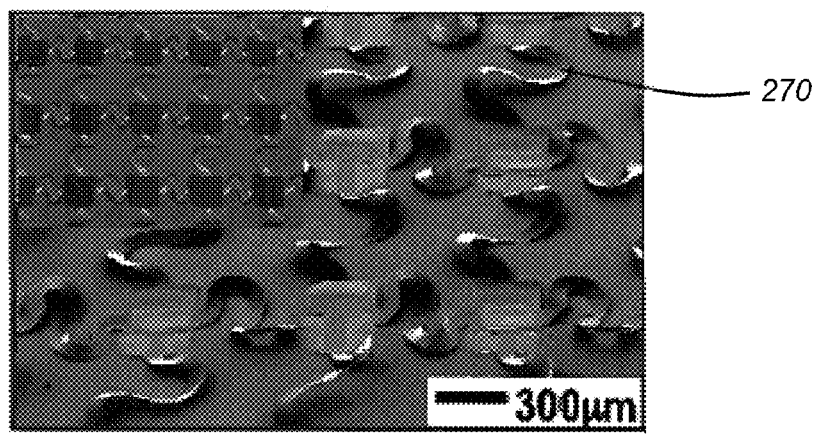

In an example, the sensing elements, the coupling bus, and/or the stretchable electronic system that includes the flexible annular interconnect and the plurality of electrodes can be formed using the ultrathin designs of inorganic nanomaterials. These ultrathin designs permit implementation of flexible electronics over very small bending radii, for example less than 100 microns. However, extreme bending and stretching conditions may induce greater strains or fractures in a material, such as in instances where these electronics interface with soft tissue lumen (including soft tissues of the heart). For example, electronics on the heart can undergo large strains up to 10-20% or more. Sensors and electrodes on inflatable bodies for minimally invasive procedures may be subjected to even higher mechanical strain, exceeding 100% strains in some instances. To alleviate the strains induced in these situations, various forms of flexible nanomaterials may be implemented, and may include serpentine layouts or buckled structures. FIGS. 2A-2C show scanning electron microscope images and corresponding finite element modeling (FEM) results (inset) of stretchable nanomaterials/devices with different stretchable designs. FIG. 2A shows a 2D herringbone structure 200 that can be used to form interconnect. When the substrate of the herringbone structure 200 is stretched, the herringbone structure flattens to accommodate the stretching. FIGS. 2B and 2C show alternative structures that include selectively bonded device island regions with interconnects that are coupled to the device islands, and physically separated from the substrate at regions between the device islands. Such interconnects can further enhance stretching. The interconnect structures of FIG. 2B appear as non-co-planar pop-up interconnect structures 230, also referred to as buckled structures. The interconnect structures of FIG. 2C appear as serpentine interconnect structures 270.

Stretchability of over 200% of the stretchable electronics systems may be accomplished with non-coplanar serpentine-shaped interconnects. Device islands or electrodes may be coupled to a flexible substrate of an inflatable body via covalent bonding. Serpentine interconnects may be loosely coupled through van der Waals forces. Therefore, subjecting the substrate to deformation may cause the metal interconnects, such as but not limited to the serpentine interconnects, to detach from the underlying substrate thereby relieving stress from the device islands. As a result, the maximum principal strain exerted on the interconnects can be reduced by two orders of magnitude compared to the strain applied to the underlying substrate.

Figure 3A:
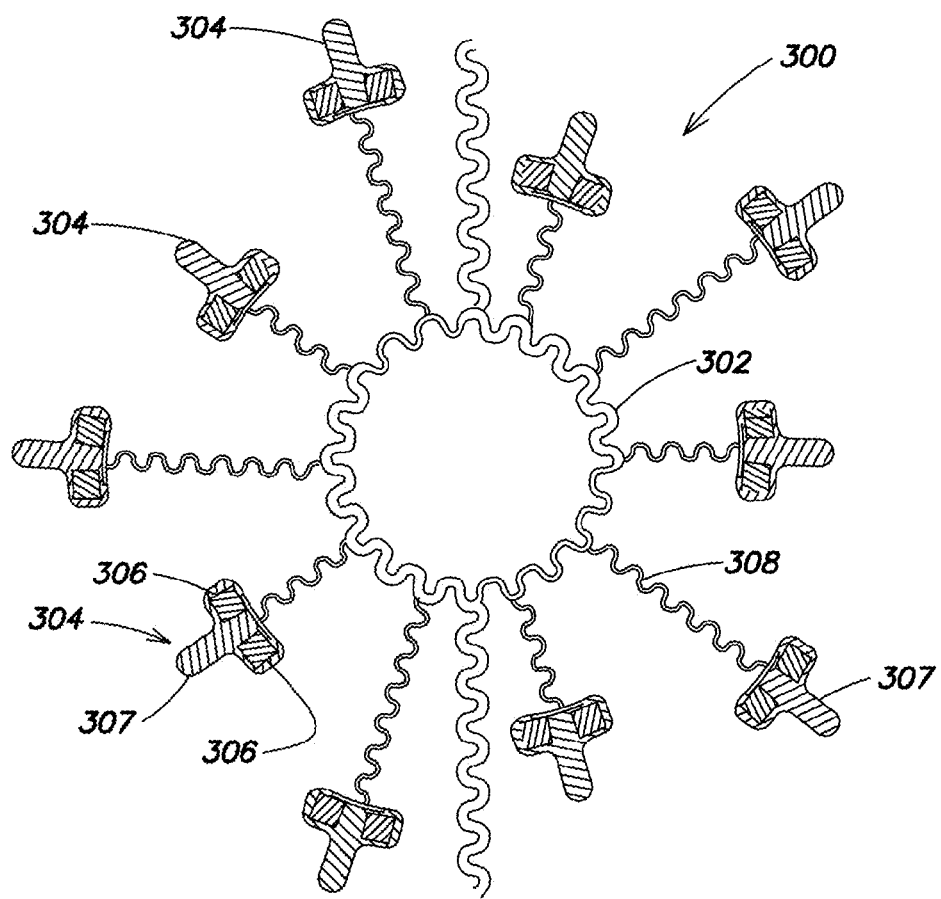
FIGS. 3A and 3B illustrate an example of a stretchable electronic system according to the principles described herein.
Figure 3B:
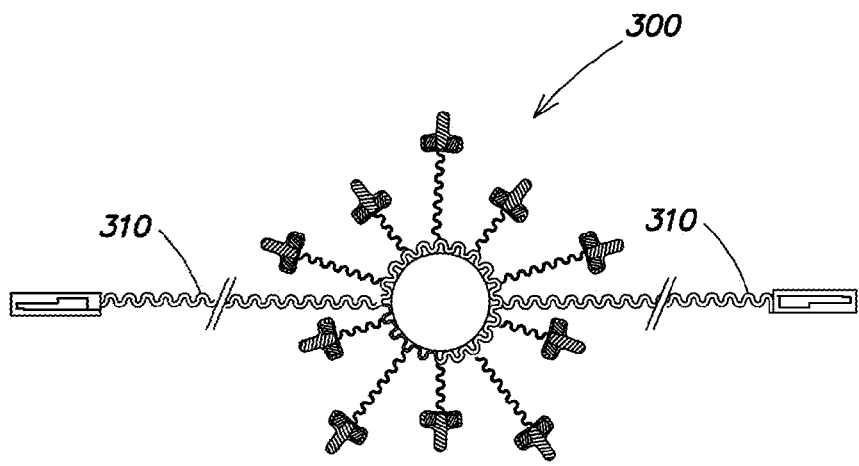

FIGS. 3A and B illustrate an example of a stretchable electronic system 300 that includes a coupling bus 302 and a number of sensing elements 304. The stretchable electronic structure 300 can be coupled to an inflatable body according to the principles described herein. As shown in FIG. 3A, the sensing elements can be configured to include bipole electrodes 306. In the example configuration illustrated in FIG. 3A, there are 10 bipolar electrodes. However, other examples can include more or fewer sensing elements 304. In the example of FIGS. 3A and 3B, the sensing elements are formed with the bipole electrodes 306 disposed on and/or surrounded by pads 307. In an example, the pads are formed from a polymer, such as but not limited to a polyimide. Each sensing element 304 is coupled to the coupling bus 302 via a coupling interconnect 308.

In the example of FIG. 3A, the sensing elements include bipole electrodes 306 that have substantially a square shape and the pads 307 have a shape that extends substantially beyond the bipole electrodes 306. In other example, the bipole electrodes 306 can have rectangular, circular or other polygonal shape and the pads 907 may not extend beyond the bipole electrodes 906.

FIG. 3B shows a wider view of the example stretchable electronic system 300 of FIG. 3A, and shows the intermediate bus that can be used to couple the sensing elements to a circuit to provide power to and/or collect measurements from, e.g., the sensing elements 304. The intermediate bus and coupling interconnect in this any other example described herein can be formed from any suitable conductive material, including conductive materials described hereinabove.

As shown in FIG. 3A, the coupling bus 302 may have a non-uniform distribution about the loop structure. For example, portions of the coupling bus 302 that lead into the intermediate bus 310 are thicker than other portions of coupling bus 302.

Figure 4A:
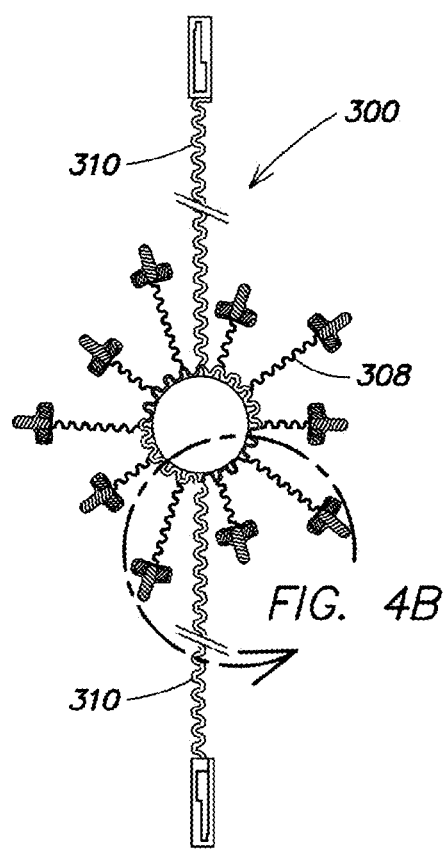
FIGS. 4A-4C show views of portions of the example stretchable electronic system FIGS. 3A, 3B according to the principles described herein.
Figure 4B:
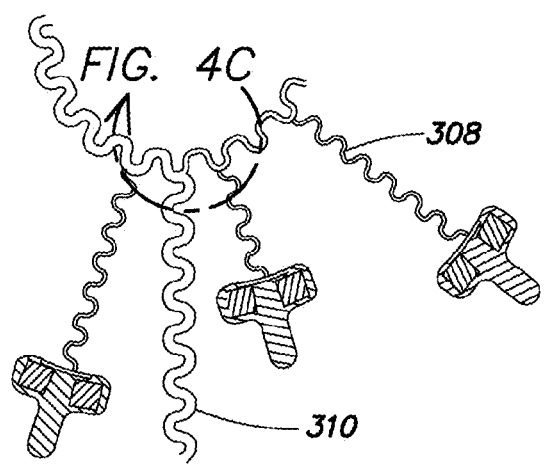
Figure 4C:
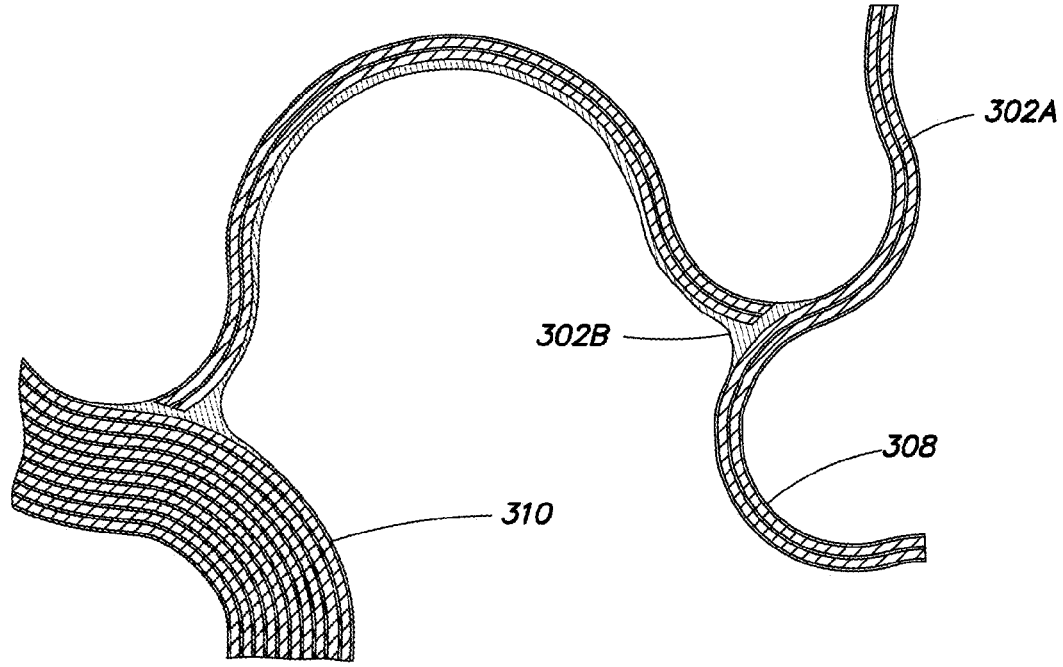

FIGS. 4B-C show magnified views of portions of the example stretchable electronic system 300 of FIGS. 3A, 3B and 4A. As shown in FIGS. 4B and 4C, the intermediate bus 310 is thicker than the coupling interconnect 308. FIG. 4C also shows the lines of conductive structures that form the intermediate bus 310 and the coupling interconnect 308. As also shown in FIG. 4B, the coupling bus 302 can be formed in a serpentine (undulating) geometry. As also shown in FIG. 4C, coupling bus 302 can include conductive portions 302A and non-conductive portions 302B, which can be formed from the materials described hereinabove.

Figure 5A:
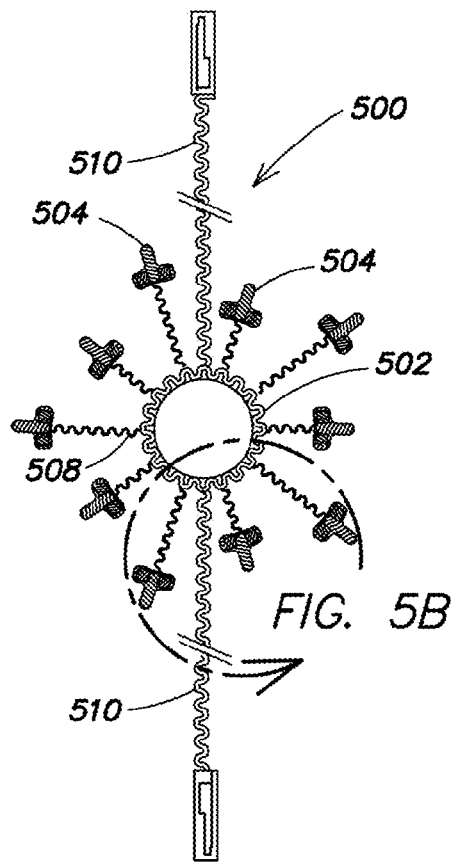
FIGS. 5A-5D illustrates an example of a stretchable electronic system according to the principles described herein.
Figure 5B:
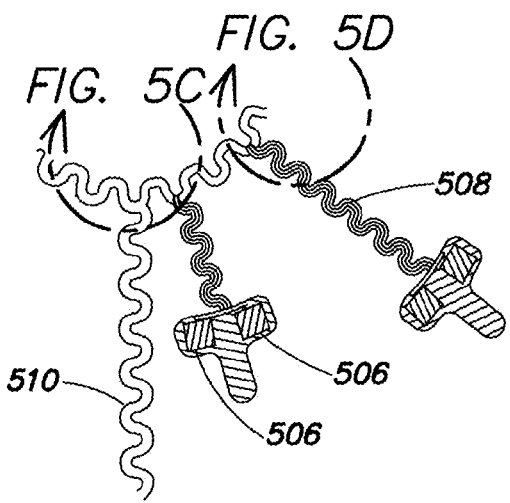
Figure 5C:
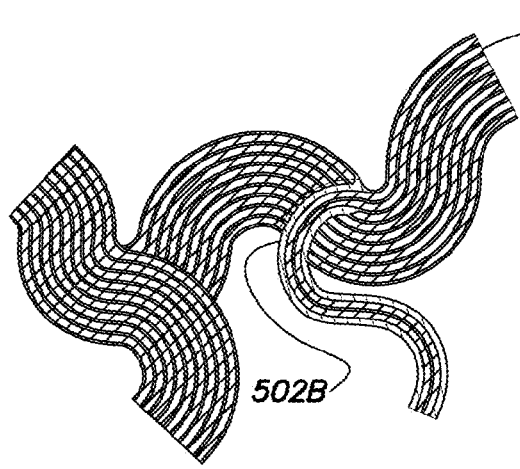
Figure 5D:
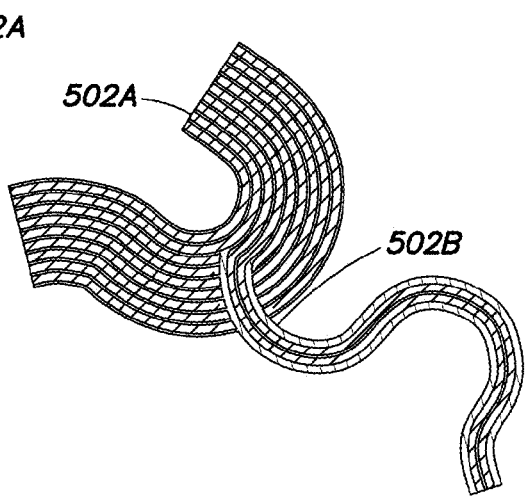

FIG. 5A illustrates an example of a stretchable electronic system 500 that includes a coupling bus 502 and a number of sensing elements 504. FIGS. 5B-D show magnified views of portions of the example stretchable electronic system 500 of FIG. 5A. The stretchable electronic structure 500 can be coupled to an inflatable body according to the principles described herein. As shown in FIG. 5B, the sensing elements can be configured to include bipole electrodes 506. In the example configuration illustrated in FIG. 5A, there are 10 bipolar electrodes. However, other examples can include more or fewer sensing elements 504. In the example of FIGS. 5A and 5B, the sensing elements are formed with the bipole electrodes 506 disposed on and/or surrounded by pads. In an example, the pads are formed from a polymer, such as but not limited to a polyimide. Each sensing element 504 is coupled to the coupling bus 502 via a coupling interconnect 508.

FIG. 5A shows the intermediate bus 510 that can be used to couple the sensing elements to a circuit to provide power to and/or collect measurements from, e.g., the sensing elements 504

FIG. 5B shows a magnified view of the example stretchable electronic system 500 of FIG. 5A, and shows the intermediate bus 510 and coupling interconnect 508. The intermediate bus 510 and coupling interconnect 508 in this any other example described herein can be formed from any suitable conductive material, including conductive materials described hereinabove.

As shown in FIG. 5A, the coupling bus 502 may have a substantially uniform distribution about the loop structure. For example, portions of the coupling bus 502 that lead into the intermediate bus 510 are of substantially similar thickness as other portions of coupling bus 502.

FIGS. 5C-D show magnified views of portions of the example stretchable electronic system 500. FIG. 5C also shows the lines of conductive structures that form the intermediate bus 510 and the coupling interconnect 508. As also shown in FIG. 5C, the coupling bus 502 can be formed in a serpentine (undulating) geometry. As also shown in FIGS. 5C and 5D, coupling bus 502 can include conductive portions 502A and non-conductive portions 502B, which can be formed from the materials described hereinabove.

Figure 6:
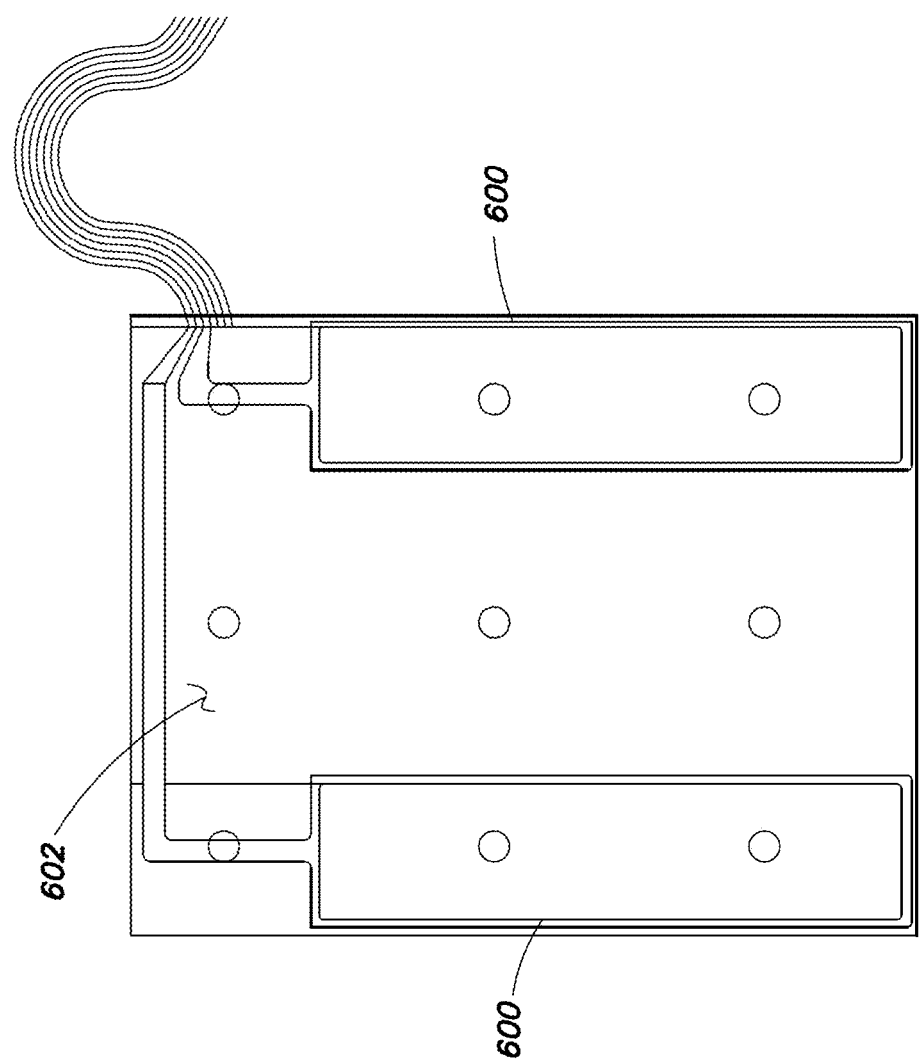
FIG. 6 illustrates an example pair of sensors with polyimide on the backplane and serpentine interconnects branching from the sensors according to the principles described herein.

FIG. 6 illustrates a pair of sensors (rectangles) 600 attached to an underlying polyimide layer 602 (a polyimide pad). The polyimide layer in this example may not be stretchable, thereby allowing the distance separating the pair sensors 600 to remain substantially constant even during inflation of the inflatable body. This substantially constant gap size between the sensor pairs helps reducing signal fluctuations during inflation deflation and deformations of the inflatable body.

Figure 7:
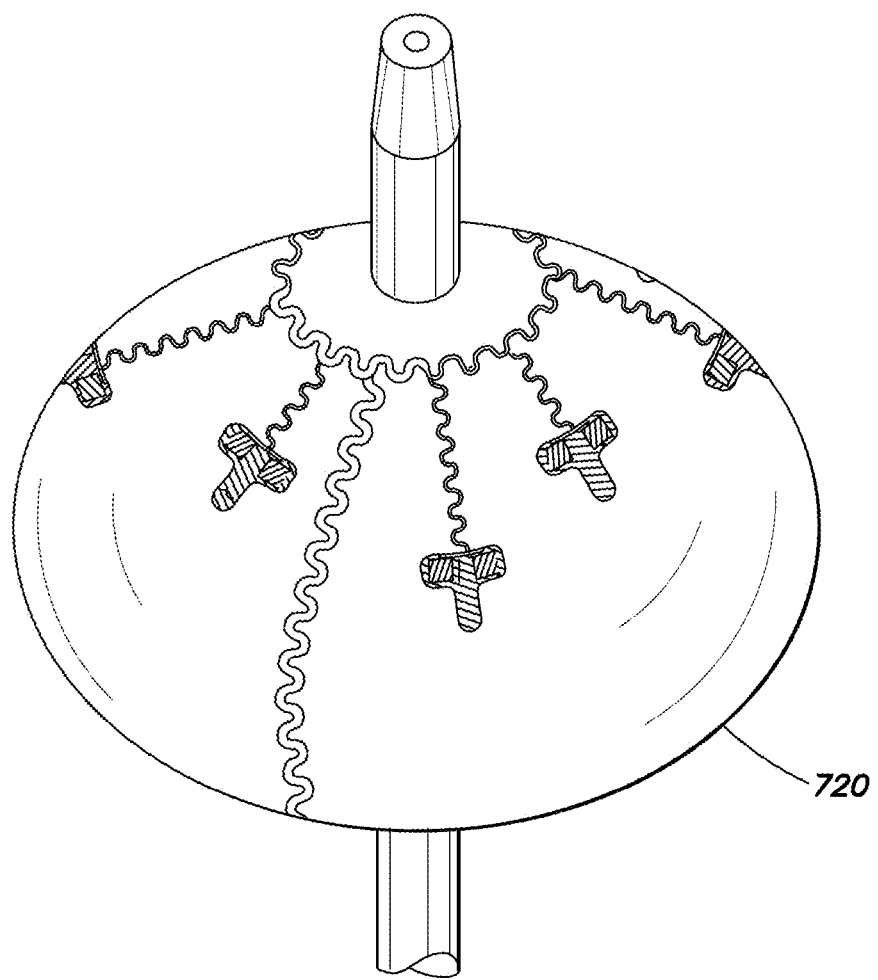
FIG. 7 shows the stretchable electronic system according to the principles of FIGS. 3A-B, disposed on an example inflatable body according to the principles described herein.
Figure 8:
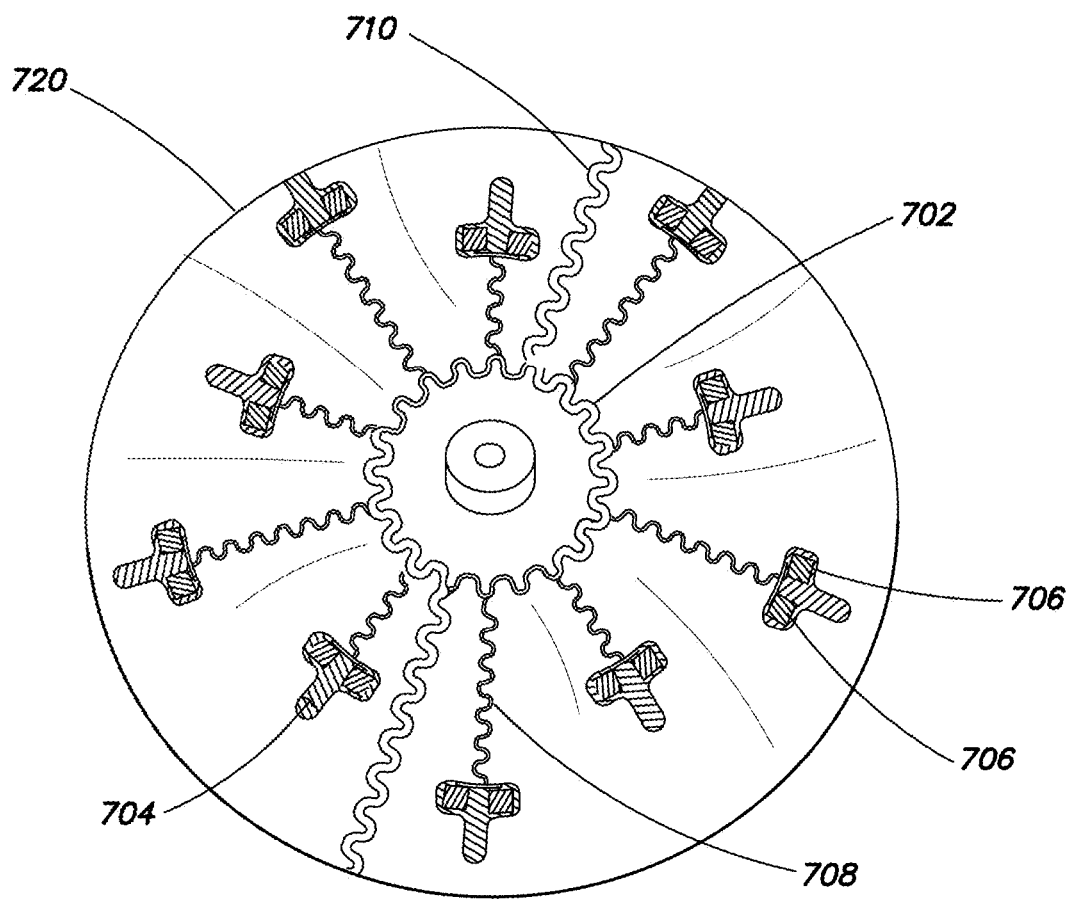
FIG. 8 is a magnified view of the example balloon catheter of FIG. 7 according to the principles described herein.

FIG. 7 shows the stretchable electronic system according to the principles of FIGS. 3A-B, disposed on an inflatable body 720. In this example, the inflatable body 720 is a balloon catheter. FIG. 8 is a magnified view of the balloon catheter of FIG. 7. The stretchable electronic system includes coupling bus 702, sensing elements 704, and coupling interconnects 708 and intermediate bus 710. The sensing element 704 includes bipole electrodes 706. To test the ability of contact sensors on a balloon to verify occlusion, an array 10 bipolar of electrodes is implemented on an inflatable body to evaluate contact with pulmonary vein tissue relative to that of blood. Impedance of tissue is approximately 1.5-2× higher than that of blood. Therefore, in an example, contact between the inflatable body and the sensing elements can be determined based on impedance measurements using the bipole electrodes. Based on insight into the placement of the inflatable body of FIG. 7 in the pulmonary veins, it is determined that the distal pole of the balloon is most likely to contact tissue. Therefore, sensing elements can be strategically distributed about the inflatable body to be near points of potential contact. In an example system, the points for placement of the sensing elements can be determined as specific latitudes or circumferences of the inflatable body.

Figure 12C:
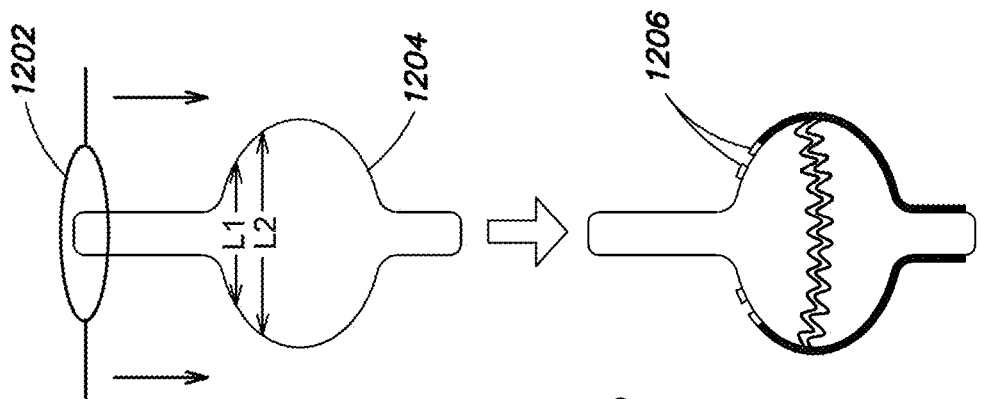
FIGS. 12A-12C illustrate the assembly of an example stretchable electronic system, according to the principles described herein.
Figure 12B:
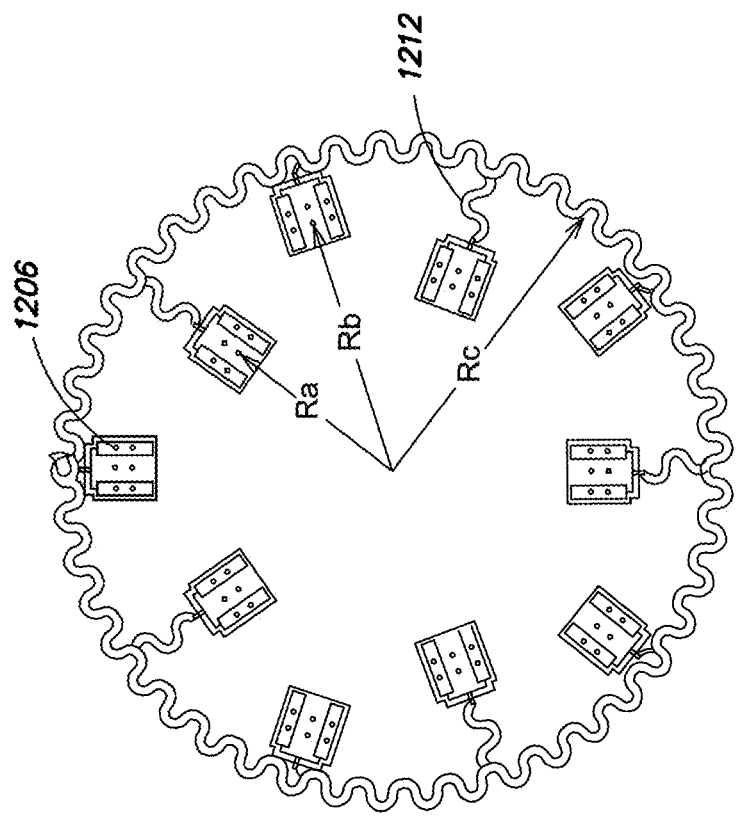
Figure 12A:
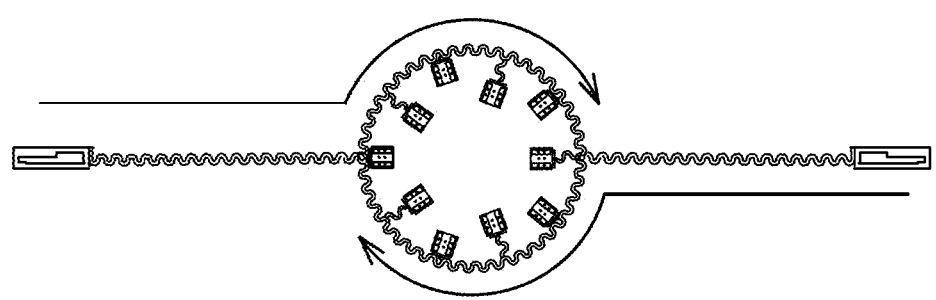
Figure 14A:
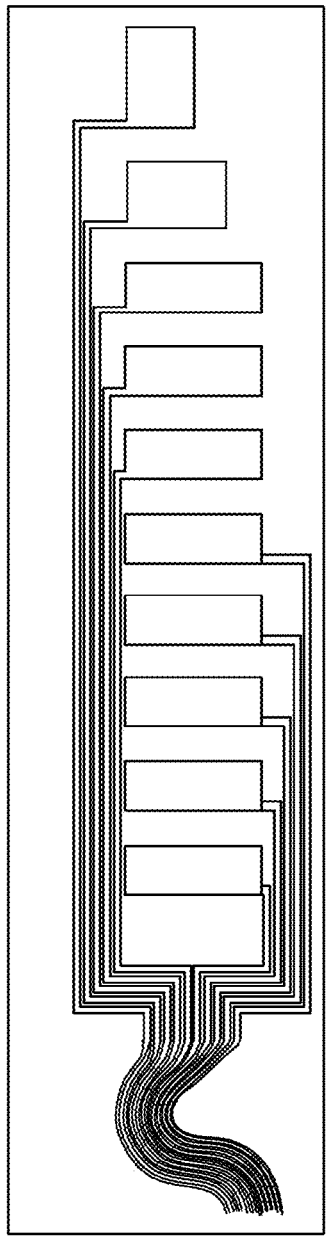
FIGS. 14A-14B show example application of a metallization layer of a stretchable electronic system, according to the principles described herein.
Figure 14B:
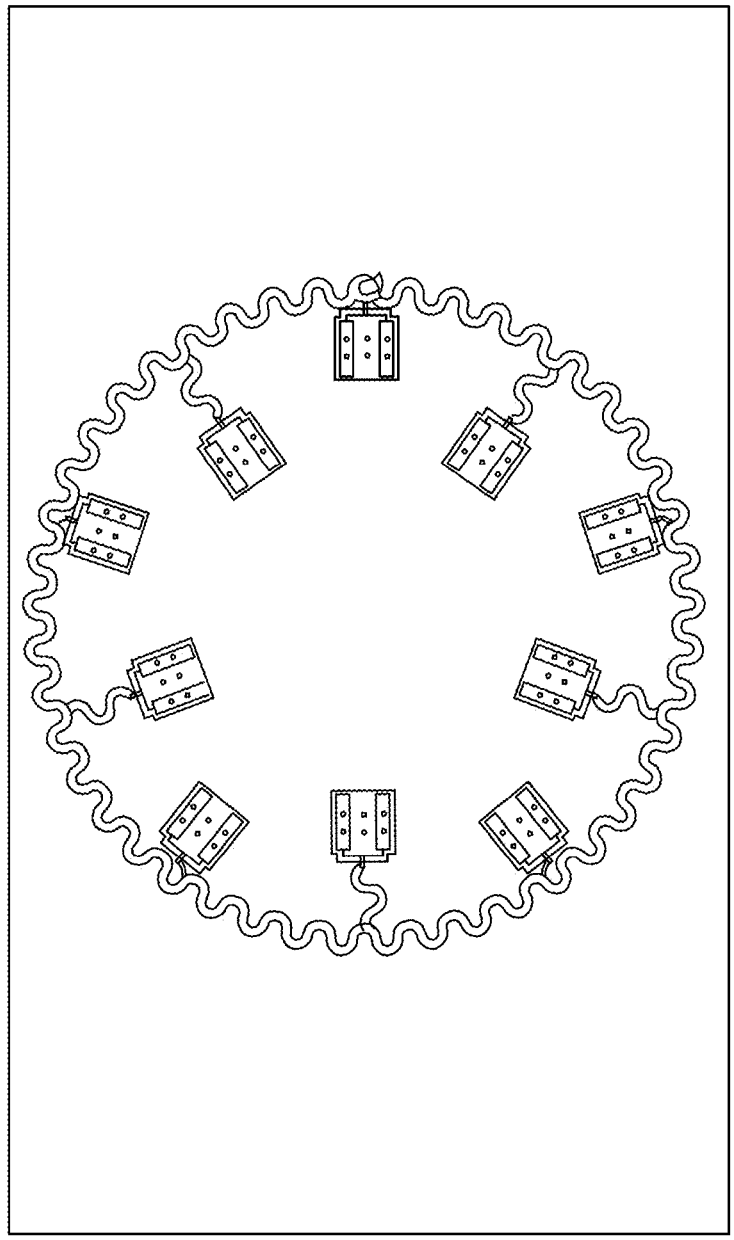

In a non-limiting example where the inflatable body is an ARCTIC FRONT® Cryoballoon Catheter (available from Medtronic Inc, Minneapolis, Minn.) balloon, the sensing elements can be positioned at about the 15 mm and about the 20 mm diameter portions of the cryoballoon (as described in greater detail in FIGS. 12A-12C). In this non-limiting example, the radius ($R_A$) of the coupling bus 1206 is around 12 mm, a first set of the sensing elements extend from the coupling bus 1206 to fall along a circle of a radius ($R_B$) of about 10 mm, and a second set of the sensing elements extend from the coupling bus 1206 to fall along a circle of a radius ($R_C$) of about 7.5 mm. The density of sensing elements facilitate identification of spatial gaps in occlusion between the inflatable body and target lumen.

FIGS. 9-11 illustrate additional examples of stretchable electronic system according to the principles described herein. While the examples illustrated in FIGS. 3A-5D and 9-11 include 10 distributed sensing elements, other examples may be implemented that include more or fewer sensing elements. The sensing elements may be distributed in a manner distinct from that illustrated in FIGS. 3A-5D and 9-11. In an example, the sensing elements are contact sensors.

Figure 9A:
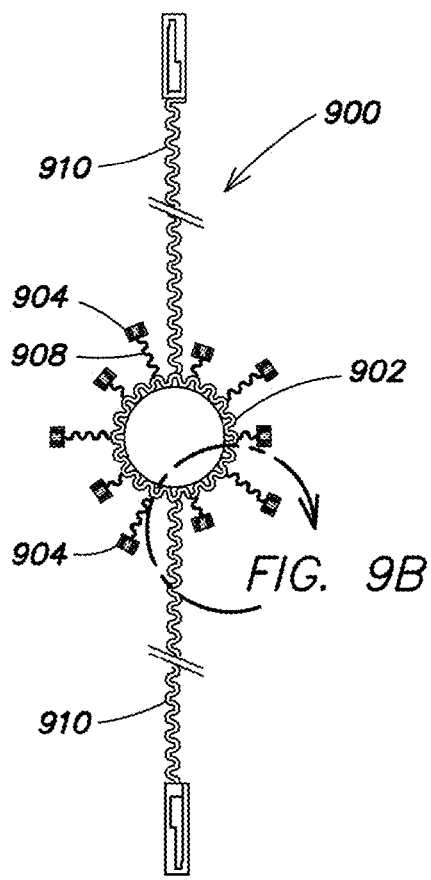
FIGS. 9A-9D illustrate an example of a stretchable electronic system, according to the principles described herein.
Figure 9B:
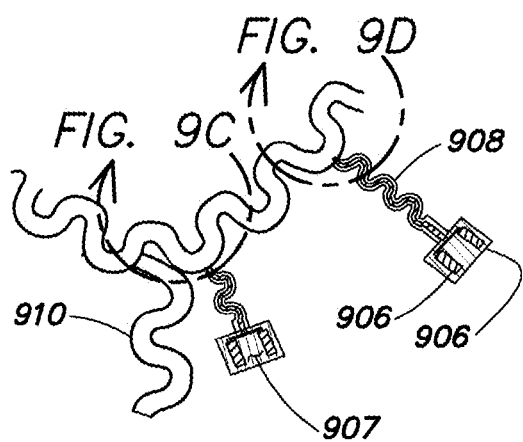
Figure 9C:
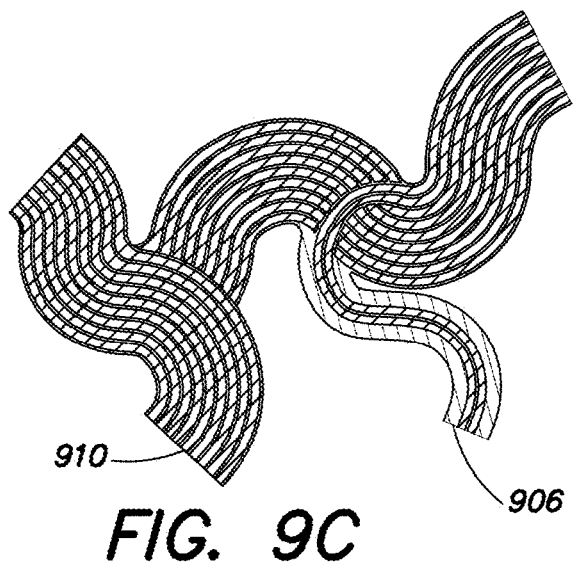
Figure 9D:
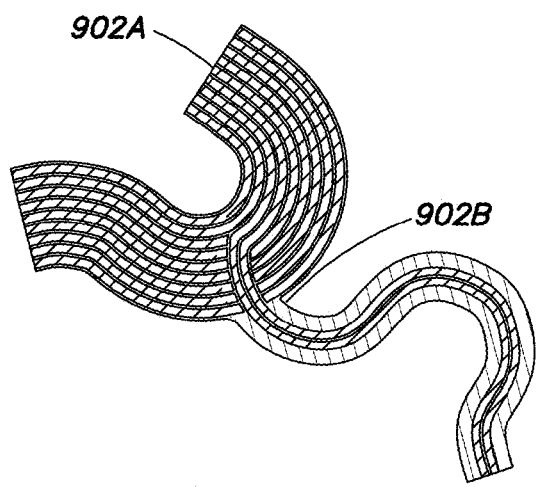

FIG. 9A illustrates an example of a stretchable electronic system 900 that includes a coupling bus 902 and a number of sensing elements 904. FIGS. 9B-D show magnified views of portions of the example stretchable electronic system 900 of FIG. 9A. The stretchable electronic structure 900 can be coupled to an inflatable body according to the principles described herein. As shown in FIG. 9B, the sensing elements can be configured to include bipole electrodes 906. In the example configuration illustrated in FIG. 9A, there are 10 bipolar electrodes. However, other examples can include more or fewer sensing elements 904. In the example of FIGS. 9A and 9B, the sensing elements are formed with the bipole electrodes 906 disposed on and/or surrounded by pads 907. The morphology of the pads of the system of FIG. 9A-D are different from the pads of the pads of the system of FIG. 3A-D. In addition, the dimension of the sensing elements 904 relative to the size of the coupling bus 902 are smaller than those in the example of FIG. 3A-C or FIG. 5A-D. In an example, the pads are formed from a polymer, such as but not limited to a polyimide. Each sensing element 904 is coupled to the coupling bus 902 via a coupling interconnect 908.

In the example of FIG. 9B, the sensing elements include bipole electrodes 906 that have substantially a rectangular shape and the pads 907 have a shape that encompasses the bipole electrodes 906. In other example, the bipole electrodes 906 can have square, circular or other polygonal shape, and the pads 907 can extend beyond the bipole electrodes 906.

FIG. 9A shows the intermediate bus 910 that can be used to couple the sensing elements to a circuit to provide power to and/or collect measurements from, e.g., the sensing elements 904

FIG. 9B shows a magnified view of the example stretchable electronic system 900 of FIG. 9A, and shows the intermediate bus 910 and coupling interconnect 908. The intermediate bus 910 and coupling interconnect 908 in this any other example described herein can be formed from any suitable conductive material, including conductive materials described hereinabove.

As shown in FIG. 9A, the coupling bus 902 may have a substantially uniform distribution about the loop structure. For example, portions of the coupling bus 902 that lead into the intermediate bus 910 are of substantially similar thickness as other portions of coupling bus 902.

FIGS. 9C-D show magnified views of portions of the example stretchable electronic system 900. FIG. 9C also shows the lines of conductive structures that form the intermediate bus 910 and the coupling interconnect 908. As also shown in FIG. 9C, the coupling bus 902 can be formed in a serpentine (undulating) geometry. As also shown in FIGS. 9C and 9D, coupling bus 902 can include conductive portions 902A and non-conductive portions 902B, which can be formed from the materials described hereinabove.

Figure 10A:
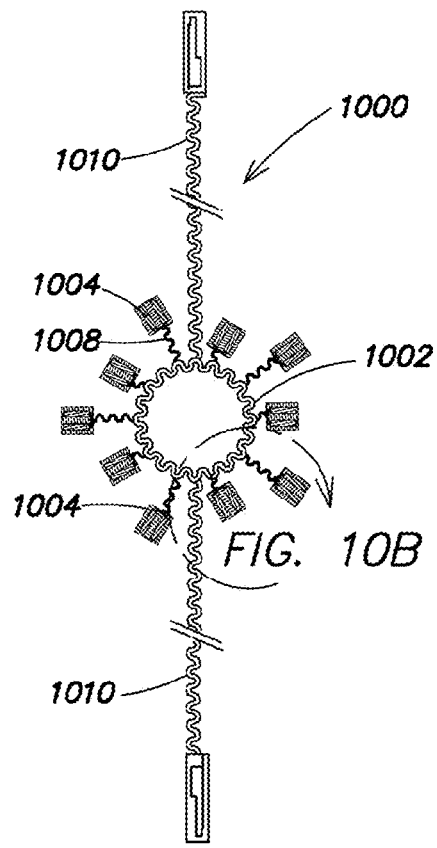
FIGS. 10A-10D illustrate an example of a stretchable electronic system, according to the principles described herein.
Figure 10B:
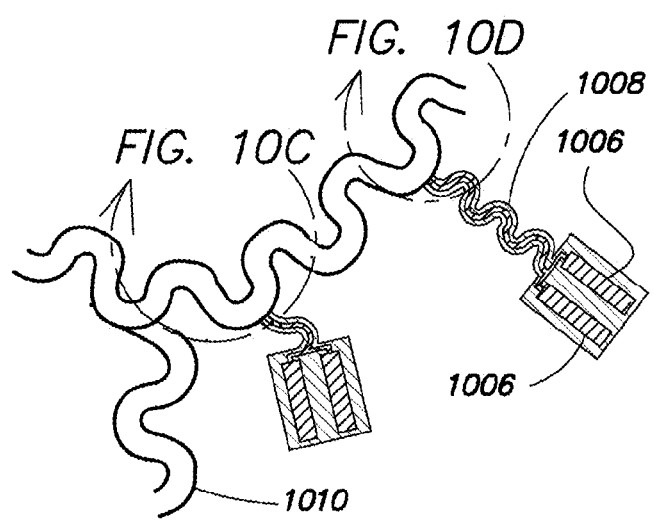
Figure 10C:
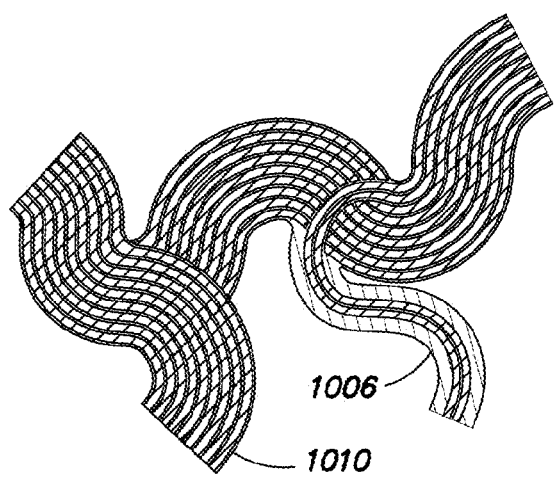
Figure 10D:
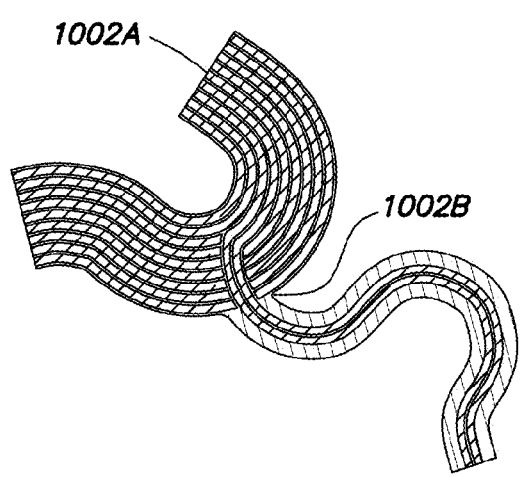

FIG. 10A illustrates an example of a stretchable electronic system 1000 that includes a coupling bus 1002 and a number of sensing elements 1004. FIGS. 10B-D show magnified views of portions of the example stretchable electronic system 1000 of FIG. 10A. The stretchable electronic structure 1000 can be coupled to an inflatable body according to the principles described herein. As shown in FIG. 10B, the sensing elements can be configured to include bipole electrodes 1006. In the example configuration illustrated in FIG. 10A, there are 10 bipolar electrodes. However, other examples can include more or fewer sensing elements 1004. In the example of FIGS. 10A and 10B, the sensing elements are formed with the bipole electrodes 1006 disposed on and/or surrounded by pads. The morphology of the pads of the system of FIG. 10A-D are different from the pads of the pads of the system of FIG. 3A-D. In addition, the dimension of the sensing elements 1004 relative to the size of the coupling bus 1002 are larger than those in the example of FIG. 3A-C or FIG. 5A-D. In an example, the pads are formed from a polymer, such as but not limited to a polyimide. Each sensing element 1004 is coupled to the coupling bus 1002 via a coupling interconnect 1008.

FIG. 10A shows the intermediate bus 1010 that can be used to couple the sensing elements to a circuit to provide power to and/or collect measurements from, e.g., the sensing elements 1004

FIG. 10B shows a magnified view of the example stretchable electronic system 1000 of FIG. 10A, and shows the intermediate bus 1010 and coupling interconnect 1008. The intermediate bus 1010 and coupling interconnect 1008 in this any other example described herein can be formed from any suitable conductive material, including conductive materials described hereinabove.

As shown in FIG. 10A, the coupling bus 1002 may have a substantially uniform distribution about the loop structure. For example, portions of the coupling bus 1002 that lead into the intermediate bus 1010 are of substantially similar thickness as other portions of coupling bus 1002.

FIGS. 10C-D show magnified views of portions of the example stretchable electronic system 1000. FIG. 10C also shows the lines of conductive structures that form the intermediate bus 1010 and the coupling interconnect 1008. As also shown in FIG. 10C, the coupling bus 1002 can be formed in a serpentine (undulating) geometry. As also shown in FIGS. 10C and 10D, coupling bus 1002 can include conductive portions 1002A and non-conductive portions 1002B, which can be formed from the materials described hereinabove.

In the example stretchable electronic system of FIGS. 3A-10D, the sensing elements are directed outwards from the coupling bus. For these configurations, the size of the coupling bus may be configured such that it is disposed near a distal portion of an inflatable body, and the sensing elements disposed nearer to mid-portion (for some inflatable bodies, an equator) of the inflatable body. FIGS. 7 and 8 illustrate an example assembly, where the coupling bus 702 is disposed near a distal end of a balloon catheter 720, which the sensing elements 704 are disposed closer to an equator ob the balloon catheter 720. As also shown in FIG. 8, the sensing elements can be disposed at different radii of the catheter balloon such that the sensing elements are disposed at different latitudes relative to the balloon catheter. In another example implementation using the stretchable electronic system according to the principles of FIGS. 3A-5D and 9A-10D, the size of the coupling bus may be configured such that it is disposed near a mid-portion (or equator) of an inflatable body, and the sensing elements are directed towards the center from the coupling bus. When an example stretchable electronic structure according to this example is mounted on an inflatable body, the sensing elements would be directed closer to distal portions of the inflatable body.

FIG. 11A illustrates another example of a stretchable electronic system 1100 that includes a coupling bus 1102 and a number of sensing elements 1104. In this example, the sensing elements 1104 are directed towards the center of the coupling bus 1102. FIGS. 11B-D show magnified views of portions of the example stretchable electronic system 1100 of FIG. 11A. The stretchable electronic structure 1100 can be coupled to an inflatable body according to the principles described herein. As shown in FIG. 11B, the sensing elements can be configured to include bipole electrodes 1106. In the example configuration illustrated in FIG. 11A, there are 10 bipolar electrodes. However, other examples can include more or fewer sensing elements 1104. In the example of FIGS. 11A and 11B, the sensing elements are formed with the bipole electrodes 1106 disposed on and/or surrounded by pads. The morphology of the pads of the system of FIG. 11A-D are different from the pads of the pads of the system of FIG. 3A-D. In addition, the dimension of the sensing elements 1104 relative to the size of the coupling bus 1102 are larger than those in the example of FIG. 3A-C or FIG. 5A-D. In an example, the pads are formed from a polymer, such as but not limited to a polyimide. Each sensing element 1104 is coupled to the coupling bus 1102 via a coupling interconnect 1108.

FIG. 11A shows the intermediate bus 1110 that can be used to couple the sensing elements to a circuit to provide power to and/or collect measurements from, e.g., the sensing elements 1104

FIG. 11B shows a magnified view of the example stretchable electronic system 1100 of FIG. 11A, and shows the intermediate bus 1110 and coupling interconnect 1108. The intermediate bus 1110 and coupling interconnect 1108 in this any other example described herein can be formed from any suitable conductive material, including conductive materials described hereinabove.

As shown in FIG. 11A, the coupling bus 1102 may have a substantially uniform distribution about the loop structure. For example, portions of the coupling bus 1102 that lead into the intermediate bus 1110 are of substantially similar thickness as other portions of coupling bus 1102.

FIGS. 11C-D show magnified views of portions of the example stretchable electronic system 1100. FIG. 11C also shows the lines of conductive structures that form the intermediate bus 1110 and the coupling interconnect 1108. As also shown in FIG. 11C, the coupling bus 1102 can be formed in a serpentine (undulating) geometry. As also shown in FIGS. 11C and 11D, coupling bus 1102 can include conductive portions 1102A and non-conductive portions 1102B, which can be formed from the materials described hereinabove.

An interconnect having a serpentine structure as described herein allows for stretching and compression of the system, ensuring survival of the sensing elements during deployment through a sheath. In an example implementation, the sensing elements can be each about 1 mm$^2$ in total area, to achieve sufficient contact with tissue. These configurations of the stretchable electronic system also employ coupling buses or annular interconnects at or near the distal end of the inflatable body. In the configurations provided in FIGS. 3A-5D and 9A-10D, the coupling buses or annular interconnects is positioned at smaller radius than the sensing elements. In the example configuration illustrated in FIG. 11A-D, the serpentine ring is positioned at a larger radius than the sensors. The coupling buses or annular interconnects can be used as a landmark for steady alignment during assembly of the coupling buses or annular interconnects with the inflatable body. The configuration of FIG. 4A-C appeared to exhibit the greatest resistance to delamination and had a significantly smaller profile and that can be easier to navigate through a sheath compared to the large circular ring incorporated in the configuration of FIG. 11A-D.

FIGS. 12A-12C illustrate the assembly of an example stretchable electronic system 1202 (shown in FIGS. 12A and 12B) with an inflatable body 1204. In the example of FIG. 12C, of the stretchable electronic system 1202 is configured such that the coupling bus is disposed near an equator of inflatable body 1204, and the sensing elements 1206 are directed towards closer to distal portions of the inflatable body 1204. The differing radii of extent of the sensing element are configured such that they fall at specified latitudes of the inflatable body 1204. For example, the stretchable electronic system can be configured (based on the differing lengths or differing capacities for stretchability of the flexible interconnect structures 1212) such that a given sensing element 1206 is disposed at latitude L1 or latitude L2 of the inflatable body 1204. FIG. 12C illustrates an assembly process for integrating a stretchable electronic system that includes a substantially circular coupling bus or annular interconnect with an inflatable body 1204. As noted herein, the substantially circular coupling bus or annular interconnect facilitates alignment during integration of the flexible electronic components with the inflatable body 1204.

In an example, using a balloon catheter, the latitude L1 can be positioned at a level of the balloon catheter with a circumference that is about 65% of the circumference of the equator of the balloon, while the latitude L2 can be positioned at with a circumference that is about 87% of the circumference of the equator. The latitude(s) of placement of the sensing elements of a stretchable electronic system on an inflatable body can be determined based on an expected contact point between the inflatable body and a region of a tissue lumen. For example, as shown in FIG. 1A, portions of an inflatable body 104 may be expected to substantially contact portions of a tissue lumen 102. The position of placement of the sensing elements can be determined such that one or more of the sensing elements are positioned proximate to the tissue when the inflatable body is deployed in the tissue lumen. The latitudes (e.g., L1, L2, etc) may be decided based on such expected positioning of the inflatable body relative to the tissue lumen.

Figure 15A:
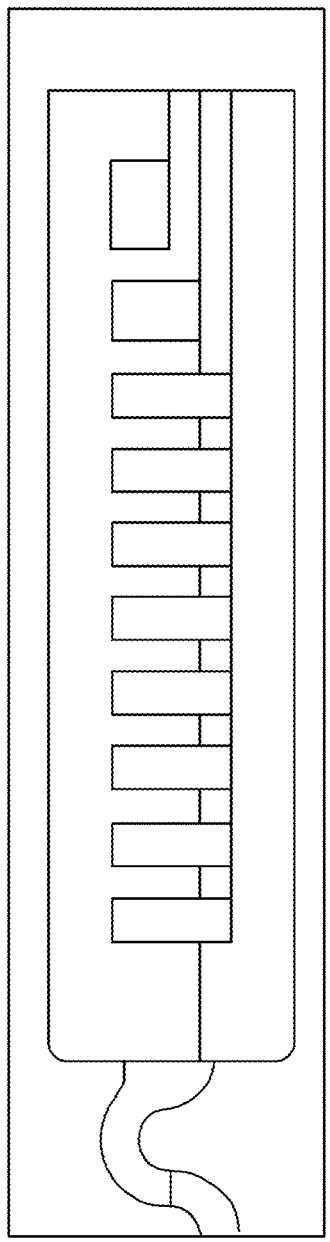
FIGS. 15A-15B show the example application of a polyimide layer of a stretchable electronic system, according to the principles described herein.
Figure 15B:
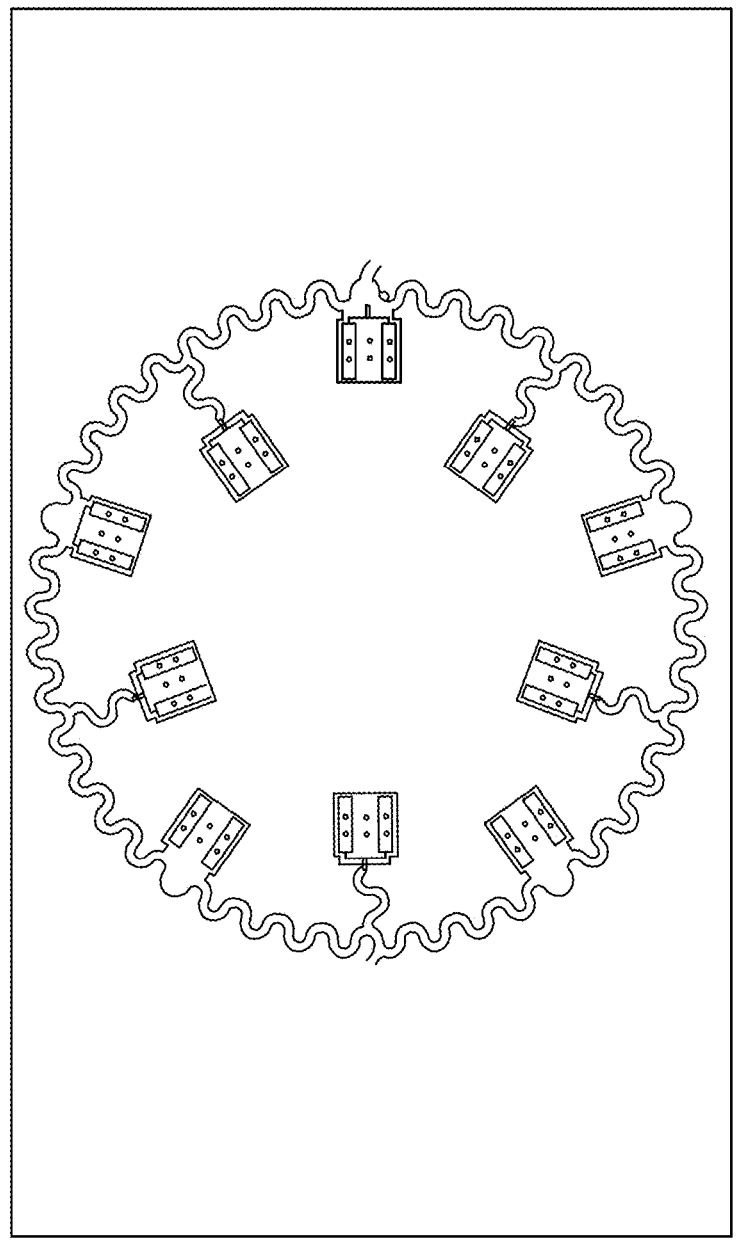

FIGS. 13A-15B show a non-limiting example implementation of fabrication of a stretchable electronic system according to principles described herein. In particular, FIGS. 13A-15B show example intermediate stages in the fabrication of the example stretchable electronic system. FIG. 13A-B shows magnified views of the integrated components of the device of FIG. 13C, a stretchable electronic system according to the principles described herein. FIGS. 14A-14B show the result of a metallization process (facilitated using masking technology) to provide the metal layer of the stretchable electronic system in accordance with disclosed examples. FIG. 14A shows the contact pads at the end of the intermediate bus that facilitates electrical communication with an external power source and/or integrated circuit. FIG. 15A-15B show the application of encapsulant layer over some portions of the stretchable electronic system in accordance with disclosed examples. In an example, the encapsulant layer may be formed from any of the polymer materials described herein, such as but not limited to a polyimide layer, a polyeurethane layer, FIG. 15A shows that the contact pads at the end of the intermediate bus may also be coated at some portions with an encapsulant layer.

Figure 16:
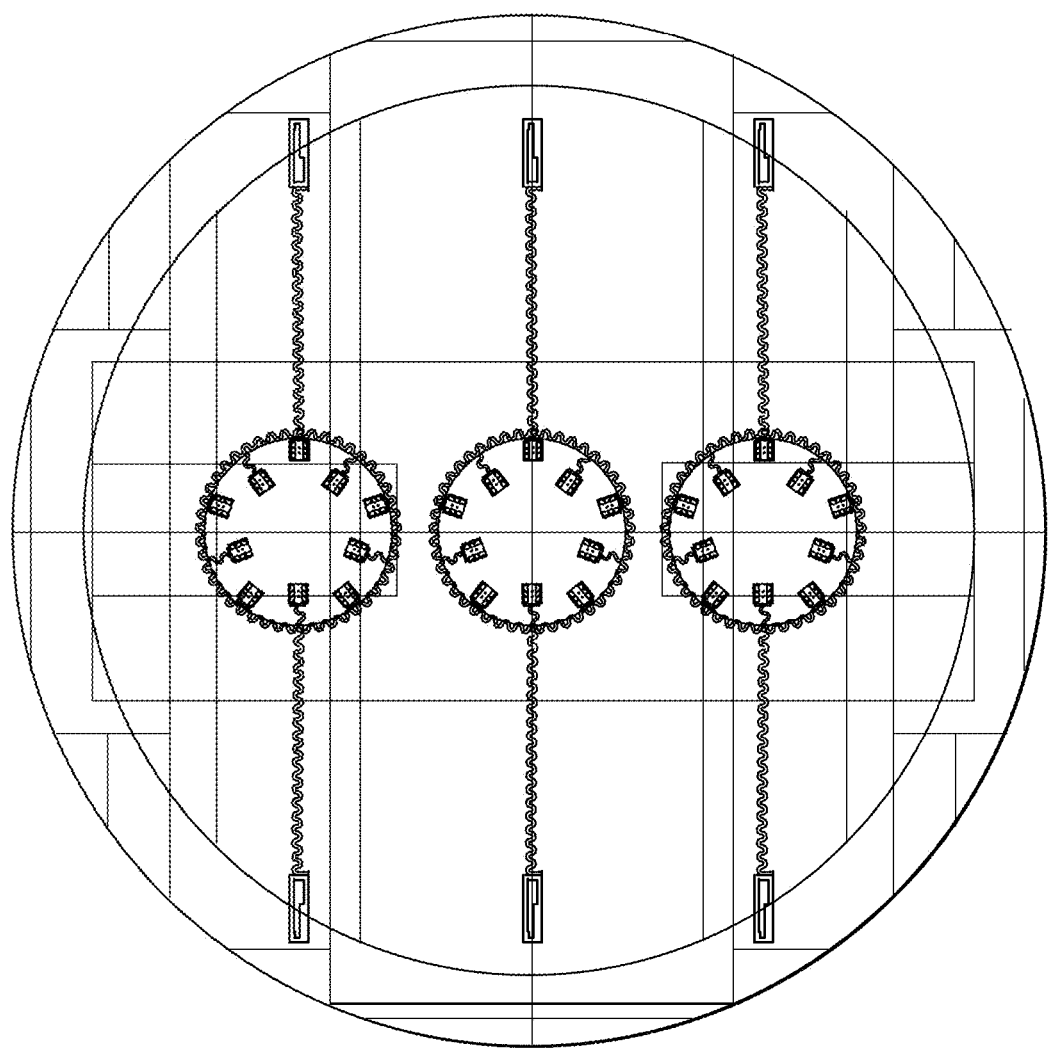
FIG. 16 provides an example of a plurality of stretchable electronic systems positioned on a wafer, according to the principles described herein.

As shown in the example of FIG. 16, a plurality of stretchable electronic systems may be fabricated on a single wafer or other substrate, extracted and disposed on an inflatable body according to the principles described herein.

Figure 17B:
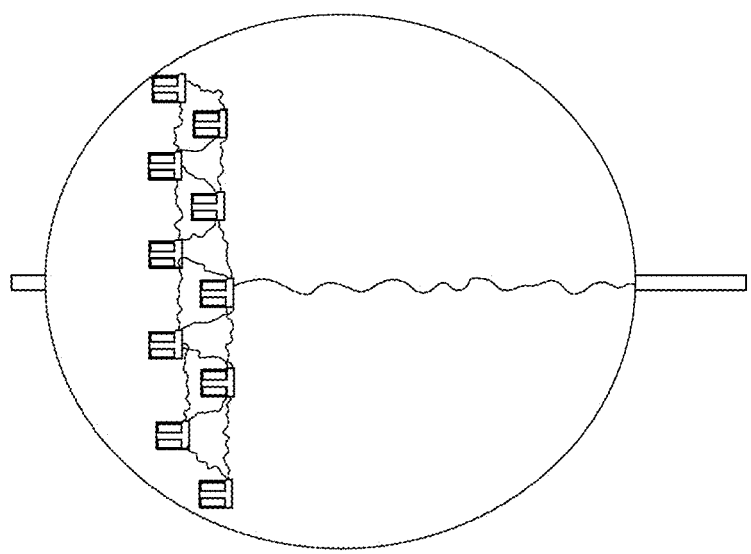
FIGS. 17A-17B are example diagrams illustrating the balloon inflation/deflation process, according to the principles described herein.
Figure 17A:
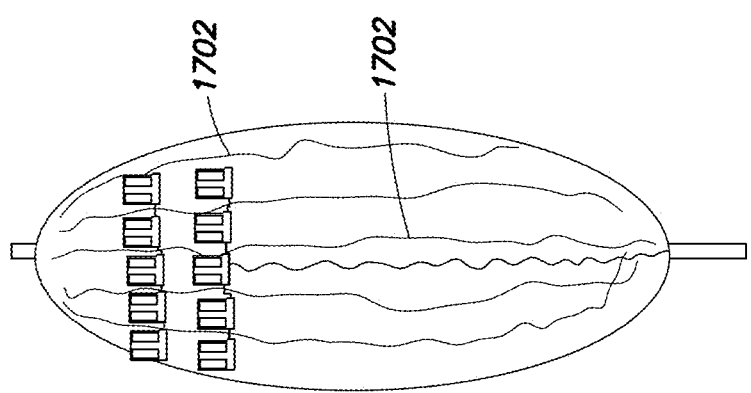

FIG. 17A-17B illustrate examples of a stretchable electronic system disposed about an inflatable body such that the sensing elements 1704 are positioned at two different latitudes. FIG. 17A-B ALSO illustrate the inflation/deflation process of the inflatable body. As shown, the inflatable body can be configured such that small ridges 1702 can form on the inflatable body surface in a deflated state, facilitating for better folding of the inflatable body. According to the principles herein, and as illustrated in FIG. 17A, the plurality of sensing elements can be disposed about the inflatable body such that the sensing elements are disposed at areas of minimal curvature of the inflatable body in a deflated state (which includes a collapsed state). The conformal sensors/electrodes are strategically and selectively disposed between the ridges 1702 at areas of minimal curvature in the deflated state, to minimize applied strain on the sensing elements. Upon inflation of the inflatable body, the sensing elements are deployed in a staggered fashion on the flexible surface of the inflatable body.

Figure 18C:
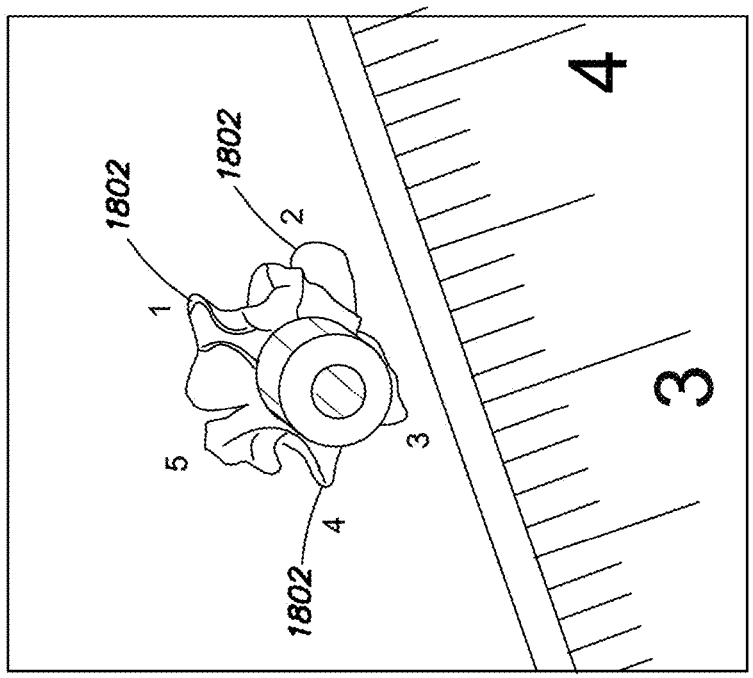
FIG. 18A-18C illustrates another example of a catheter balloon transitioning between an inflated and deflated state, according to the principles described herein.
Figure 18B:
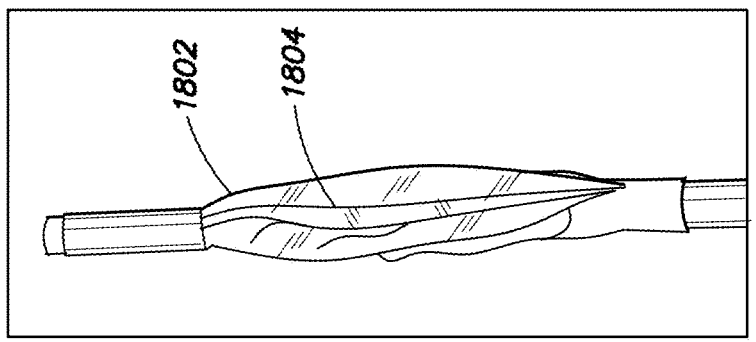
Figure 18A:
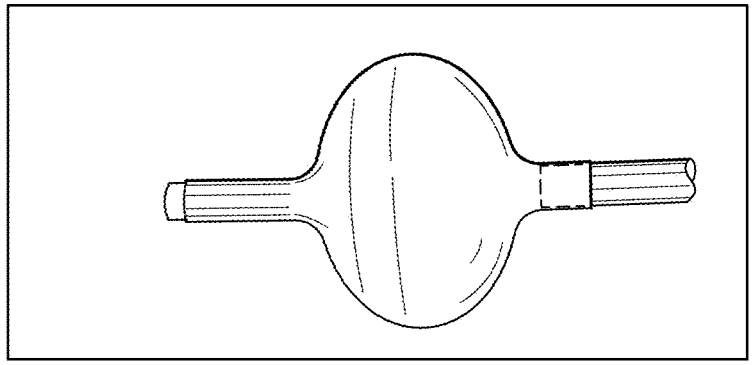

FIGS. 18A-18C illustrate an example where the inflatable body is a balloon catheter. FIGS. 18A and 18B shows the transitioning of the balloon catheter between an inflated state (FIG. 18A) and a deflated state (FIG. 18B). The example balloon catheter of FIGS. 18A-18C has an "onion" shape in the inflated state (a pear-shaped with a curvilinear morphology). Such a balloon may be configured to deflate and to form approximately an average of about five (5) clover-shaped folds. That is, the ridges 1802 in the deflated state extend into the points of the clover-shaped folds, and portions of the balloon between the ridges, the recesses 1804, are disposed closer to the catheter shaft when the balloon is in the deflated state.

The determination of the configuration of the sensing elements on the surface of an inflatable body includes analysis of high and low strain regions of the inflatable body in the deflated state to determine locations on the inflatable body to situate sensing elements so that they experience minimal stress and/or strain, as demonstrated further in connection with FIGS. 17A-B and 18A-18C. Finite element analysis of the stress-strain profiles also enables mechanical optimization such that the sensing elements are located in the area of minimal curvature of the inflatable body, thereby minimizing failure modes during operation (for example, when the inflatable body is being introduced into a tissue lumen prior to being deployed near a tissue region of interest).

Figure 19:
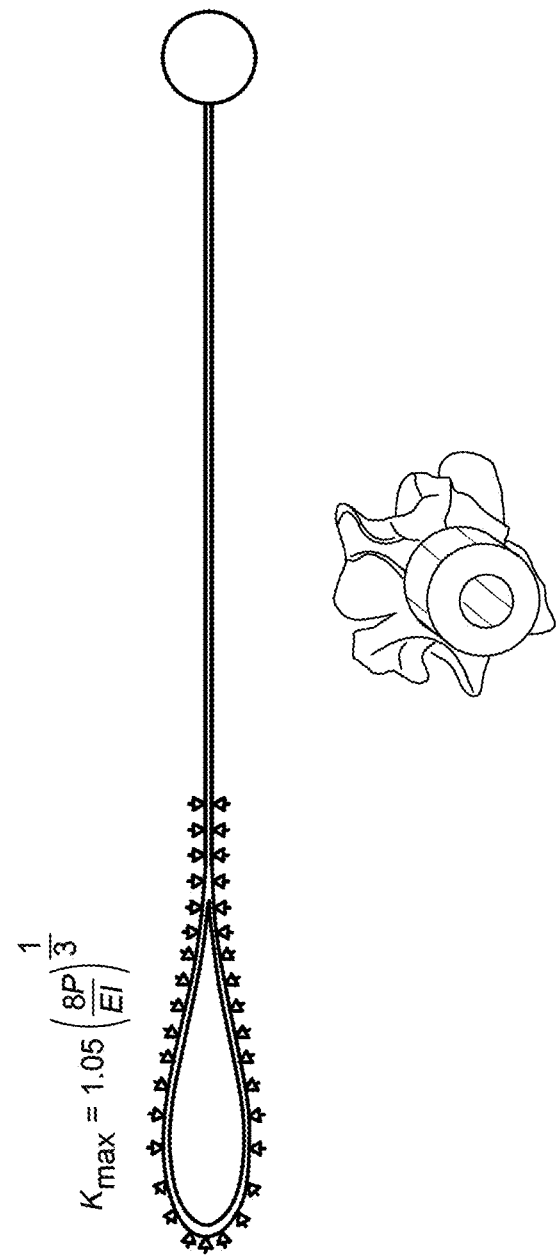
FIG. 19 is a schematic of a folded section of an example deflated balloon, according to the principles described herein.

FIG. 19 is a schematic of a folded section of an example balloon catheter in a deflated state. When a balloon catheter is not pressurized (e.g., in the deflated state), the balloon may form a plurality of folds. FIG. 19 depicts one example of such folds with respect to the catheter shaft. FIG. 19 also shows a mathematical function that can be used to model the curvature (Kmax) at any point on the fold of the example balloon catheter is represented by the equation Kmax=1.05 $(8/ExI)^{1/3}$, where p is approximately atmospheric pressure, E is the Young's modulus of the material of the balloon, and I is the moment of inertia of the balloon catheter.

FIG. 20 shows a graph illustrating the different in computed strain along a folded section of a deflated balloon. In the example of FIG. 20, the arc length from the left point of the balloon to the k=0 location is computed at about s=0.75 mm. The curvature at the left end of the balloon is computed at about 4940 $m^{-1}$ (the maximum of all computed curvature values). The curvature of the balloon at the right end is computed at about 823 $m^{-1}$. As shown in FIG. 20, higher strain regions and lower strain regions (including regions of substantially zero strain) of the inflatable body can be determined. Based on the modeling of the curvature of the balloon in the deflated state, the region on the fold of minimal curvature for the balloon can be determined.

According to the principles herein, based on a model of the expected or predicted folding behavior of an example inflatable body on deflation or collapse, an example stretchable electronic system may be configured, fabricated and integrated with an inflatable body such that the sensing elements are disposed proximate to regions of minimal curvature of the inflatable body (when in a deflated state). For any example inflatable body according to the principles described herein, the folding (or collapsing) behavior of the inflatable body can be modeled or determined based on a number of training samples of the inflatable body, where a pattern of average or most likely folding behavior is determined. As illustrated in FIG. 20, higher strain regions and lower strain regions (including regions of substantially zero strain), including regions of minimal curvature, of the inflatable body can be determined. The flexible interconnect that lead from the sensing elements to the coupling bus can be disposed on the inflatable body so that they traverses the regions of maximal curvature.

Figure 21:
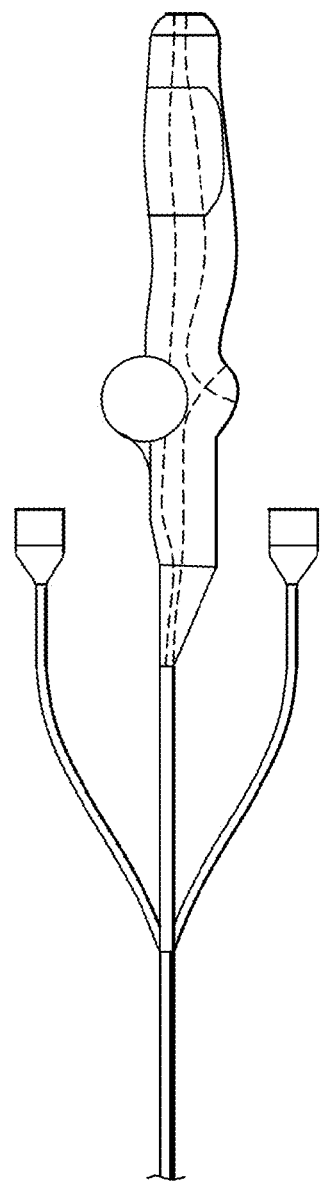
FIG. 21 is a schematic illustrating an example balloon catheter integrated with a flexible electrode configuration, according to the principles described herein.

FIG. 21 shows an example schematic diagram of a balloon catheter integrated with a stretchable electronic system 2104 according to the principles herein. In the illustrated example, the sensing elements, such as the electrodes, are positioned on the distal portion of the balloon 2102. The stretchable electronic system 2102 is coated with a polyurethane encapsulant layer. The polyurethane coated balloon is implemented with a catheter that includes a flexible printed circuit board (PCB) interconnection 2106. In an example, the PCB interconnections may be bonded to the catheter. The electrical leads from the PCB interconnections may extend to a connector housing, which housing may be disposed exterior to the catheter.

Figure 22:
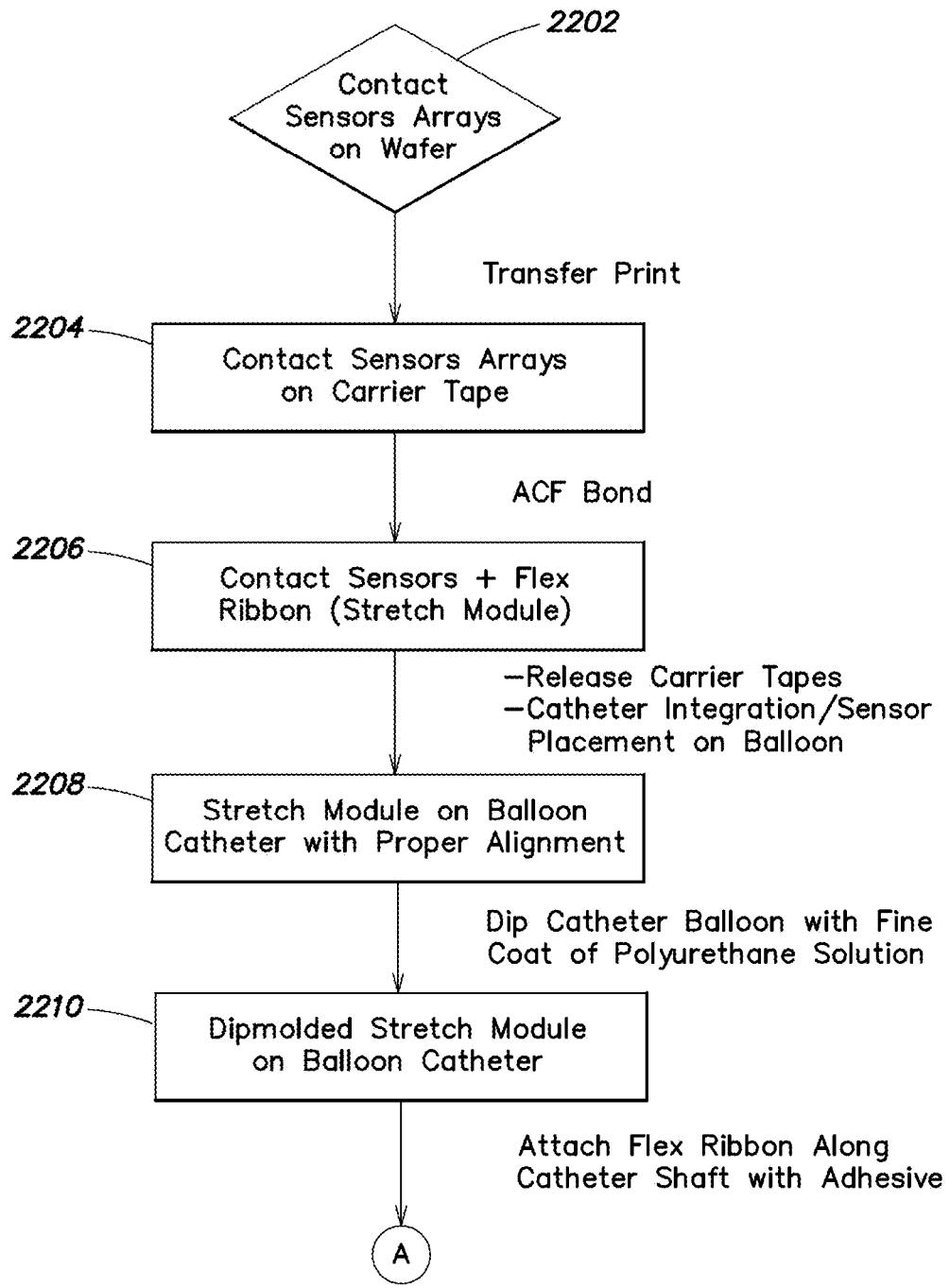
FIG. 22 are a flow chart illustrating a non-limiting example process for fabricating an stretchable electronic system and integrating the stretchable electronic system with a balloon catheter, according to the principles described herein.
Figure 22:
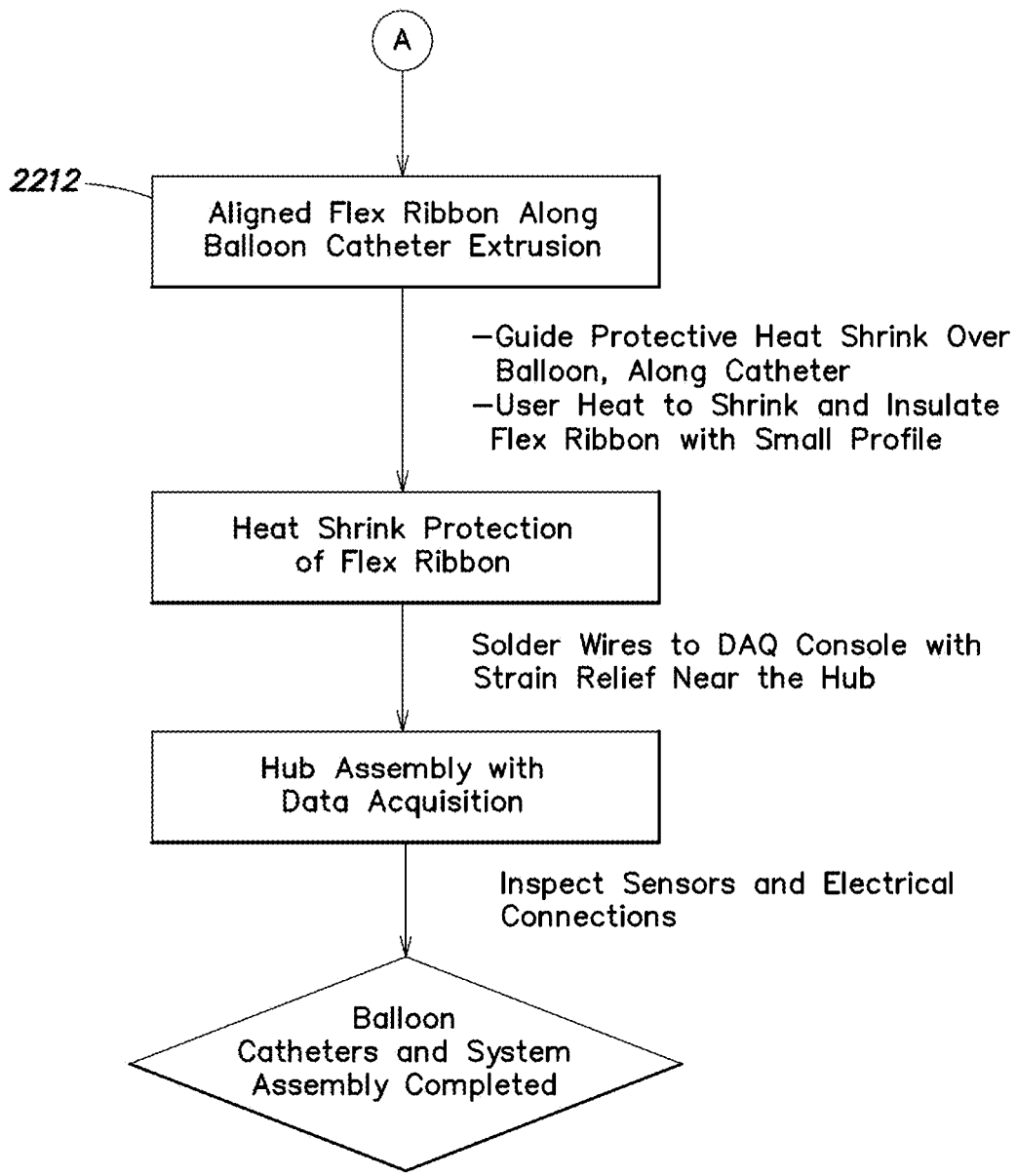

FIG. 22 shows a flow chart illustrating a non-limiting example process for fabricating an stretchable electronic system and integrating the stretchable electronic system with an inflatable body. In this example, the sensing elements of the stretchable electronic system include contact sensors. In block 2202, the stretchable electronic system are fabricated in an array are provided. In block 2204, the stretchable electronic system are transferred to a carrier substrate. In this example, the carrier substrate is a carrier tape. In block 2206, the contact sensors and flex ribbon are connected using conducting film (ACF) bonding. In block 2208, the carrier tape is removed and the stretchable electronic system is integrated with the catheter balloon, including sensing elements placement according to the principles herein, to the integrated system including the stretchable electronic system and the inflatable body. In block 2210, the integrated system is coated with an encapsulant layer of polyurethane to provided a dip-molded system. In block 2212, the flex ribbon is attached along the catheter shaft using an adhesive so that the flex ribbon is aligned along the catheter. In block 2214, a heat protection can be applied to the flex ribbon, e.g., a heat shrink protection, to insulate and protect the flex ribbon while having little effect on the balloon profile. The heat protection can be applied by guiding a heat shrink over the balloon along the catheter. In block 2216, wires can be connected to facilitate communication between the stretchable electronic system and a data acquisition module to provide the fully-integrated system 2218 for use.

Figures 23A, 23B:
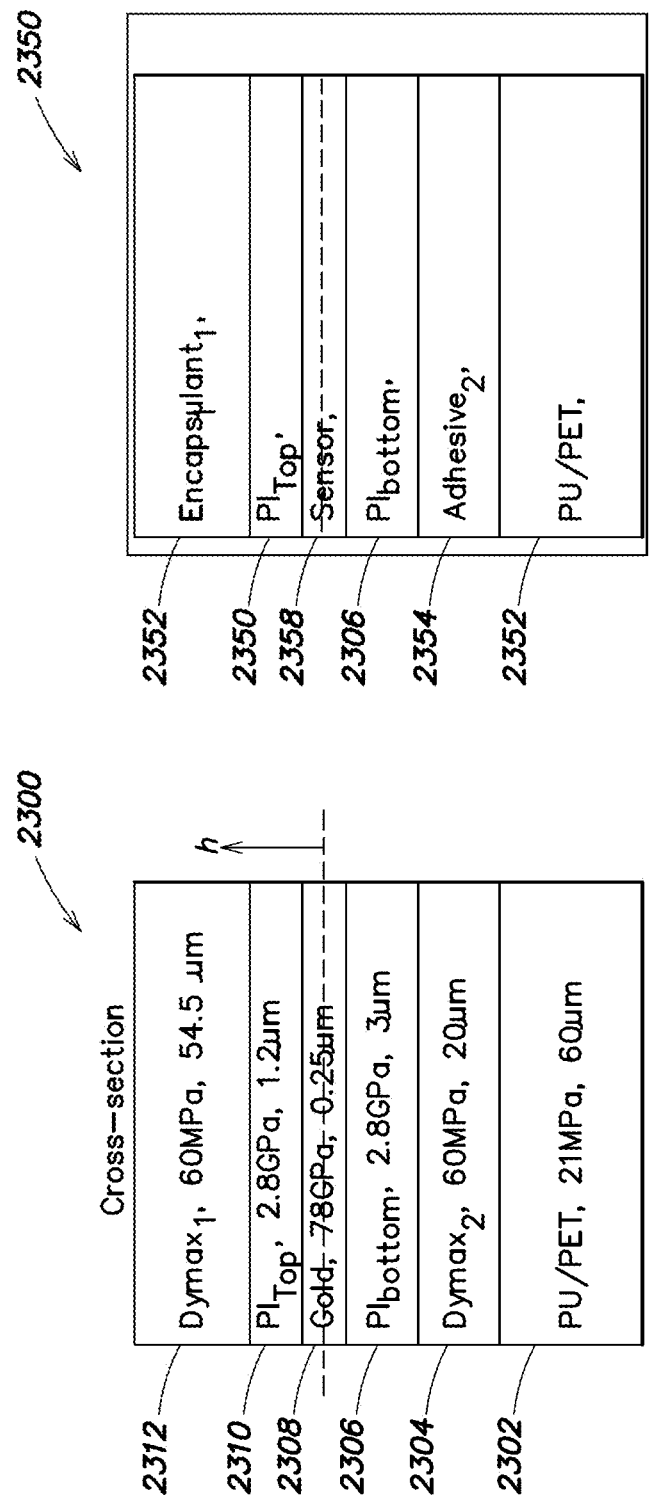
FIG. 23A-23B are example of the layers of a balloon and an integrated electrode configuration implemented to position the electrical components in a neutral mechanical plane, according to the principles described herein.

FIGS. 23A and 23B are examples of the layers of a balloon and an integrated electrode configuration implemented to position the electrical components in a neutral mechanical plane. Nanomembrane contact sensor geometries are unique in the way they impart flexibility to otherwise rigid and brittle materials. Impedance-based contact sensors can be microfabricated using a multi-layer process. The active sensor layer nanometers in thickness and located in the neutral mechanical plane. Subsequent stacks of polyimide and polyurethane films provide encapsulating support to help prevent delamination failure modes. Any suitable encapsulating nonconductive/conductive polymers according to the principles herein can be selectively coated over the surface of the electrodes. This additional layer of polymer provides additional mechanical protection against shear stresses. Alternatively, a few classes of sensors can be located on the PET balloon and covered by the PU layer. The sensors may be completely shielded from abrasion in this particular configuration. Temperature sensors, iLEDs and flow sensors can be employed in this way.

FIGS. 23A and 23B show example layer structures of the stretchable electronic system on a flexible substrate of the inflatable body. The layer structures of both FIGS. 23A and 23B include at least one intermediate layer disposed between the functional layer 2308, and 2508 and the flexible substrate 2302, 2352. For example, layers 2304 and 2306 can serve as intermediate layers for the structure of FIG. 23A. Similarly, layers 2354 and 2366 can serve as intermediate layers for the structure of FIG. 23B. The layer structures of both FIGS. 23A and 23B also include at least one encapsulant layer 2312, 2362 disposed above the functional layer 2308, 2508 and the flexible substrate 2302, 2352. Layers 2310 and 2360 can also serve as encapsulants for their respective device structures. In these examples, each have a number of layers that can serve to provide for strain isolation and place the NMP or NMS (indicated by the "h") proximate to or coincident with the functional layers 2308, 2358. While the layers in FIGS. 23A-B is shown with example layer thicknesses, the structures according to the principles herein are not so limited.

Non-limiting example results of computations of the amount of strain experienced in several layers of the example device of FIG. 23A is shown in Table 1.

TABLE 1

| Material | Max strain (%) |
| --- | --- |
| gold | 0.06 |
| PI | 1.5 |
| DYMAX ® | 27.6 |
| Polyurethane | 41 |

Portions of the functional layer of the system coincide with the plane labeled "gold". As shown in Table 1, the maximum strain computed for the gold layer is around 0.06%, which is lower than the strain computed for any other layer.

Figure 24:
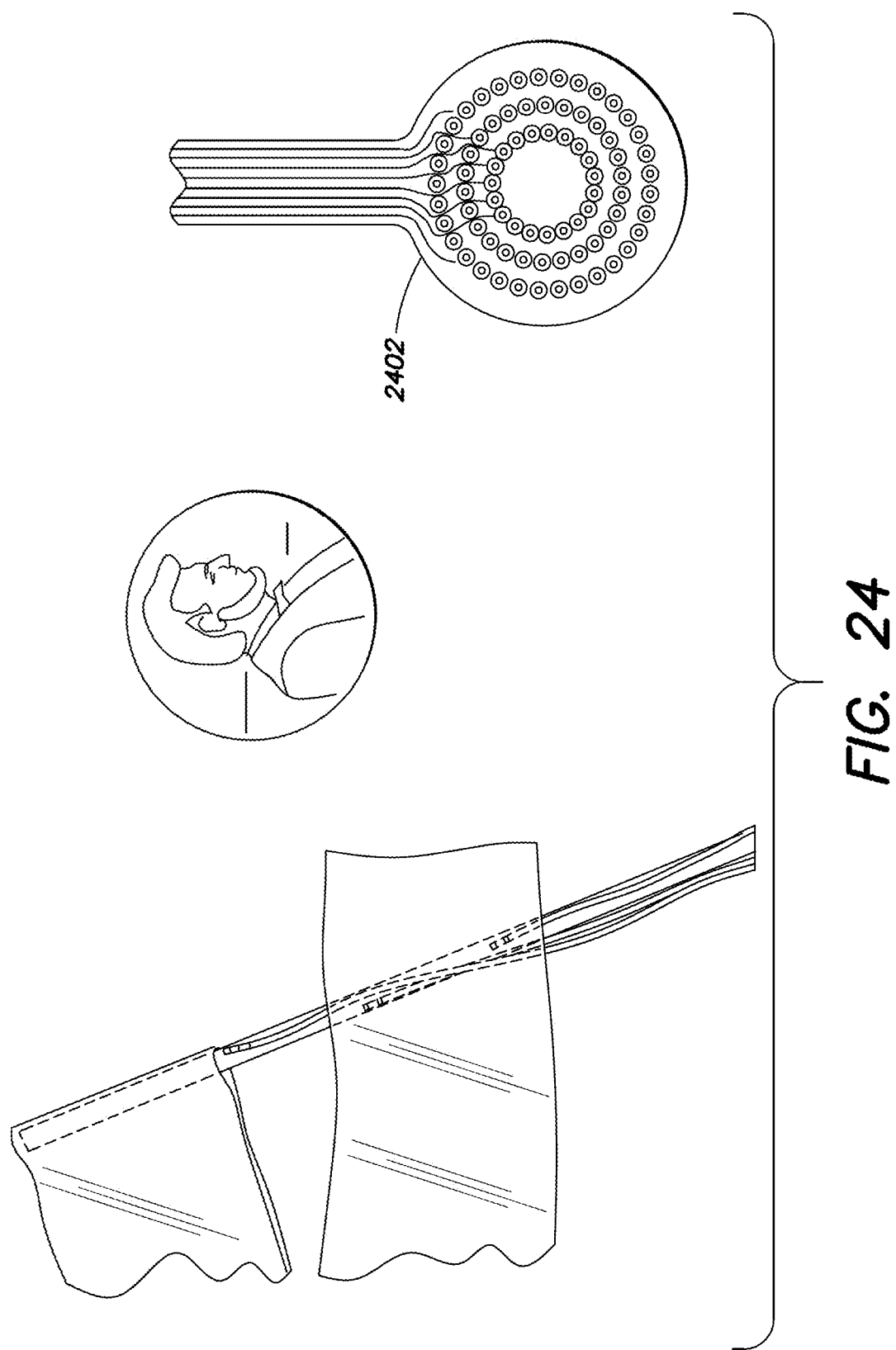
FIG. 24 illustrates an example flex ribbon connector for electrically coupling a plurality of electrodes on an inflatable body with a remote source, according to the principles described herein.

FIG. 24 illustrates a flex ribbon connector 2402 that can be used for electrically coupling a plurality of sensing elements disposed on an inflatable body with a remote source.

Figure 25:
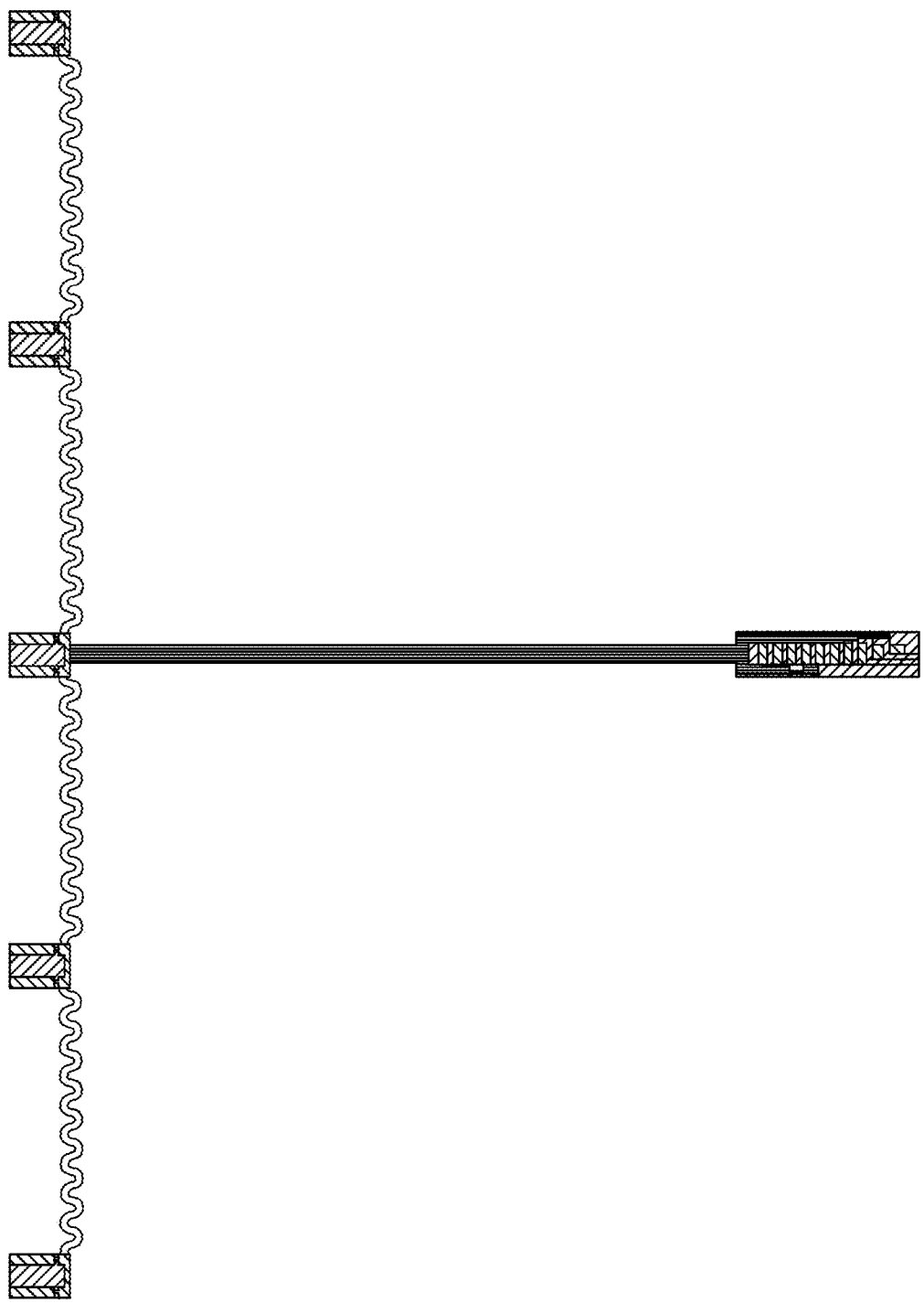
FIG. 25 illustrates an example T-shaped sensing element configuration, according to the principles described herein.
Figure 26:
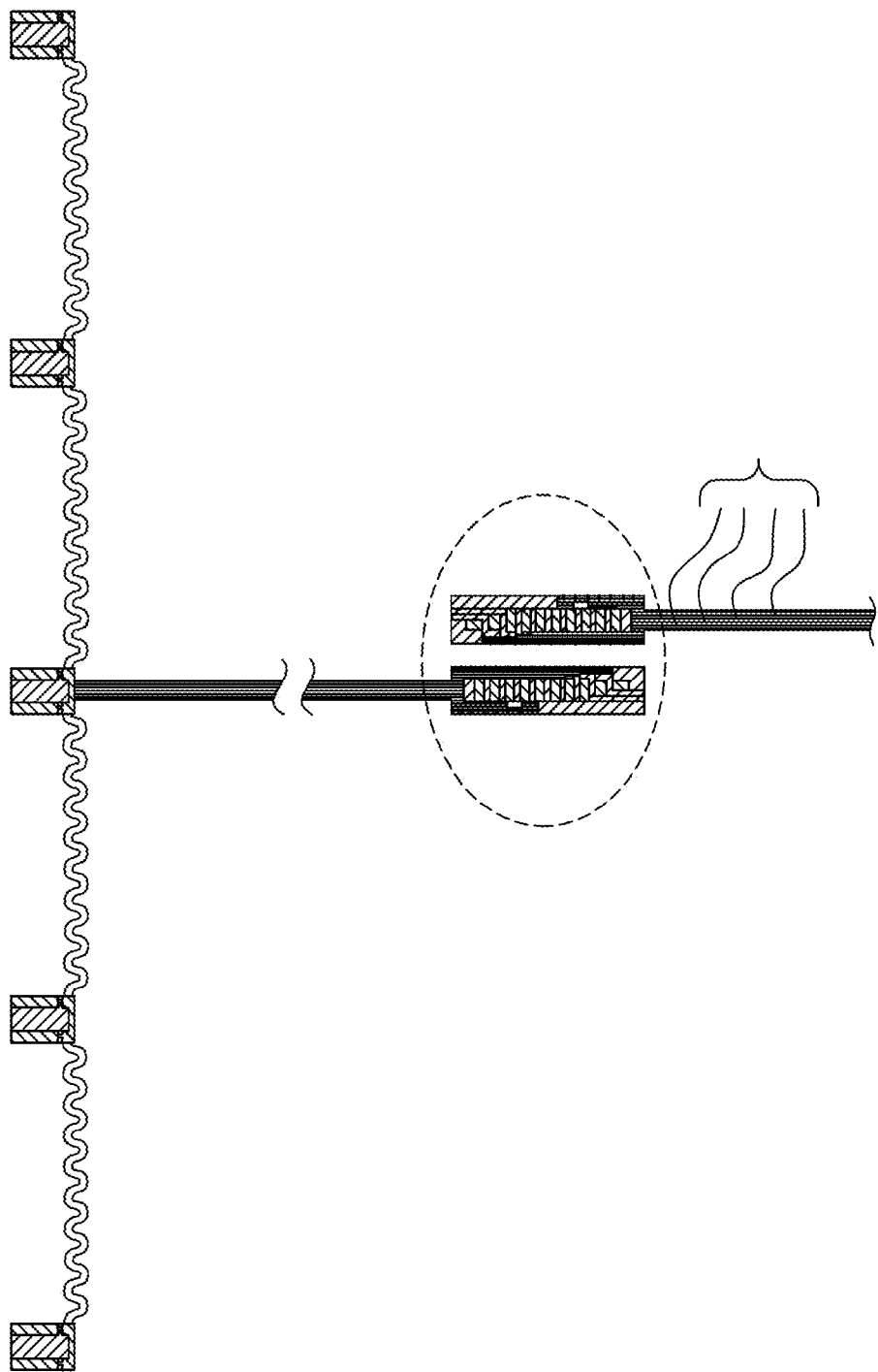
FIG. 26 illustrates an example T-shaped sensing element configuration n including an interface between a coupling bus and a flexible printed circuit board (PCB) positioned on a catheter shaft, according to the principles described herein.

FIGS. 25 and 26 show example configurations of a stretchable electronic system with a coupling bus that has an open-loop structure that can be wrapped around at least a portion of an inflatable body.

FIG. 25 illustrates a T-shaped sensing elements configuration in accordance with various electrode examples. The illustrated T-shaped configuration, may be suited for an inflatable body with a longitudinal symmetry, including a cylindrical inflatable body or an oval inflatable body.

FIG. 26 illustrates a T-shaped configuration including an interface between a coupling bus (also referred to herein as a main bus) of the T shaped sensing elements configuration and a flexible printed circuit board (PCB) positioned on a catheter shaft.

With reference to the FIGS. 25 and 26, the "T-configuration" for the sensing elements arrangement includes multiple contact sensors situated along the horizontal top portion of the T-configuration. The sensing elements in this example are configured as contact sensors electrically interconnected by "serpentine" buses (serving as the flexible interconnects). The contact sensors and serpentine buses form respective flexible/stretchable "arms" that wrap around an outer surface of the inflatable body when inflated. In this example, the coupling bus is disposed at or near the "equator" of the inflatable bus (i.e., at approximately the middle of the inflatable body). The vertical portion of the T-configuration includes an elongated rectangular-shaped "main bus" that is situated along a longitudinal axis of the balloon (so that it is subject to a smaller degree of stretching upon inflation).

To facilitate conformality of a sensing apparatus according to various examples disclosed herein, the flexible substrate of a conformal sensing apparatus may be formed of a plastic material or an elastomeric material, including any of a wide variety of polymeric materials. The bottom terminus of the "main bus" of the T-configuration is coupled to a flexible printed circuit board ("flex PCB") disposed along the shaft of the catheter. As noted below, the interface between the bottom terminus of the main bus and the flex PCB includes various examples. Small wires to carry signals "off-catheter" can be attached to the flex PCB via solder connection.

In one implementation, each contact sensor is wired individually (i.e., two conductors/sensor) such that a pair of wires are available "off-catheter" for each sensor. Working from "off-catheter" to the contact sensors themselves, and considering an example involving five contact sensors, ten wires are soldered to the flex PCB, and the traces on the flex PCB are designed such that there is approximately a "one-finger distance" between respective solder points (to facilitate assembly by hand).

The interface between the main bus of the T-configuration and the flex PCB involves the mechanical and electrical coupling of 10 contact pairs via a specially selected adhesive and contact layout. In this non-limiting example, the main bus includes 10 conductors electrically insulated from each other, and two of these conductors that are electrically coupled to a central sensor situated at the intersection of the main bus and the horizontal top bar of the T-configuration.

Four conductors then travel down the serpentine bus to the left of the central sensor (for the two additional sensors to the left of the central sensor), and four conductors travel down the serpentine bus to the right of the central sensor (for the two additional sensors to the right of the central sensor). The "outermost" portions of the serpentine bus on the far left and far right arms each carry two conductors for the outermost left and right sensors.

Figure 27:
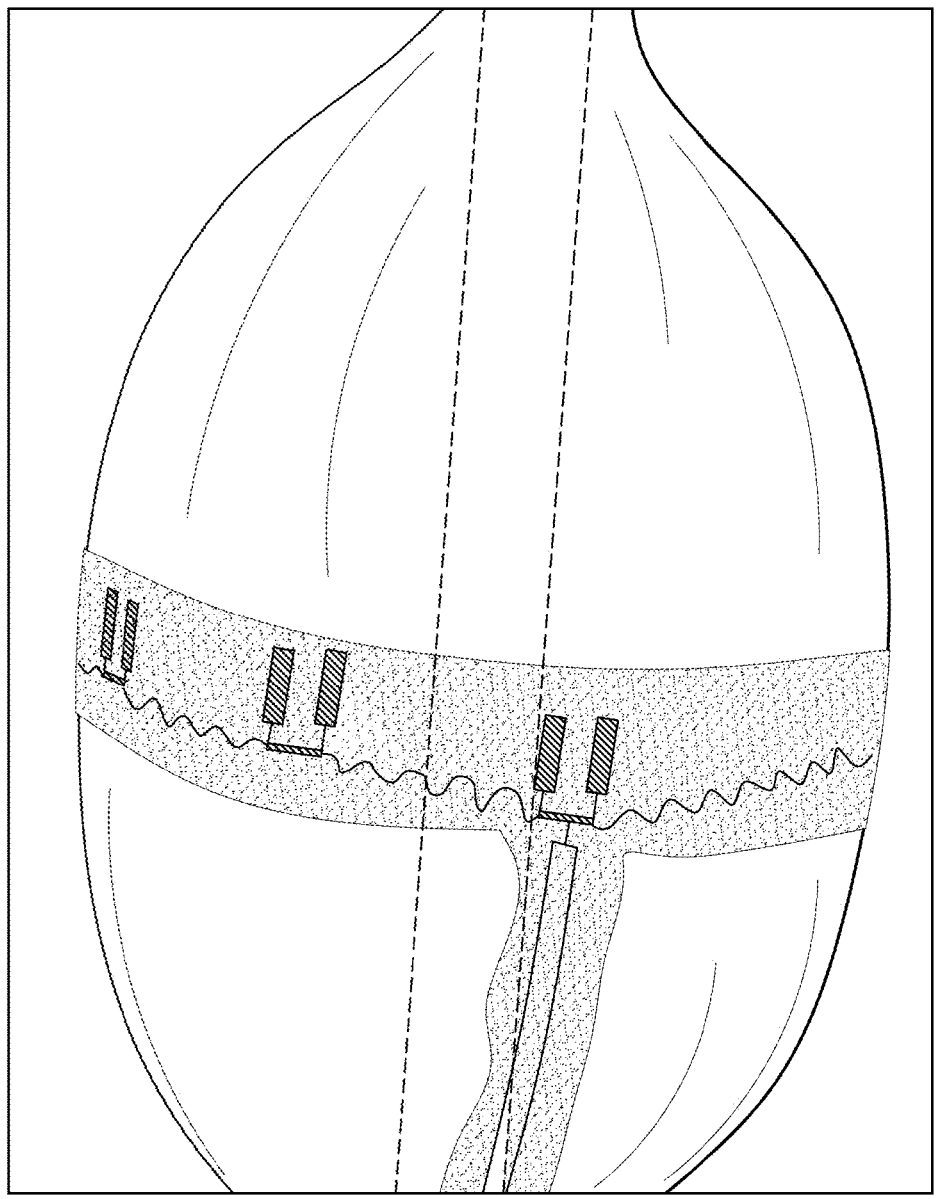
FIG. 27 illustrates an example T-shaped sensing element disposed over an inflatable body, according to one example, according to the principles described herein.

FIG. 27 shows an example of a stretchable electronic system having a "T-configuration" of coupling bus and sensing elements disposed over an inflatable body, such as a catheter balloon.

Figure 28:
FIG. 28 a schematic diagram of an example flex boar, according to the principles described herein.

FIG. 28 a schematic diagram the flex board, according to one example.

The flex PCB may be referred to as the flex connector, or the flex board. FIG. 28 provides an overview of the top layer of the flex board, which mates with the stretchable electronic system on the balloon.

On the left are 10 exposed metal contact pads that interface directly with Pi-Cr—Au via ECCOBOND® adhesive (anisotropic conductive paste; Henkel Corp.), and provide connection to the flexible T electrodes.

The staggered rectangles on the right are the solder bumps that mate with wires leading along the catheter. They are staggered such that the wires do not bundle together. Bundled wires would cause undesirable increase in catheter shaft diameter.

For adhering the balloon electrodes/contact sensors, the balloon (made of e.g., Polyurethane polymer) may be selectively coated with DYMAX® 204 UV curable adhesive (Dymax Inc,) with a lateral spatial resolution of, for example, >25 µm.

Prior to UV exposure, the balloon is wrapped with a sensor array distal to the equator.

The assembly is then placed under UV light cycles to promote strong adhesion between surface of the balloon and the back-side surface of the sensor array. For example, the assembly can be exposed to UV light at 15 second intervals for up to about 5 minutes. In another example, the UV light is cycled at 30 second intervals.

Next, the water-soluble tape is dissolved away, and the surface of the assembly of the balloon and the sensor array is dried.

Mold polyurethane may then be sprayed onto the surface of the balloon with predetermined thickness and configuration of top encapsulation.

Windows can be left open surrounding the electrodes so that they remain exposed for effective tissue contact.

Once the spray mold procedure is complete, UV cure/polymerization follows, creating an even coat of polymer on the balloon. This top layer of polymer provides further protection against shear forces and may impact durability of the balloon catheters/sensors assembly.

Clinicians may use x-ray to determine when the balloon is out of the sheath and inside the left or right atrium (i.e., positioned in a specified contact with the tissue lumen). Some clinical protocols use x-ray even during the pre-ablation routine to determine the type of contact the catheter balloon has with the tissue.

An example integrated system according to the principles described herein may be used to provide an indication of when the balloon exits the sheath and comes in contact with blood. The sensors providing in accordance with disclosed examples permit identification of locations such as inside the heart and passed the sheath (prior to any sensing within the ostium).

The technology used in this flex connector is applicable to many other applications as well, and the flexible/stretchable materials make physically and electrically robust connection to rigid components in a system.

The following disclosure describes various challenges associated with making a reliable, robust connector for electrophysiology, and design considerations which may be applicable to address these challenges and other applications.

A reliable connection is desired between the sensing elements and the flex board. For example, the larger the contact area, the sturdier the connection that can be made between the electrodes and the flex board. In one example, the area is constrained to about 2 mm in width (y direction in FIG. 28) because of the catheter shaft dimension, as this flex board is disposed inside a catheter shaft. In addition, increasing the length too much can also make it difficult to align.

An adhesive may be used to make the electrical and physical contact between the flex board and the T electrodes. In one measurement, ACF tapes manufactured by 3M are used. Alternatively, ECCOBOND® can be used. Measurements can be run to optimize the area of bonding, temperature, and duration of adhesive application.

In some examples, the target contacts may be made sufficiently large enough so that the electrodes may be manually assembled to the flex connector. The contacts (shown on the left side of FIG. 28 are sufficiently wide to be visible by eye. Moreover, they are sufficiently short in the X direction such that small rotational errors in placing the T electrodes may not cause a misconnection.

In an example, a large electrical contact area is desired but it can be limited by the width (y direction in FIG. 28) of the connector because it fits in a catheter. In addition, if the length of the total length of all contacts (x direction in FIG. 28) is too long, rotational errors in placement can misalign the far left and far right contacts. This is due to that when the flex PCB is placed on the T electrodes, there is a tendency for rotation.

The longer the x direction, the greater the arc as determined by the radius from the center to the far x edge multiplied by the angle. Thus, there is a balance of opposing goals. On one hand, it is desirable to improve visibility and hand manufacture by making the pads bigger and longer. On the other hand, increasing them too much adds rotational errors and a jig can then be used to keep the components from rotating. This trade-off can be determined by trial and error.

In an example according to the principles herein, the total electrical contact area is roughly 6.3 mm×1 mm and includes of 10 individual contacts. Increasing the area makes the electrical contact stronger. To maintain equal impedance for each of these electrical contacts, they are made to be the same area.

In addition, since some limitations may be place on the number of layers of flex board, the electrodes are sized in such a way that traces can be routed. The contacts start out longer in the y direction on the left but begin to switch to rectangles that are longer in the x direction as it moves to the right. The same area is maintained in each case, not only to align impedance but also to maintain good contact.

Many contacts span longer in the y direction since this flex board goes into a catheter. The majority of pressure on the flex board is at the north and south edges (staring down at the flexboard shown in FIG. 28). The catheter shaft can be viewed as "hugging" this flex board and bending the north and south edges. Thus, it is desirable to ensure there is some amount of electrical contact in the middle region between the north and south of the flex board.

The flex board can be configured to have two (2) layers, as additional layers may increase stiffness and may adversely affect the flexibility of the catheter. In addition, it may exceed the catheter shaft size limit. Fewer layers of flex board can be used but still provide for the optimal number of traces. In one example, a 2 mil polyimide base, a 1 mil polyimide film insulation, and a 1 mil acrylic adhesive are included. Thinner materials can be adopted, although the cost may be higher.

Manufacture of a longer (e.g., 48") and thin flex board may be associated with high cost and low yield. Alternatively, a short flex board (e.g., 6") may be used, with longer wires.

The flex board can be made contact with the flexible sensing elements (including electrodes). In one example, the total length of the flex board is about 6 inches. The right side of FIG. 28 shows the wire contacts. By using wire for the majority of the catheter length, the cost can be reduced while maintaining a relatively thin size. This also improves flex board yield.

The wire contacts can be made water-proof since this is an electrophysiological application and the catheter is in the body. The wires are soldered onto the wire contacts, and a protective material, such as but not limited to ECCO-BOND® 45+Catalyst 15 (Emerson & Cuming, Randolph, Mass.) can be applied, e.g., to them to make them water proof.

This example flex board design shown in FIG. 28 has 10 electrodes. This design can scale by using two flex boards to increase to 20 channels. The number of channels on one flex board can be increased and additional wire contacts added.

In some examples, a multiplexer is added to the flex board to reduce the number of traces on the flex board while allowing many channels. A system according to one example has a multiplexer on the balloon itself to minimize the number of traces at the flex board.

Figure 29A:
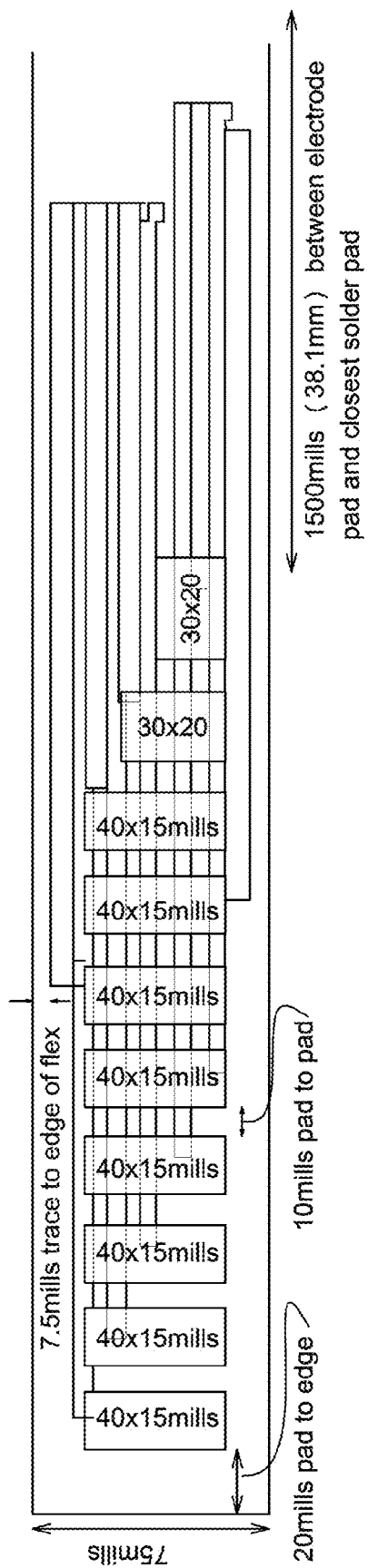
FIGS. 29A-29B illustrate an example schematic plan for a flex board design, according to the principles described herein.
Figure 29B:
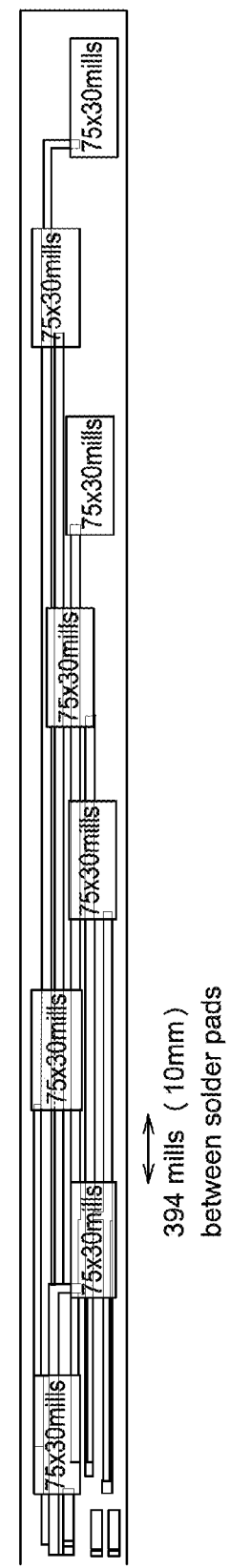

FIG. 29 illustrates an example schematic plan for a flex board design.

Figure 30:
FIG. 30 illustrates the bottom layer of the example flex board, according to the principles described herein.

FIG. 30 illustrates the bottom layer of the example flex board.

Figure 31:
FIG. 31 illustrates a top layer of the example flex board, according to the principles described herein.

FIG. 31 illustrates a top layer of the example flex board.

Figure 32:
FIG. 32 illustrates an encapsulation layer of the example flex board, according to the principles described herein.

FIG. 32 illustrates an encapsulation layer of the example flex board.

Vertical orientation of contact pads and traces can help maintain a low-diameter catheter shaft.

The contact pads can be optimized by making them wide in the Y direction. The flex board bends across the shaft in the Y direction. Thus, largest forces occur at the furthest Y edges. Therefore, to maintain good contact, spanning the entire Y may be desired. Increasing the area is also a goal to improve electrical contact. The constraint is the overall contact group size. In this example, it is roughly 2 mm in Y and 7 mm in X.

In one example process of manual bonding, the main bus and flex PCB are first manually aligned with a microscope; then a device is being constructed to perform alignment and heat curing; if contact pads do not overlap or if they touch adjacent pads then the circuit may be shorted.

Suitable adhesives/epoxies for appropriate strength and flexibility used to couple the main bus and the flex PCB may include ECCOBOND®, and HYSOL® (Henckel, Rocky Hill, Conn.) CE3126 snap curable anisotropic adhesive, the latter can be cured at 170° C. for 4 minutes to bond the main bus and flex PCB. Other suitable adhesives/epoxies may also be used.

The main bus can be made narrow (e.g., <1-2 mm) in order to achieve a smooth transition from the catheter shaft to the surface of the balloon. The more conductors, the more lateral width is added to the main bus. Fewer serpentine interconnects may be disposed along the main bus given the vertical orientation.

Because most of the strain occurs along the horizontal direction during inflation, and not the vertical in most ellipsoidal and spheroidal balloons, an example configuration includes keeping the length of the main bus minimized (impedance low) and the width as narrow as possible.

The main bus can be made wavy to allow for stretching during balloon inflation/deflation. Alternatively, a straight main bus can be flexible but not stretchable. The wavy design can be used to place electrodes distal on the balloon, as the main bus may travel over a greater balloon curvature.

The sensors and serpentines can be microfabricated during the same process of polymer and metal vapor deposition. They can be deposited in sequential layers. The discrete sensors may be picked and placed onto the underlying metal interconnect layers, thus forming a network of metal interconnections with discrete sensor units.

Anisotropic conductive films and a flip chip bonding tool can be employed to make these connections. Alternatively, conductive anisotropic epoxies, such as the ECCOBOND® 3126 resin, can be used.

Serpentine interconnects can have greater curvatures to allow for more stretching. The coupling busses and interconnects described herein cab be formed of interconnects with a serpentine geometry. Optimal designs can be based on the balloon geometry, electrode placement, and folding behavior for inflation/deflation.

In one example, electrical "bipole" sensing elements are used to measure impedance difference between blood and tissue of lumen's inner surface through "current injection" and voltage measurement across bipole pair (at ~kHz frequency operations for example).

Polyimide pads can be disposed underneath bipoles to prevent changes in separation distance upon inflation. The polyimide pads under electrodes can be made slightly larger to accommodate an encapsulation layer around the electrode border, minimizing delamination.

The degree of contact can be determined based on that greater amount of pressure applied to tissue can give a higher impedance, and can show whether the electrodes are in complete contact or partial contact (decreased impedance).

Tissue characterization can be realized using measurements of impedance changes in healthy tissue as compared to damaged tissue. Electrical impedance can also be used, post-ablation, to assess lesion depth. A user interface allows visualization of contact in real time.

In one example, the contact sensing elements employ PSR (pressure sensitive rubbers), such as Piezo-electric conductive polymers. In some other examples, capacitive sensors can be employed, where blood or body tissue results in different changes in the capacitance.

In some examples, temperature sensors are disposed on the balloon surface. Changes in electrical impedance can also be based on local temperature. The temperature sensors can provide real-time temperature data during cryoablation or RF ablation.

Monitoring tissue temperature can provide estimate of lesion depth/quality. LEDs can be disposed on the balloon to provide illumination.

A "T"-configuration of individually-wired contact sensing elements and their electrical characteristics are described.

Balloon shapes from different manufactures may differ, and size, geometry, placement/orientation of sensor assembly can be customized on different balloons. In one example, sensors can be placed distal on balloon for pulmonary vein isolation (PVI) monitoring. Different stretch behavior may exist for balloon inflation/deflation. In one example, very small ridges exist on a Cryoballoon manufactured by a particular manufacturer, which may experience more stretching between inflation and deflation. The surface area of a deflated balloon may limit the size and number of electrodes. In one example, the electrodes are staggered diagonally to fit more on a deflated balloon. The electrodes can spread out into a line upon inflation.

In one example, the electrodes are staggered in two rows, or as vertical lines on the balloon, as described in the related patent applications.

Modeling the behavior of respective sensors from the central sensor to the outermost left and right sensors may be used to derive frequency/impedance characteristics of these sensors. For example, the impedance can be 2-3× larger for sensors on the edges compared to the center sensor. The impedances may not be symmetrical around the main bus or matched, so long as they are below a threshold. Signal filters and gain adjustment can be used to amplify signal amplitudes. In one example, the T-shaped structure is symmetric and has known changes in impedances. The overall variations in impedance are not significant to effect signal analysis.

For PVI, a higher density of sensors may be used to determine a complete occlusion. The density of sensors may be limited by the number of wires that can fit in the flex PCB, the number of contact pads on the flex PCB, the size of main bus, etc.

A non-limiting example of integration of a stretchable electronic system and an inflatable body can be implemented as follows.

Figure 33:
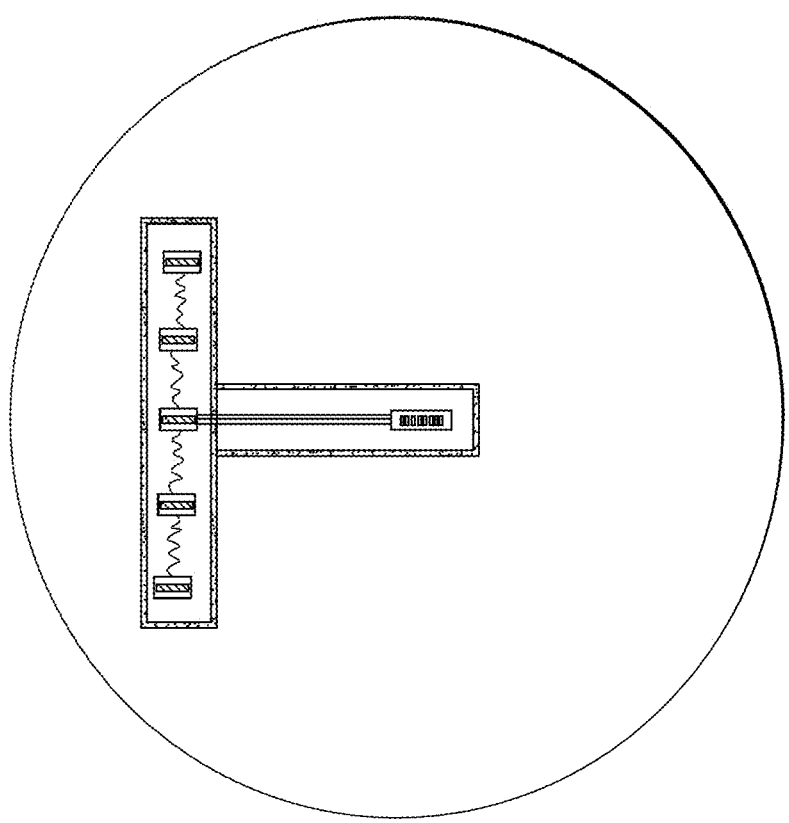
FIGS. 33-45 illustrate stages in an example fabrication process of a balloon catheter with an array of sensing elements in a stretchable electronic system, according to the principles described herein.

Block 1. As illustrated in FIG. 33, water soluble tapes can be applied. Water-Soluble Wave Solder Tape 5414 (water soluble poly-vinyl alcohol backing with synthetic adhesive) can be applied over the fabricated sensing elements array on the silicon wafer. Horizontal strips can be laid first.

Figure 34:
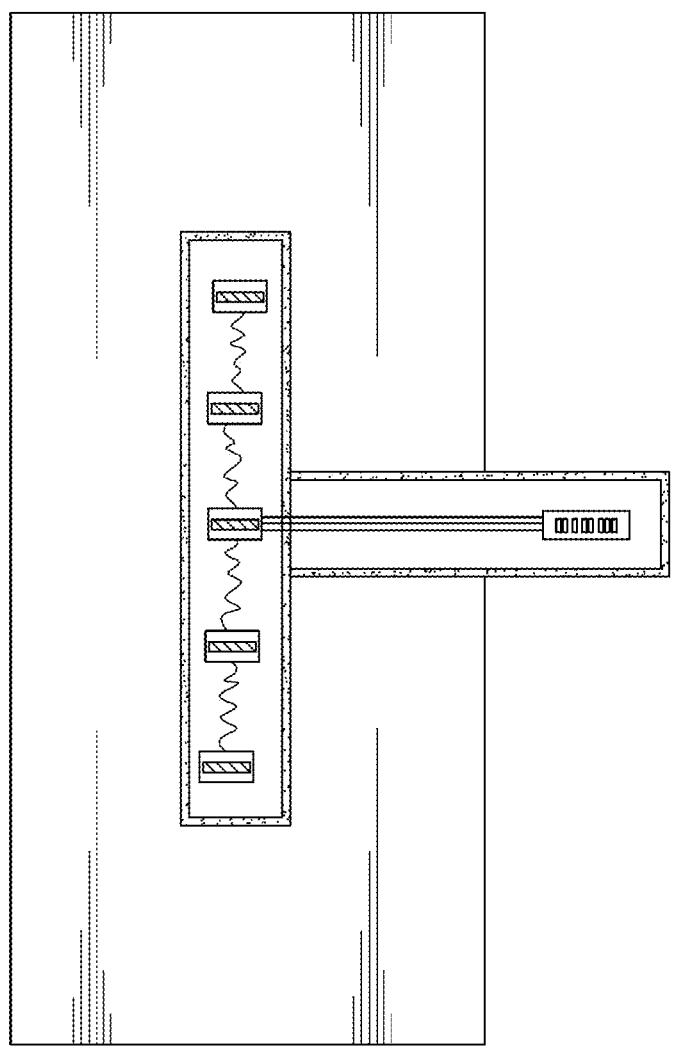

Block 2. As illustrated in FIG. 34, the electrode array is removed from the silicon wafer. The soluble tape and sensing elements array can be removed from the wafer starting on one of the top corners of the "T". The array can be transferred to a piece of flex metal, leaving the bottom portion with the flexboard connection hanging off the edge of the metal.

Figure 35:
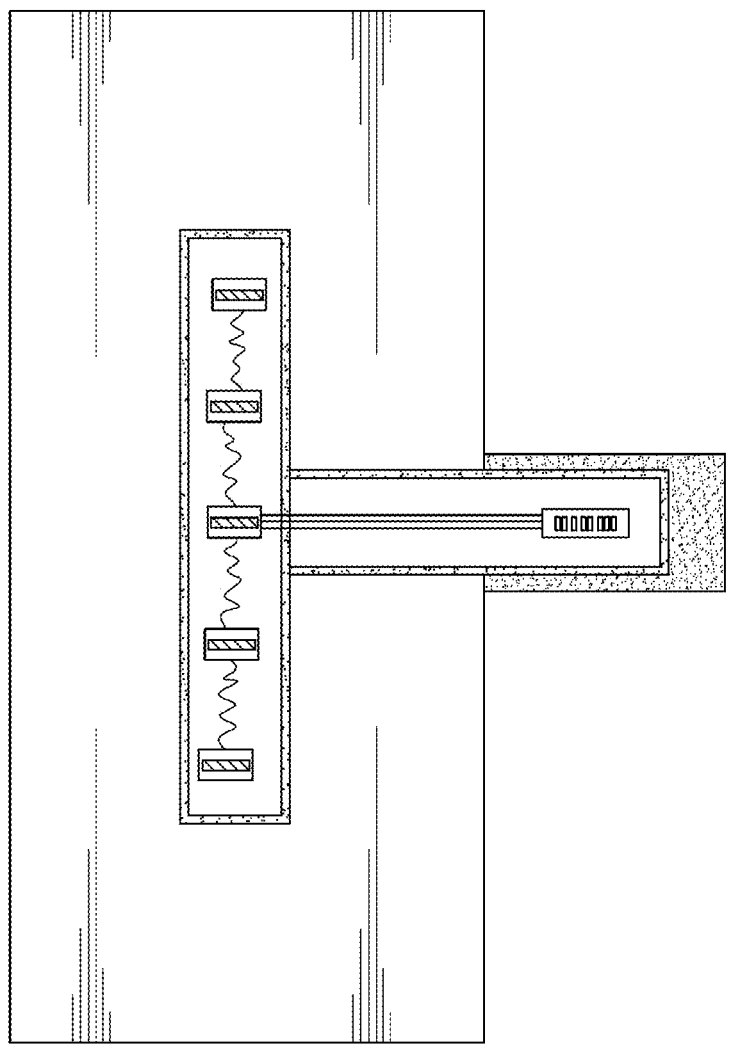

Block 3. As illustrated in FIG. 35, the tape can be applied to the flexboard connection. A piece of polyimide (PI) tape is affixed to the exposed soluble tape on the back side of the flexboard connection.

Figure 36:
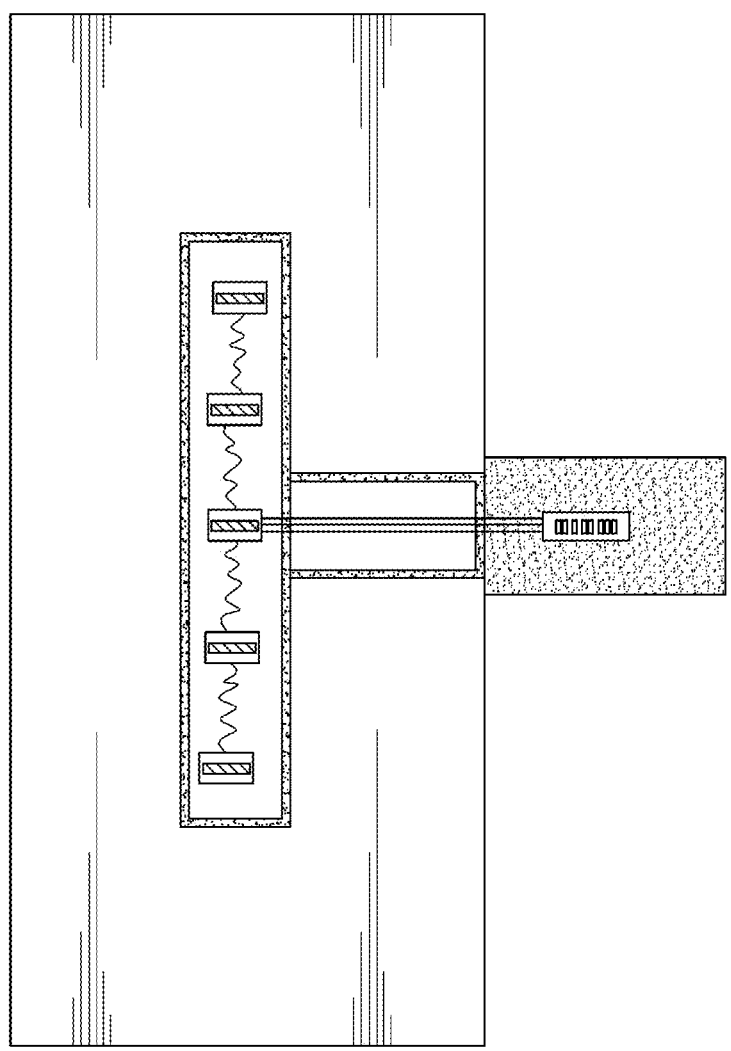

Block 4. As illustrated in FIG. 36, the flexboard connection is exposed. The soluble tape s removed from the region with the PI-tape, leaving the electrode array affixed to the PI. The soluble tape is excised at the PI and flex metal junction. Exposing the exposed length of PI/soluble tape to a water bath at ~50° C. can cause the soluble tape in the region over the PI tape to selectively dissolve.

Suitable materials other than water soluble tape may be used. For example, tapes with short adhesive life cycles can be used within a finite time window. Once the adhesive are reduced, the outcome can be similar to when one applies water to the water-soluble tape.

Figure 37:
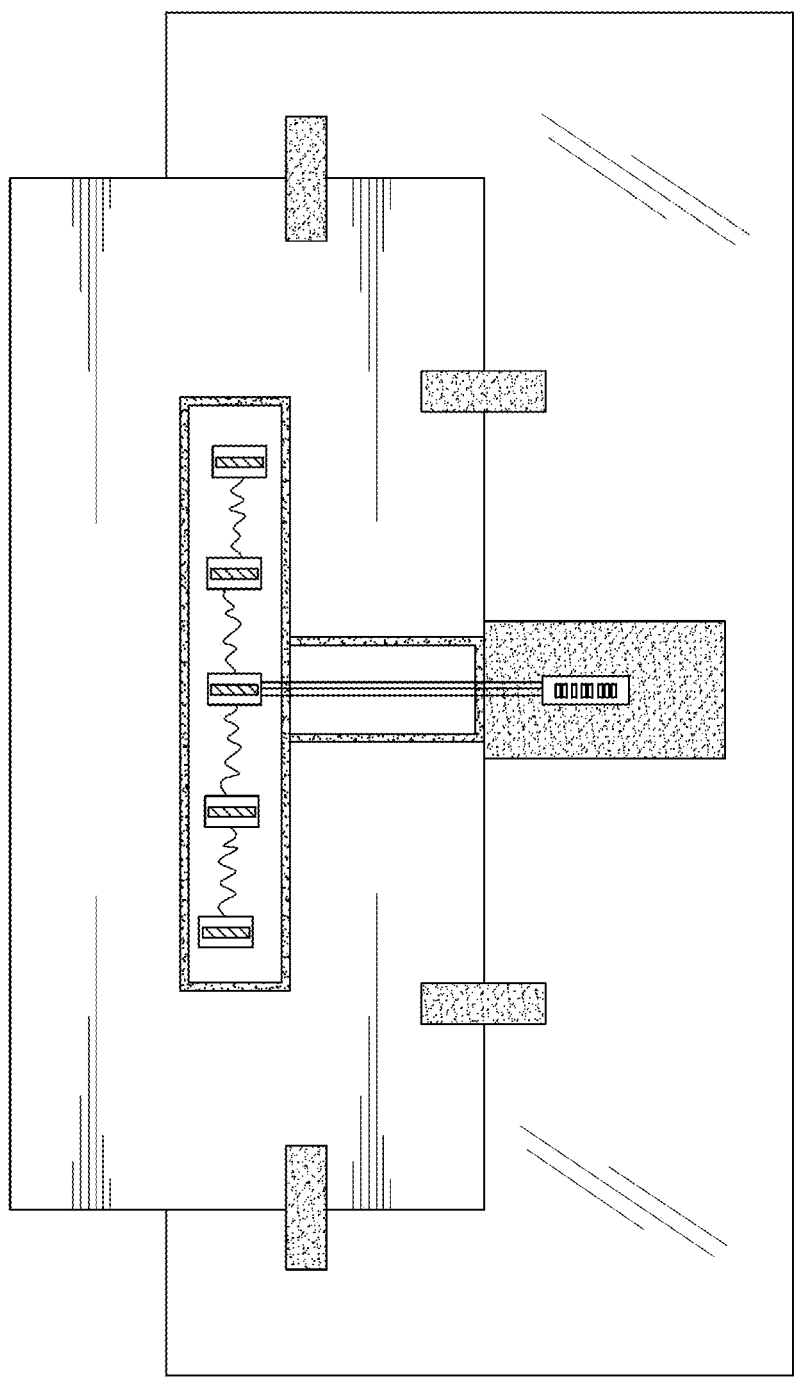

Block 5. As illustrated in FIG. 37, the array is placed on glass. For example, a glass slide can be affixed behind the flex metal and PI strip using PI tape. Large portions of the flexboard connection may be left exposed.

Block 6. The glass slide can be affixed to a microscope stage so that the contact pads on the flexboard connection are clearly visible through the eyepiece.

Figure 38:
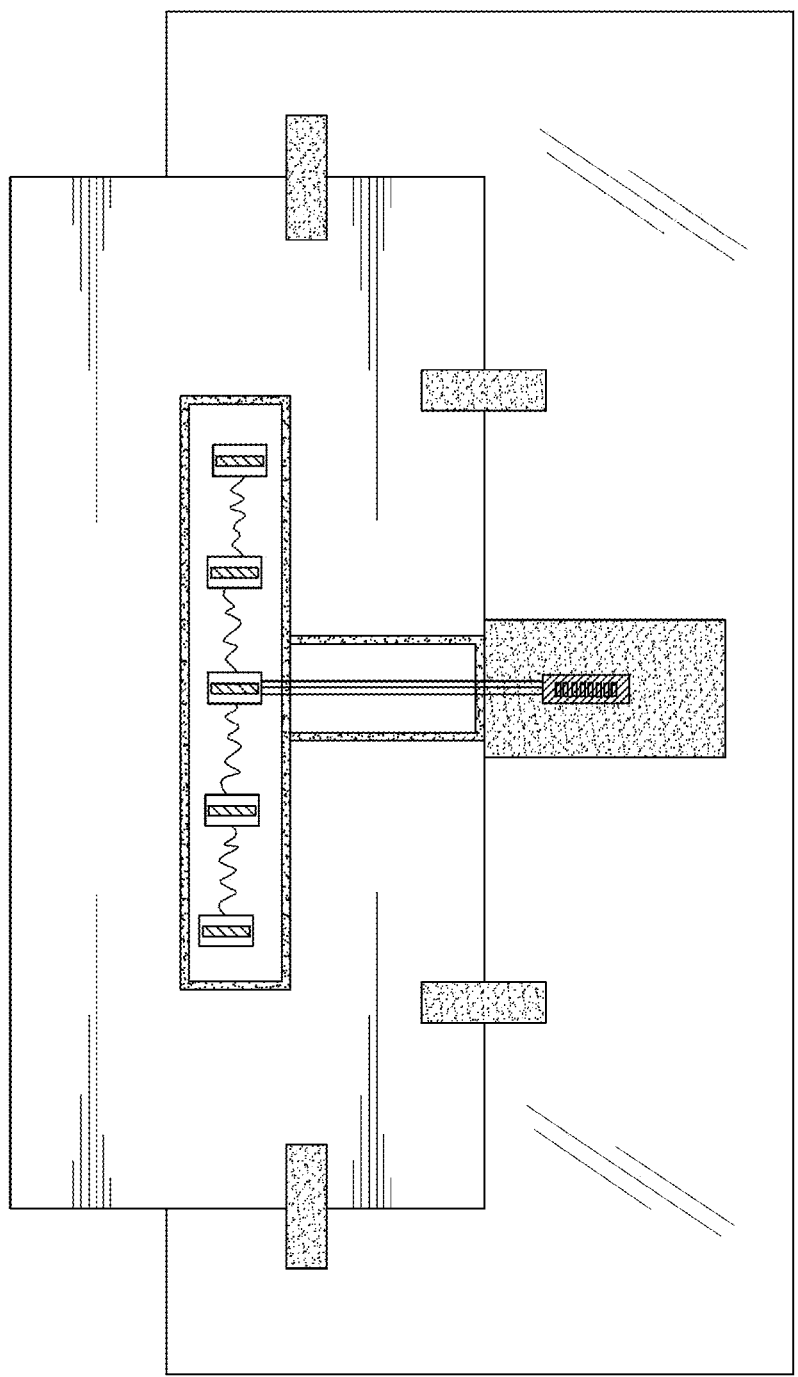

Block 7. As illustrated in FIG. 38, the contact pads are coated with adhesive. A thin coat of HYSOL® ECCOBOND® CE3126 (a heat curable anisotropic adhesive) can be applied over the electrode contact pads on the flexboard connection so that the pads are still be visible through the layer of ECCOBOND® adhesive.

Figure 39:
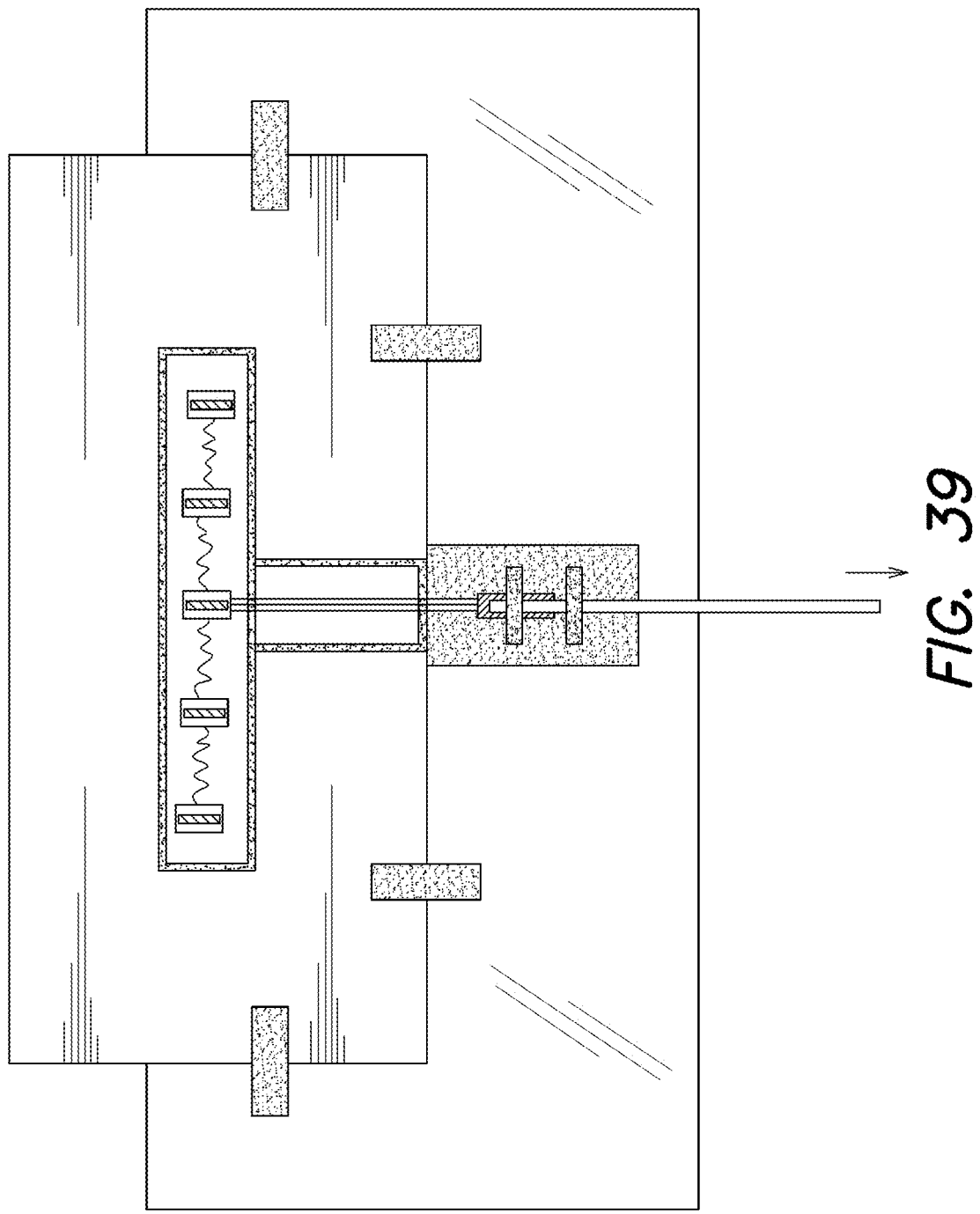

Block 8. As illustrated in FIG. 39, the flex board is attached to the electrode array. The flexboard can be aligned with the contact pads using the microscope. A PI tape can be applied horizontally over the flexboard to hold it in place over the contact pads.

Block 9. Proper alignment between the flex board connections on the electrode array and the flex board is verified. All contact pads should be aligned and not in contact with adjacent pads or connections. If alignment is not correct, and the process of FIG. 39 can be repeated.

Figure 40:
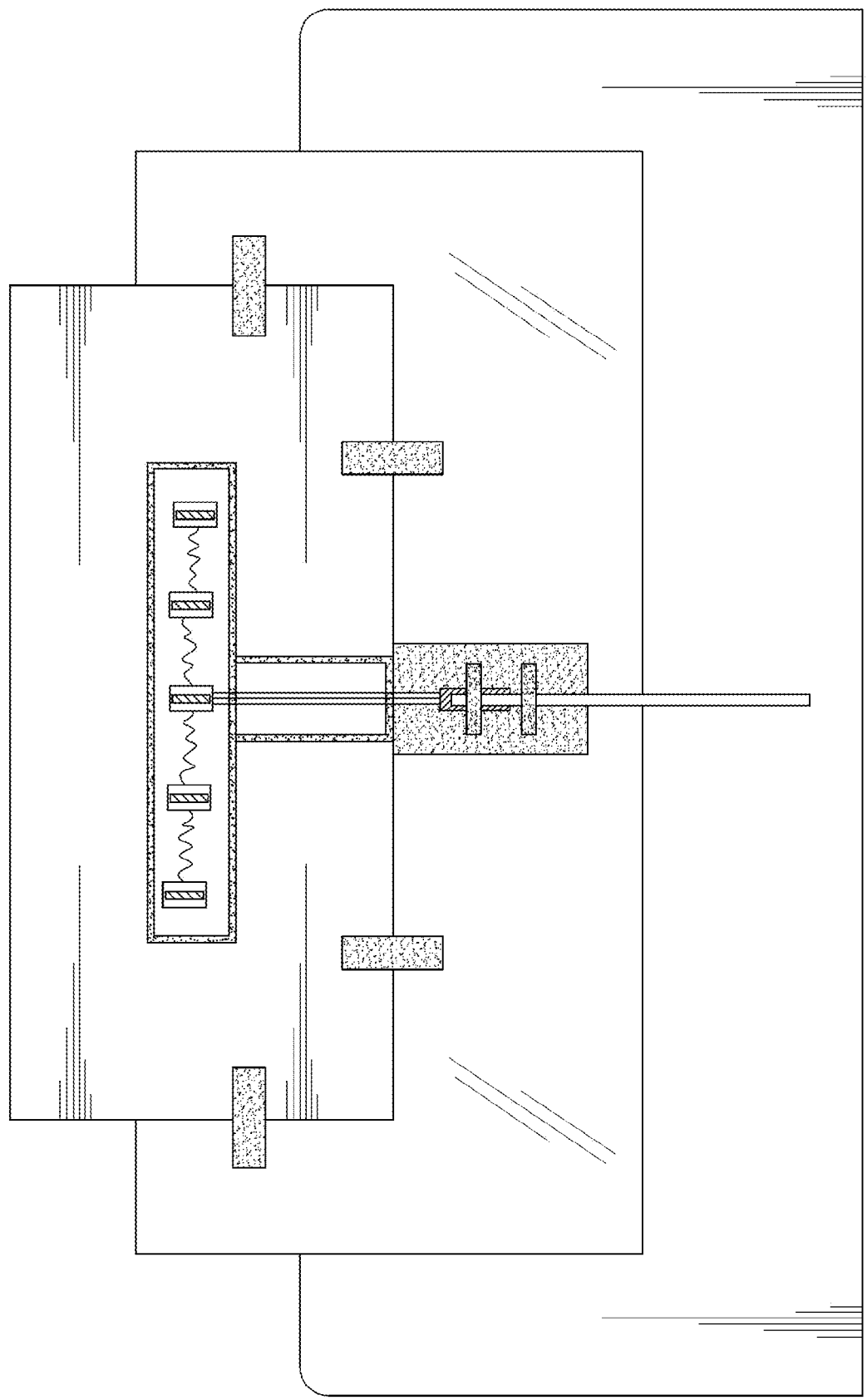

Block 10. The adhesive is cured, as illustrated in FIG. 40, at a temperature of about 170° C. Care should be taken not o shear the flexboard in any direction while the ECCOBOND® is going through the curing process.

Block 11. It should be determined if the ECCOBOND® is fully cured, i.e., there is not fluid movement about the flexboard. If the ECCOBOND® is not fully cured, block 10 can be repeated.

Figure 41:
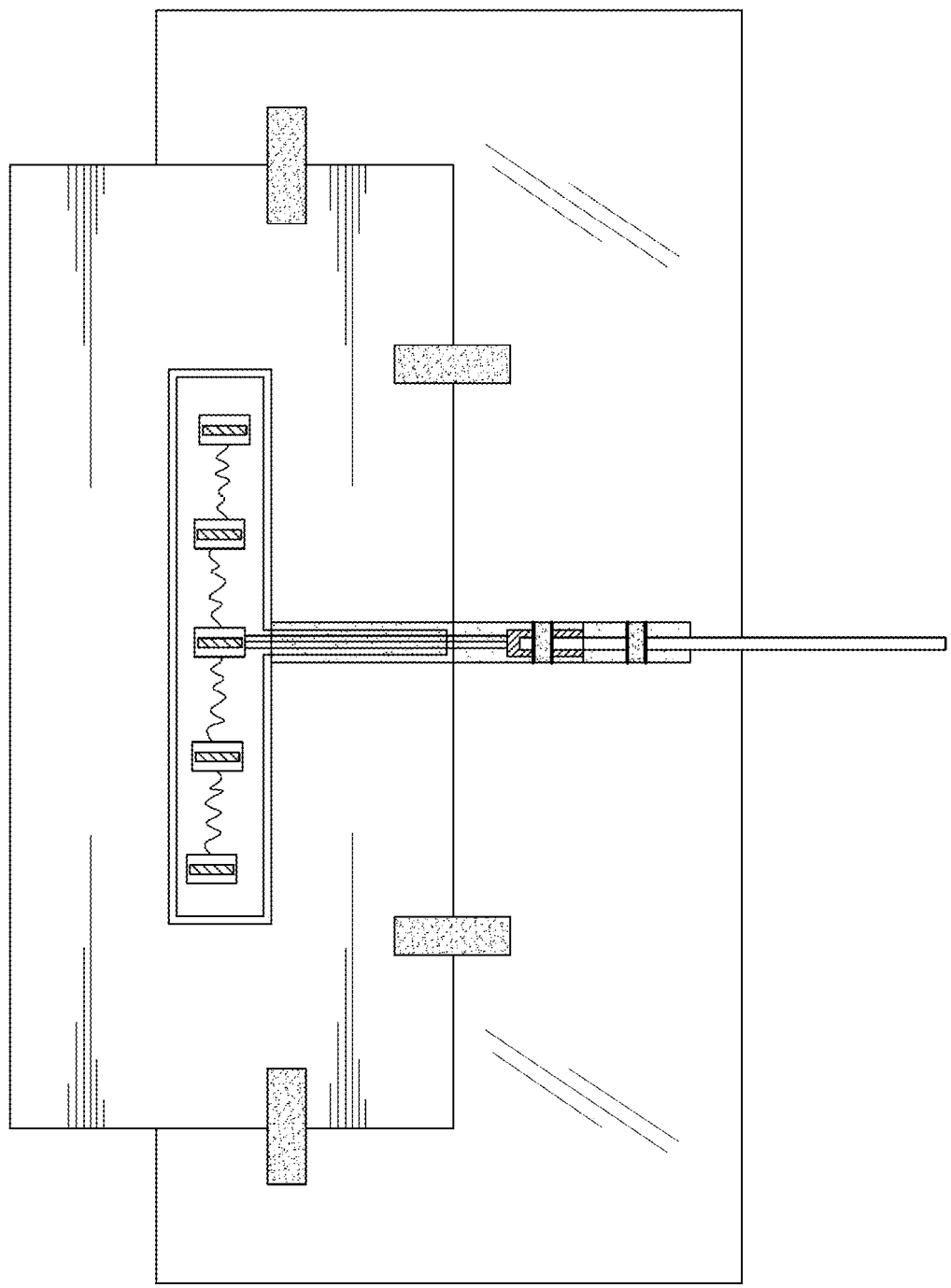

Block 12. The sensing elements array can be removed, as illustrated in FIG. 41. Excess soluble and PI tape can be removed from the edges of the "T" and flexboard to create a narrow outline around the electrode array.

Figure 42:
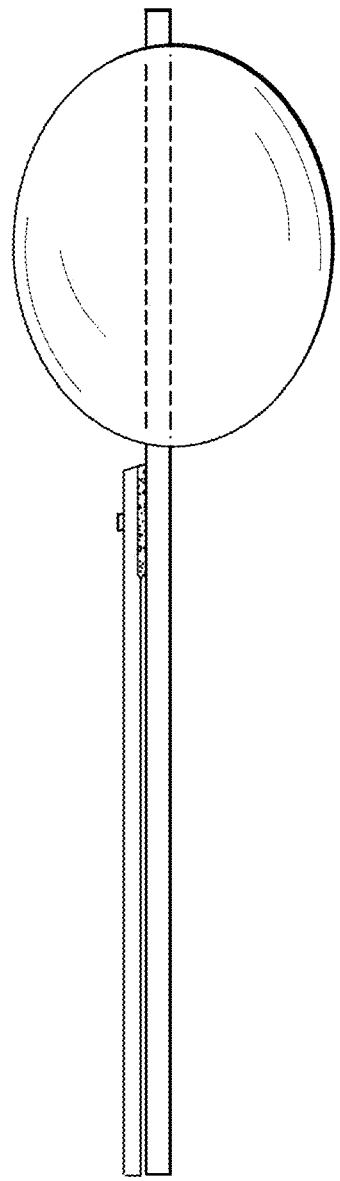

Block 13. The flexboard is attached to the balloon catheter, as illustrated in FIG. 42. In this example, the array is applied while the balloon is fully deployed. An epoxy is applied to the catheter shaft, as close to the balloon as possible. The neck of the T-shaped configuration is applied down the shaft of the catheter so that the "T" portion lies around the equator of the balloon. In an alternative example, the flex board can be adhered to the balloon catheter using PI tape, where the PI tape is placed as close to the balloon as possible.

Block 14. The sensing elements array is removed. The soluble tape is removed, with the array attached, from the flex metal and glass slide. The soluble tape remains on the catheter shaft.

Figure 43:
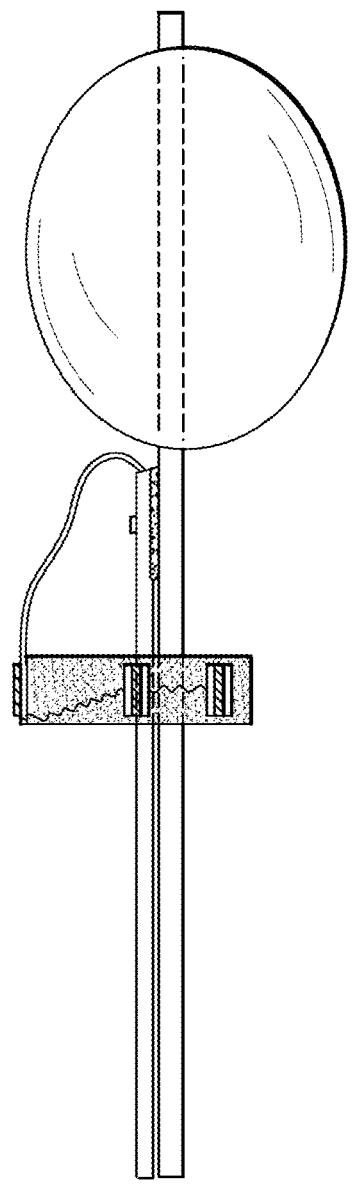

Block 15. An adhesive is applied to the sensing elements array, as illustrated in FIG. 43. As the sensing elements array is separated from the balloon, a flexible bond adhesive can be applied, such as but not limited to a 208CTHF Ultra LightWeld (sold from DYMAX®, flexible bonding adhesive) to the backside of the "T". A small injector tip may be used to apply the adhesive.

In an alternative example, DYMAX® bonding adhesive is applied to the balloon.

Figure 44:
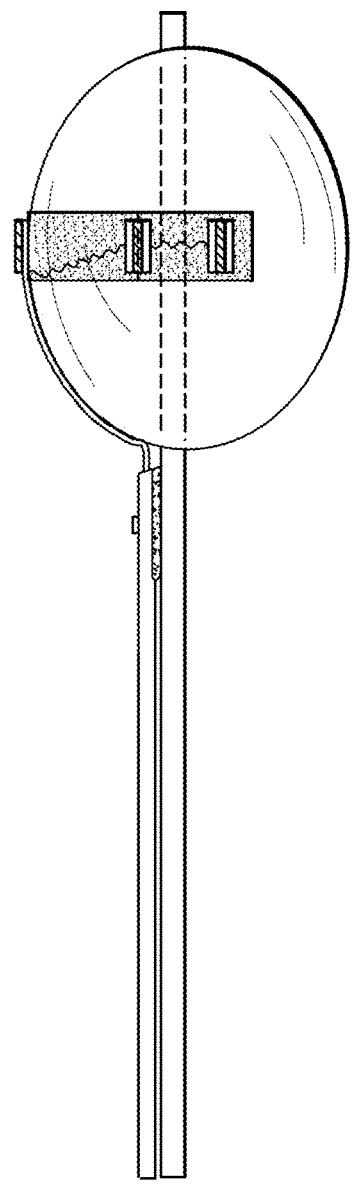

Block 16. Place the electrode array on the balloon surface, as illustrated in FIG. 44. The array is applied to the balloon, beginning near the shaft and working towards the equator. The arms of the "T" are wrapped around the balloon, making sure that the electrodes are aligned around the equator and that the soluble tape is completely flat around the balloon.

Block 17. The adhesive is cured. The DYMAX® adhesive is cured at about 630 mW/m$^2$. Each 5 mm$^2$ area can be exposed to UV light for about 15 seconds.

In an alternative example, a low intensity UV chamber can be used for curing. The integrated system can be slowly rotated in the presence of the low UV light for about 30 seconds. Contact with the UV light source or the UV chamber should be avoided. After curing, the DYMAX® should be allowed to dry.

Figure 45:
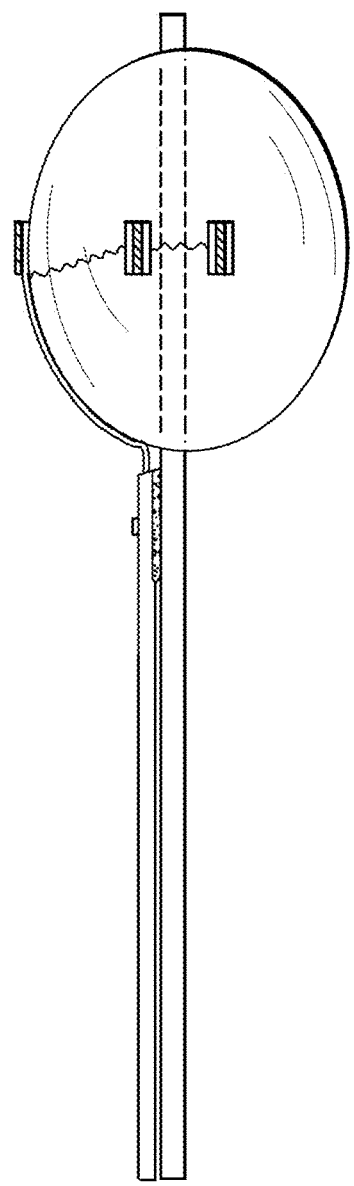

Block 18. The soluble tape can be dissolved, as illustrated in FIG. 45. The balloon is placed in a water bath at room temperature to dissolve the soluble tape on the surface of the balloon. Contact with the flexboard connection with the water bath should be avoided. The integrated arrays-balloon system can be dried at room temperature.

Block 19. Apply an additional encapsulation layer can be applied, such as but not limited to a DYMAX® encapsulation layer. The encapsulation layer ca be applied to cover the serpentine structures as well (including in the coupling bus and in the flexible interconnects). The sensing elements pads may not be coated with an encapsulation layer.

Block 20. The additional encapsulation layer may be cured.

Figure 46:
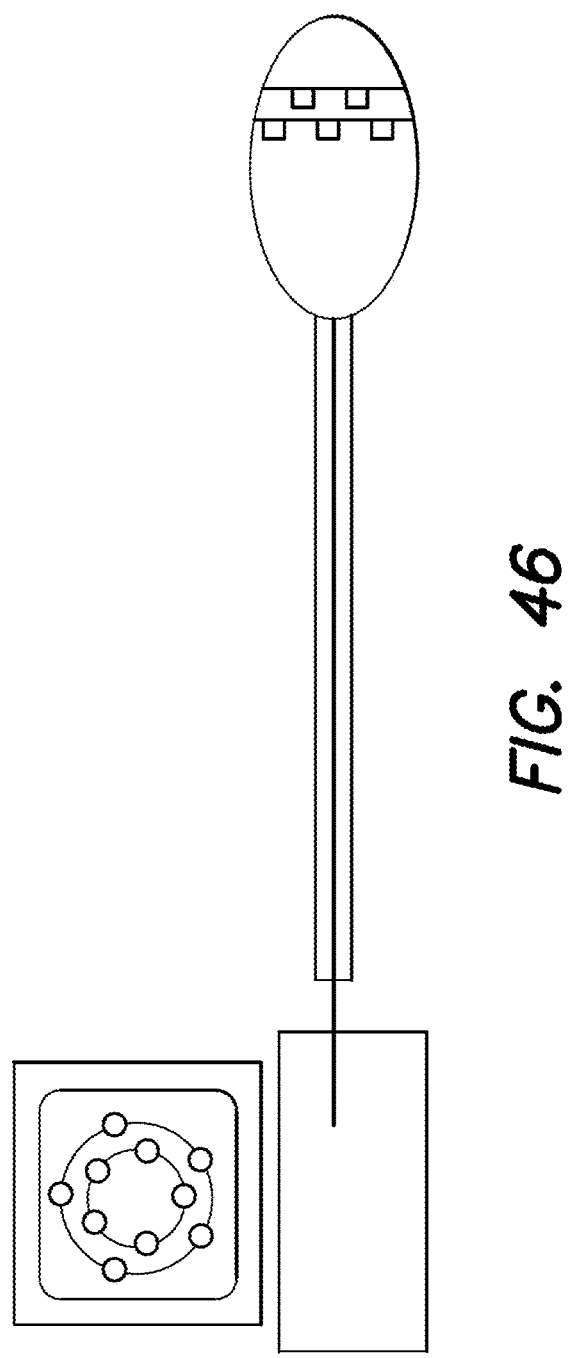
FIG. 46 shows a schematic example of a balloon catheter including integrating electrodes coupled with a data acquisition and graphical user interface, according to the principles described herein.

A non-limiting implementation is evaluated using a glass funnel apparatus to demonstrate feasibility. FIG. 46 shows a schematic example of a balloon catheter including integrating sensing elements coupled with a data acquisition and graphical user interface. In a non-limiting example, the sensing elements can be electrodes. A data acquisition system is implemented to support the sensing element to provide user feedback on the sensor sensitivity and speed. Once the sensing element fabrication is completed, contact sensing is evaluated in a glass funnel apparatus to demonstrate feasibility. Taken together, the designs, fabrication strategies and feasibility measurements provide insight into the optimal configuration of conformal sensors on the inflatable body (such as but not limited to a balloon catheter). The data acquisition and user interface associated with the conformal sensing elements provide real time data on the behavior of different physicians and quantitative metrics on their occlusion technique. This information may be viewed as a function of time and show occlusion success rates as they relate to procedure outcomes.

In an example implementation, the data acquisition system for impedance-based contact sensing elements includes a National Instruments data acquisition system, a data acquisition (DAQ) hardware/software module for data acquisition, and calibration references. Measurements of the calibration references can be used to determine threshold values for analysis of the measurements, according to the principles described herein. The excitation current from the current source passes through tissue to generate a voltage, which may then be measured with a National Instruments PXI-6289 data acquisition card. LABVIEW® software (National Instruments Corporation, Austin, Tex.) can be used to control the output current and frequency of the excitation current. For the measurement, the excitation current may be set at 10 µA and measurements are taken at 1 kHz and 10 kHz. One function of the DAQ can be to display real-time contact data from the inflatable body in a manner that allows the user to interpret whether occlusion of the pulmonary vein has been achieved or not. In an example, a display separate from the data acquisition system can be used. To achieve a data acquisition system with a simple user-interface, binary (semi-quantitative) and quantitative (bar plots) representations of changes in impedance are used to facilitate visualization of an amount of contact across the sensors of an example system. In the binary representation, a baseline threshold is set based on the impedance measured in saline when the balloon sensors are floating. The threshold is set to about 1.5× to follow the larger impedance of tissue relative to that of blood. As a result, the balloon sensor nodes turned from gray to blue, denoting good contact (rise in impedance of greater than about 1.5× relative to the baseline impedance).

Figure 47:
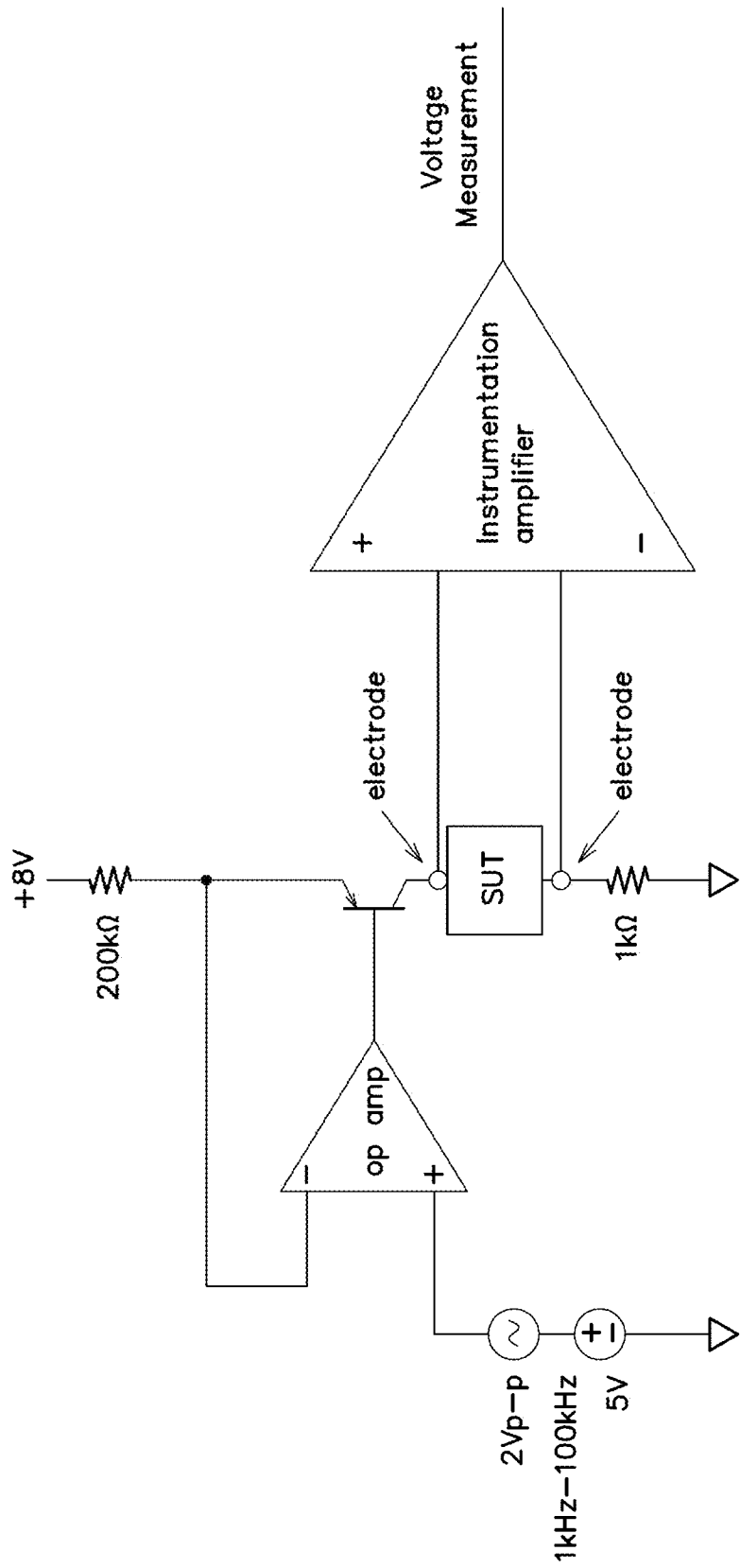
FIG. 47 shows an example circuit diagram of a unidirectional constant current source used for impedance measurements data, according to the principles described herein.

FIG. 47 shows an example circuit diagram of a unidirectional constant current source used for impedance measurements data according to principles described herein.

Figure 48:
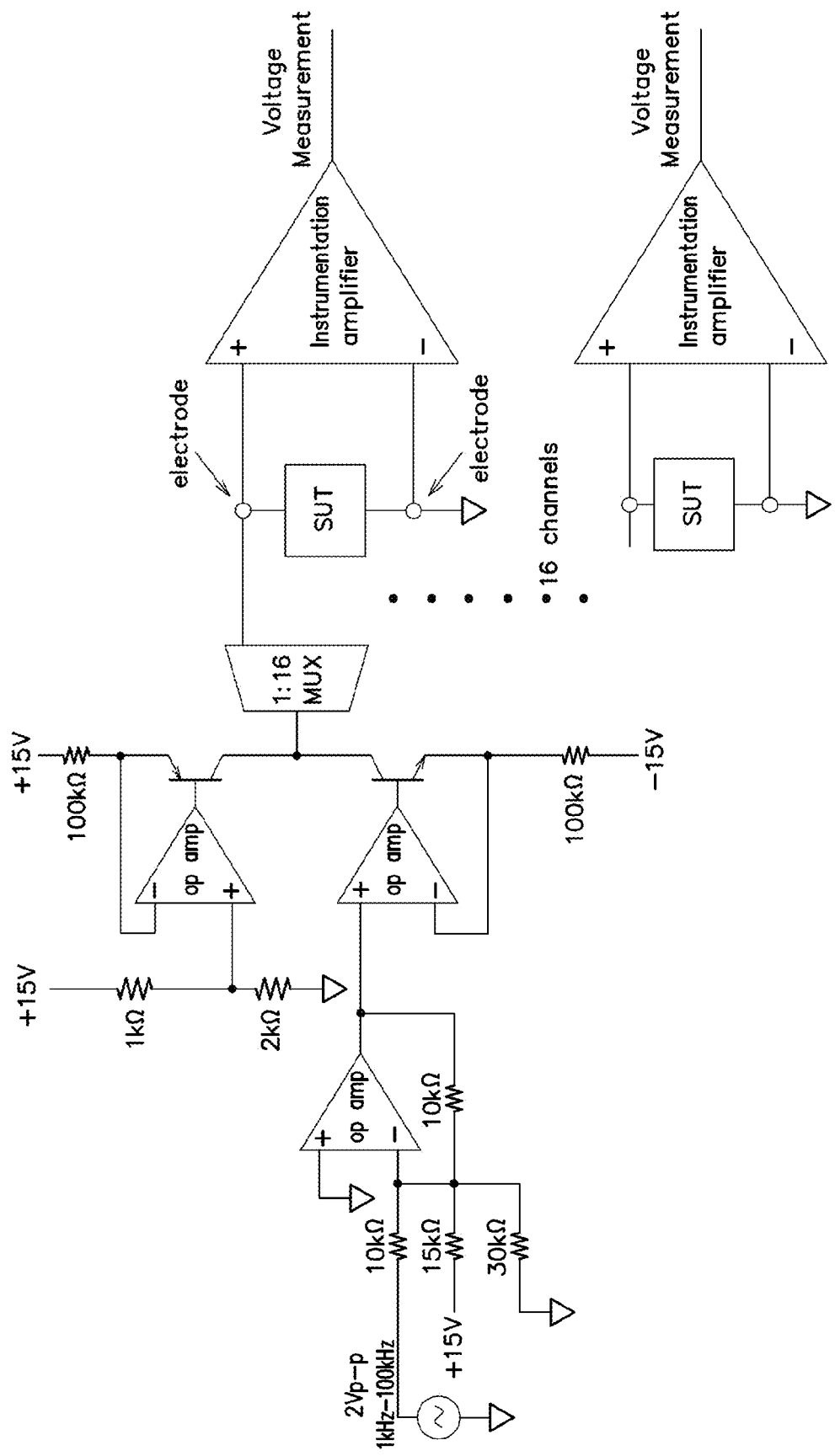
FIG. 48 shows an example circuit diagram of a bidirectional, low distortion current source used for impedance measurements data, according to the principles described herein.

FIG. 48 shows an example circuit diagram of a bidirectional, low distortion current source used for impedance measurements data according to principles described herein. FIG. 48 shows an example circuit diagram of 10-channel sensing elements (such as contact sensing elements array). A voltage can be measured across the same two terminals where constant current is applied (~3 kHz).

The circuits shown in FIG. 47 and FIG. 48 are voltage controlled current sources. The current passes through either blood or tissue. The resulting voltage may differ depending on whether it is the current passed through blood or tissue. Accordingly, the characteristic impedance can differ and it can be determine if a balloon catheter is in contact with tissue or blood based on impedance measurements. In one example, a factor of two (2) difference in impedance can be measured. This difference can be sufficient for measurements during contact/no contact cycles.

An example system, impedance Proto 1 shown in FIG. 47, is a unidirectional constant current source. It can be used to provide a high impedance node to the tissue (referred to as "subject under test" SUT). The high impedance node allows for a controlled amount of current to excite the tissue (SUT).

An example system, impedance Proto 2 shown in FIG. 48, is a bidirectional, low distortion current source. It can be used to drive multiple channels (in this example, 16 are shown). The output can be multiplexed so one channel sees 10 μA at any given time, which follows the IEC60601 safety guidelines. This can prevent cross-talk between channels and also can create a level of safety because the circuit delivers a known regulated amount of current to a particular channel at a given time.

Impedance Proto 2 of FIG. 48 can be used to keep both N and P output transistors biased so that it operates in the linear region. By steering current with the N transistor, the high frequency signal can be passed into the MUX, which then passes it to 1 of 16 channels to the SUT. In addition, this output stage has high linearity, which is helpful when driving the SUT at higher frequencies.

In addition to adhering to a current limit, both circuits are galvanically isolated, using an isolating transformer for example, from the power mains.

The voltage measured across the SUT yields real and imaginary values. Both characteristics can be taken into account to discern between blood and tissue. Analog and digital filtering can be applied to eliminate noise artifacts that include 50/60 Hz line noise and electromagnetic interference from other instruments in the operating room. A low pass filter can be employed to eliminate the high frequency noise.

FIG. 49 provides a series of screen shots of a graphical user interface demonstrating a variety of conditions simulated with a balloon catheter including integrated sensing electronics positioned in a glass heart.

The flex ribbon can be used to establish an interface with the sensing elements and a data acquisition system. The conformal sensing elements can interface with an intermediate wires or flex ribbon in order to transmit data to a data acquisition system. To achieve this interconnection, flex ribbons can be used that have thin and narrow width profiles to transmit data along the slender catheter and out to the data acquisition system console. Custom bonding can be used to control pressure and temperature, set over a small range to achieve a robust electrically continuous interface. The devices can be routed along the shaft. Heat shrink can be used as insulation to shield the flex ribbon connections from the fluid environment inside the body.

An impedance can be measured upon insertion and inflation of the inflatable balloon (in this example, a cryoballoon) within a lumen. In the example of FIG. 49, the cavity of a glass funnel (~50 mm outer conical diameter) immersed in saline buffer solution (phosphate buffer solution) is used as a demonstration of a tissue lumen. The apparatus includes a thermal regulator/circulation unit to maintain body temperature in the bath. FIG. 49 shows representative data from conformal sensors nearby (no contact state) and in good contact with the funnel. The funnel test shows impedance values on the order of 10-15× greater during contact state relative to impedance of floating catheter in saline. Although tissue impedances are significantly smaller than that of glass, this initial study validated the concept of embedding contact sensors on the inflatable body (such as the cryoballoons).

The measurements of conformal sensors are provided to a data acquisition console to make measurements in an elastomeric phantom heart model. A catheter (n=7) in a phantom heart model can be deployed coupled with a 14 F sheath access port. This initial study is used as a way to evaluate encapsulation polymers and durability of the conformal sensors on the balloon. Initial results with UV-curable polymer adhesives showed significant delamination upon entry into the phantom left atrium. With usage, some delaminations of the serpentine buses and contact sensor pads may occur. In various examples, different types of polyurethane encapsulants can be used to enhance the mechanical stability of the serpentine buses and contact sensor pads., promoting greater durability while preserving stretchability, transparency, and biocompatibility.

Use of an encapsulant according to the principles herein, in addition to enhancing delamination, reduced the thermal effects of having conformal sensors on the balloon during cryoablation and minimized the effect of cryo-thermal cycling on performance of the sensing elements. The results demonstrated minimal changes in thermocouple measurements for cryoballoons with embedded sensors relative to those without, indicating that the conformal sensors minimally act as thermal sinks. Cryothermal cycling is conducted using an alcohol bath adjusted to −56° C. Cryoballoons with conformal sensors exposed to this temperature over many cycles at 4-minute intervals. No changes are seen in sensor optical characteristics and overall performance following this testing. These results indicate that repeated exposure to cryoenergy does not affect the performance of conformal sensors on the cryoballoon. Other catheter features, including mechanical deflection, sheath deployment and shaft size, are all examined to understand the impact of contact sensors on the overall look/feel and performance of the cryoballoon with embedded contact sensors.

To establish a robust quantitative means of assessing occlusion, the changes in impedance measured during cryoballoon occlusion in the right superior PV (RSPV) can be assessed. The results provide, for the first time, a new way to assess occlusion while concurrently allowing the collection of new data on the behavior and successes of individual cryoballoon operators. These behaviors are evaluated during occlusion prior to ablation and during cryoenergy injection.

The cryoballoon contact is measured using impedance in a tissue lumen of live pigs by deploying inflatable bodies with contact sensors through a 14 F sheath into the left atrium. Tests show sensors can assess contact with PV ostium immediately prior to cryoablation.

FIG. 50 provides a series of screen shots of a graphical user interface demonstrating a variety of contact conditions with a balloon catheter including integrated sensing electronics positioned in a tissue lumen of a live pig.

Shifts in impedance caused by tissue contact are observed using impedance-based contact sensors. FIG. 50 shows results from a left superior pulmonary vein of a pig heart whereby contact is achieved across all active sensors and confirmed with injection of contrast dye. Impedances can be approximately 1.5-2.0× greater when the cryoballoon is in good contact. These measurements are reproducible across two different pig measurements and across multiple trials runs in each animal.

The state of the contact sensors is assessed during cryoablation by first establishing adequate occlusion. Once occlusion is confirmed, cryoenergy is applied and changes in impedance are tracked over the course of 15-second intervals. The reaction of the conformal sensors is assessed since cooling happens gradually over 2-3 min time intervals. Impedance gradually rose by up to 25× across the active sensors. This result highlights a second use-case scenario for impedance-based contact sensing whereby changes in impedance can track occlusion.

In the case where there may be a gap (poor occlusion), the sensors aligned with regions of good occlusion freeze over (causing significant rise in impedance) while those near the gap experience heating effects due to flow of blood (causing an insignificant rise in impedance). This outcome is tested in a few cases where a few of the sensors are occluded while others remained in poor contact. In this particularly case a few of the sensor provided sensor results indicated that the sensors were occluded. This particular case shows how contact sensors on a balloon can be used as a substitute for evaluating occlusion without use of x-ray imaging.

Baseline impedance during contact can depend on salt concentration. Although impedance-based contact sensors are free from hysteresis effects, they can cause variability based on the ionic concentration of the media. As a result, baseline impedance values could vary depending on the salt concentration of blood relative to cardiac tissue or saline. The most significant challenges are in establishing the baseline levels upon deployment of the catheter in heart. Once this baseline is established, occlusion is then quickly assessed upon balloon maneuvering. Baseline automation strategies in software/DAQ data acquisition system console can be implemented as a way to estimate baseline levels across individual sensors once the cryoballoon inflates in the atria.

FIG. 50 demonstrates an example user interface displaying binary read outs of sensors disposed on a balloon catheter. In the example of FIG. 50, each circle corresponds to a sensing element, and provides a representation of a state of the sensing element. In this example, an open circle on the display corresponds to no contact between a sensing element and the tissue, and the shaded circle indicates an amount of contact between a sensing element and the tissue.

Figure 51A:
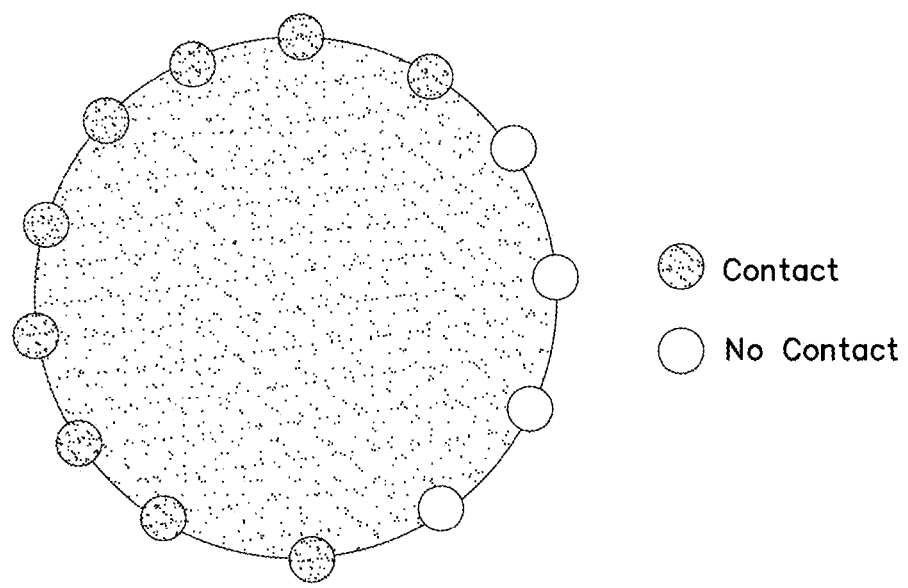
FIGS. 51A and 51B illustrate example visualizations of contact sensing from measured data, according to the principles described herein.
Figure 51B:
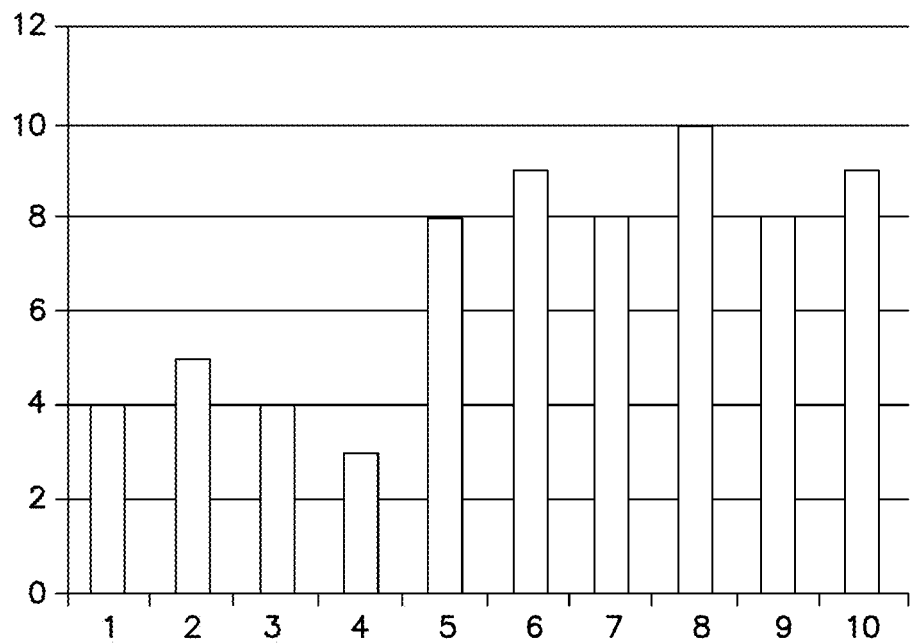

FIGS. 51A and 51B illustrate another example a visualization of contact sensing from measured data. Such visualization can help personnel in making assessments on occlusion. Specifically, FIG. 51A is a simplified representation of the balloon cross section. Through color or texture of the small circles representing each sensor, the example user interface can be used to indicate whether a sufficient contact force is experienced by a given sensing element. For example, a measured value of the sensing element above a threshold value can be decided as an indicator that the sensor has established contact with a portion of tissue, a measured value of the sensing element below the threshold value can be decided as an indicator that the sensor has not established contact with a portion of tissue. FIG. 51B is an example chart representation of a measure of contact force experienced by each sensor.

While the user interface of FIGS. 50, 51A and 51B are described in terms of indication of contact force between the sensing elements and the tissue, the user interface and visualization technique can be applied to display the results of other measurements, including impedance, temperature, pressure, or any other type of measurement that sensing elements according to the principles herein can be used to measure.

Figure 52:
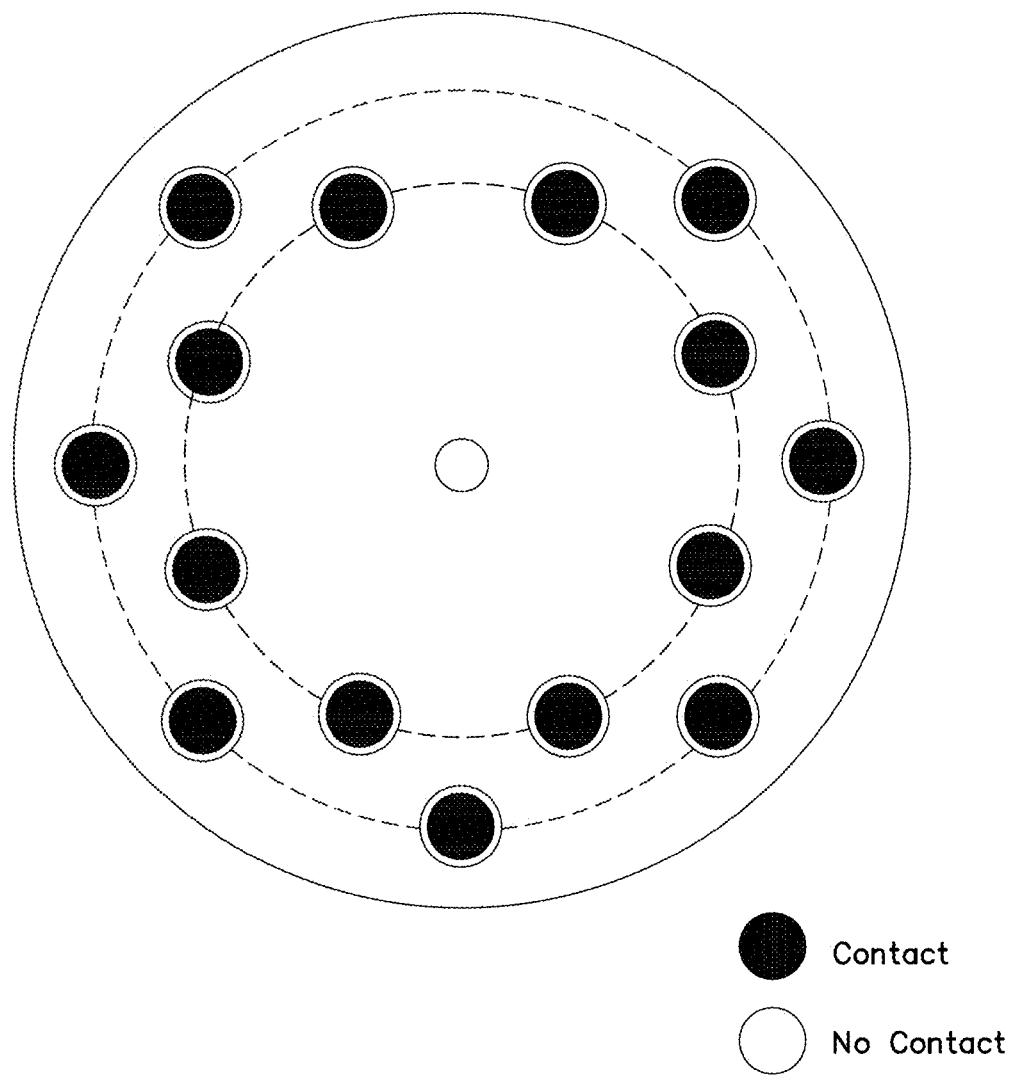
FIG. 52 demonstrates another example user interface displaying binary read outs of sensors disposed on a balloon catheter, according to the principles described herein.

FIG. 52 demonstrates another example user interface displaying binary read outs of sensing elements disposed on an inflatable body (here a balloon catheter). In this example, an open circle on the display corresponds to no contact between a sensing element and the tissue, and the shaded circle indicates an amount of contact between a sensing element and the tissue FIG. 53 demonstrates an example user interface displaying quantitative read outs of sensing elements disposed on an inflatable body (here a balloon catheter In this example, a length of an arrow at each sensing element representation serves as an indicator of the amount of a measurement from the respective sensing element.

Figure 54:
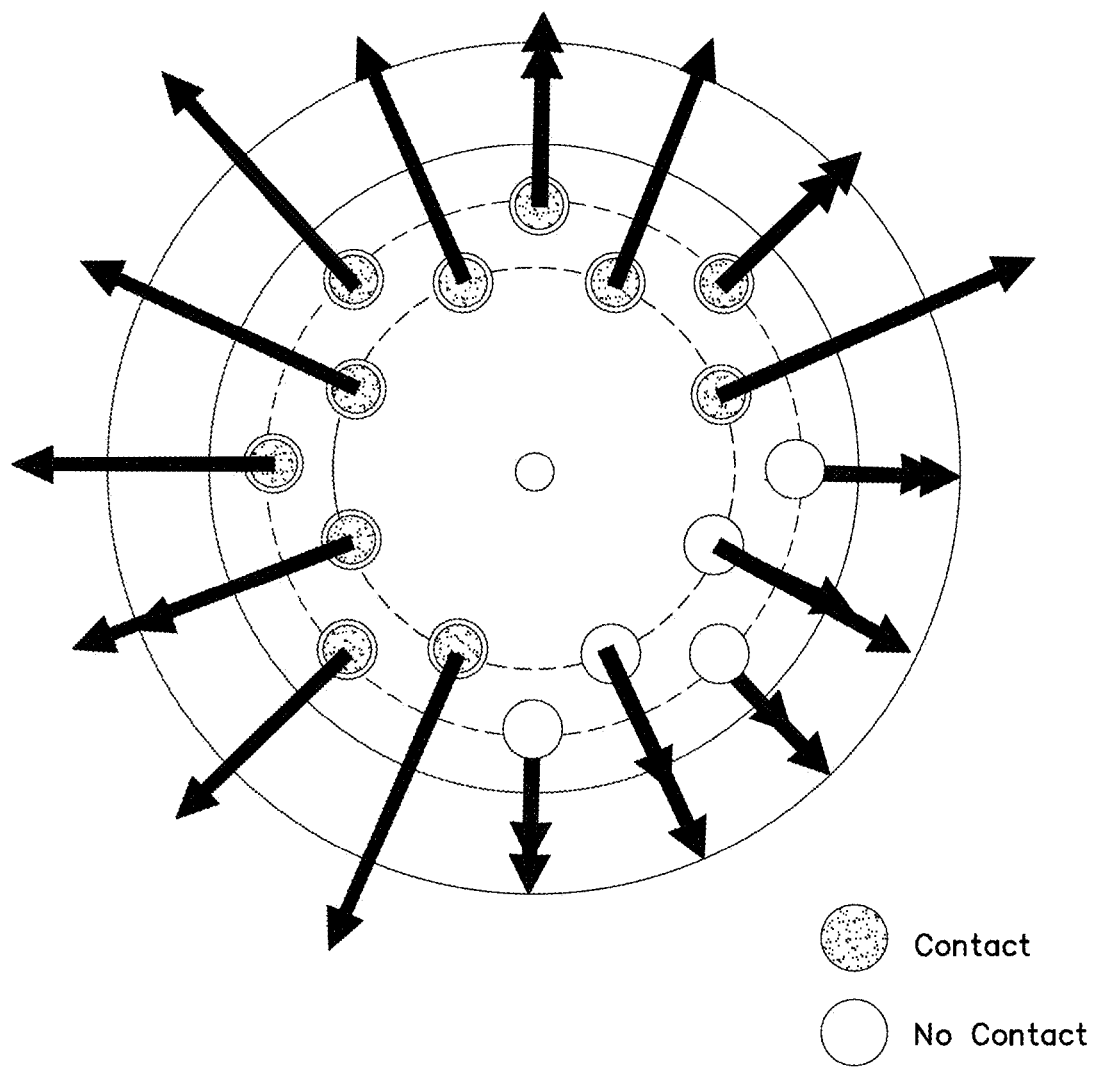
FIG. 54 demonstrates another example user interface displaying quantitative read outs of sensors disposed on a balloon catheter, according to the principles described herein.

FIG. 54 demonstrates another example user interface displaying quantitative read outs of sensors disposed on a balloon catheter. In this example, the sensor representations are arranged in two different diameter circles, which can be used to indicate the spatial distribution of the sensing elements on the inflatable body. For example, the sensing element representations in the smaller circle can be used to indicate measurements of sensing elements disposed closer to a top portion of the inflatable body; the sensing element representations in the larger circle can be used to indicate measurements of sensing elements disposed farther from the top portion of the inflatable body. In this example, a length of an arrow at each sensing element representation serves as an indicator of the amount of a measurement from the respective sensing element. A measurement below a threshold value can be classified as no contact, while a measurement above the threshold value indicates an amount of contact.

Figure 55A:
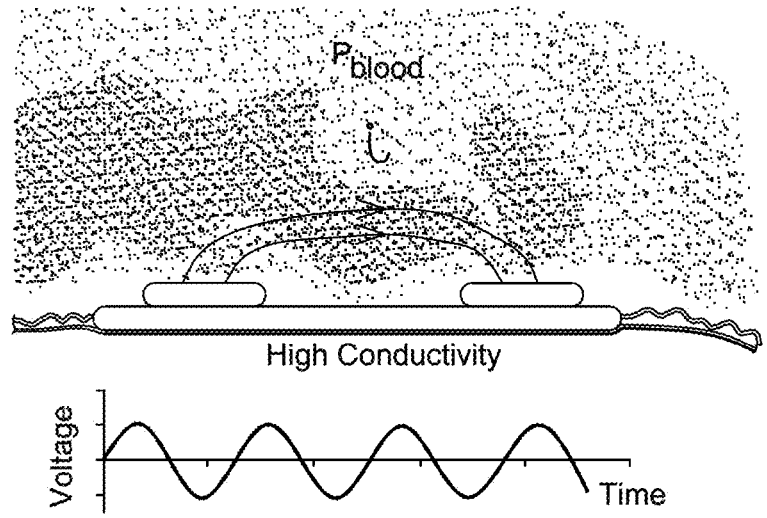
FIGS. 55A-55B illustrates an example determination of whether contact is made to blood or tissue based on changes in electrical conductivity or resistivity, according to the principles described herein.
Figure 55B:
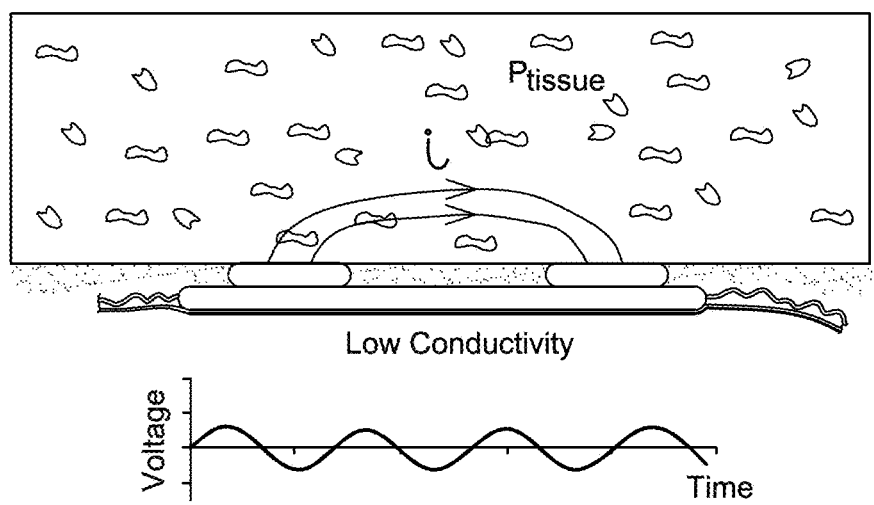

FIG. 55A-55B illustrate the principles of determining whether contact is made to blood or tissue based on changes in electrical conductivity or resistivity. FIG. 50 illustrates the principles of determining whether contact is made to blood or tissue based on changes in electrical conductivity or resistivity. Specifically, because the blood has a higher resistivity than tissue ($\rho_{blood} > \rho_{tissue}$), using the constant voltage sources illustrated in FIGS. 47 and 48, a greater voltage across electrodes is measured when they are in contact with blood as compared with when they are in contact with tissue. As shown the measured voltages result from AC current injection at a predetermined frequency.

Figure 56:
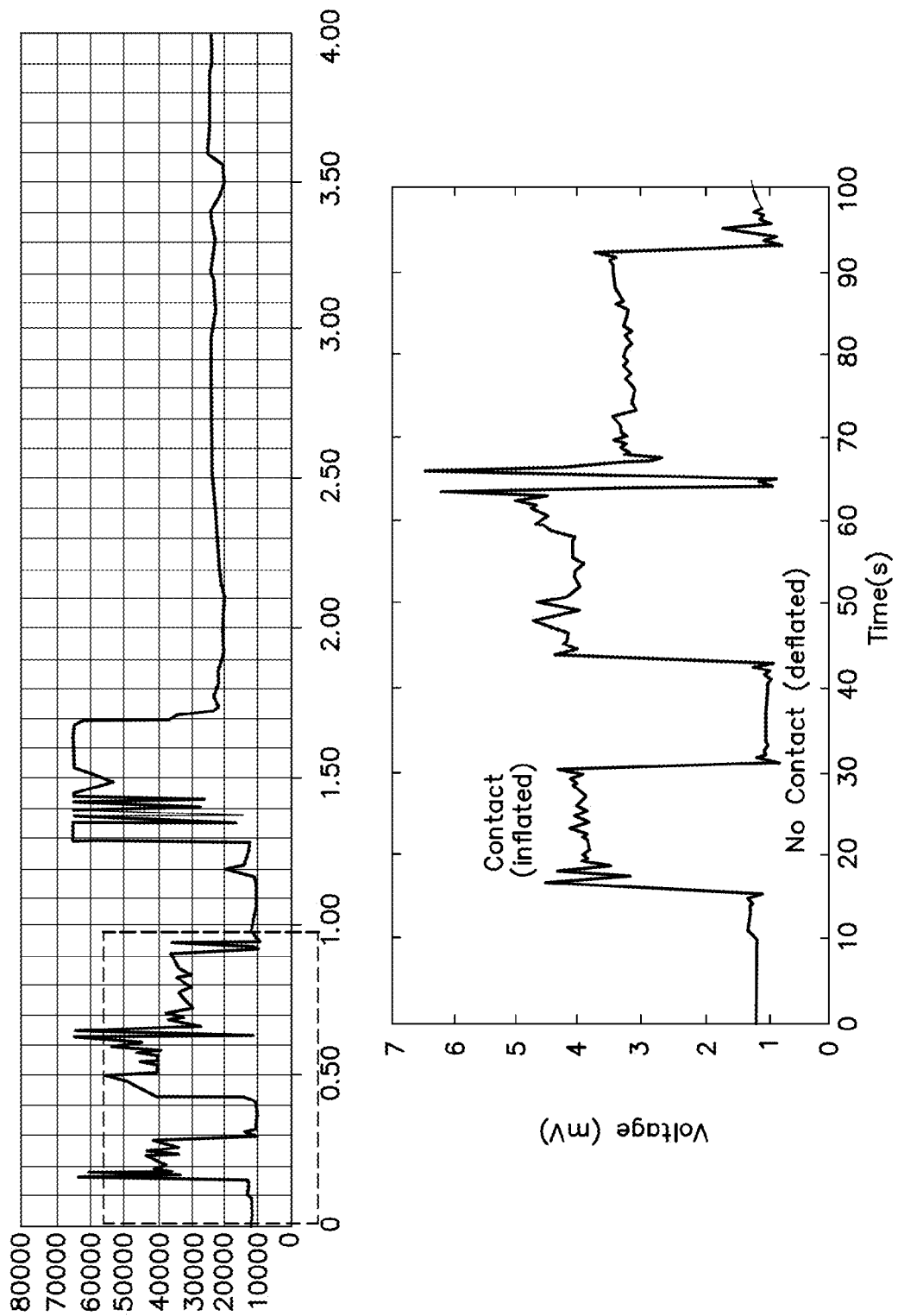
FIG. 56 shows example pressure sensitive resistor (PSR) contact sensor in inferior vena cava/superior vena cava (IVC/SVC) data, according to the principles described herein.

FIG. 56 shows example PSR contact sensor in IVC/SVC data. The plot shows values of measurements that are determined to indicate no contact or contact. In this example, a measurement above a threshold value of around 1.5 mV are taken to indicate contact between a sensing element and an inflatable body. The example results show that PSR contact sensors tracked contact and non-contact settings but can be unstable compared to in vitro recordings.

Figure 57:
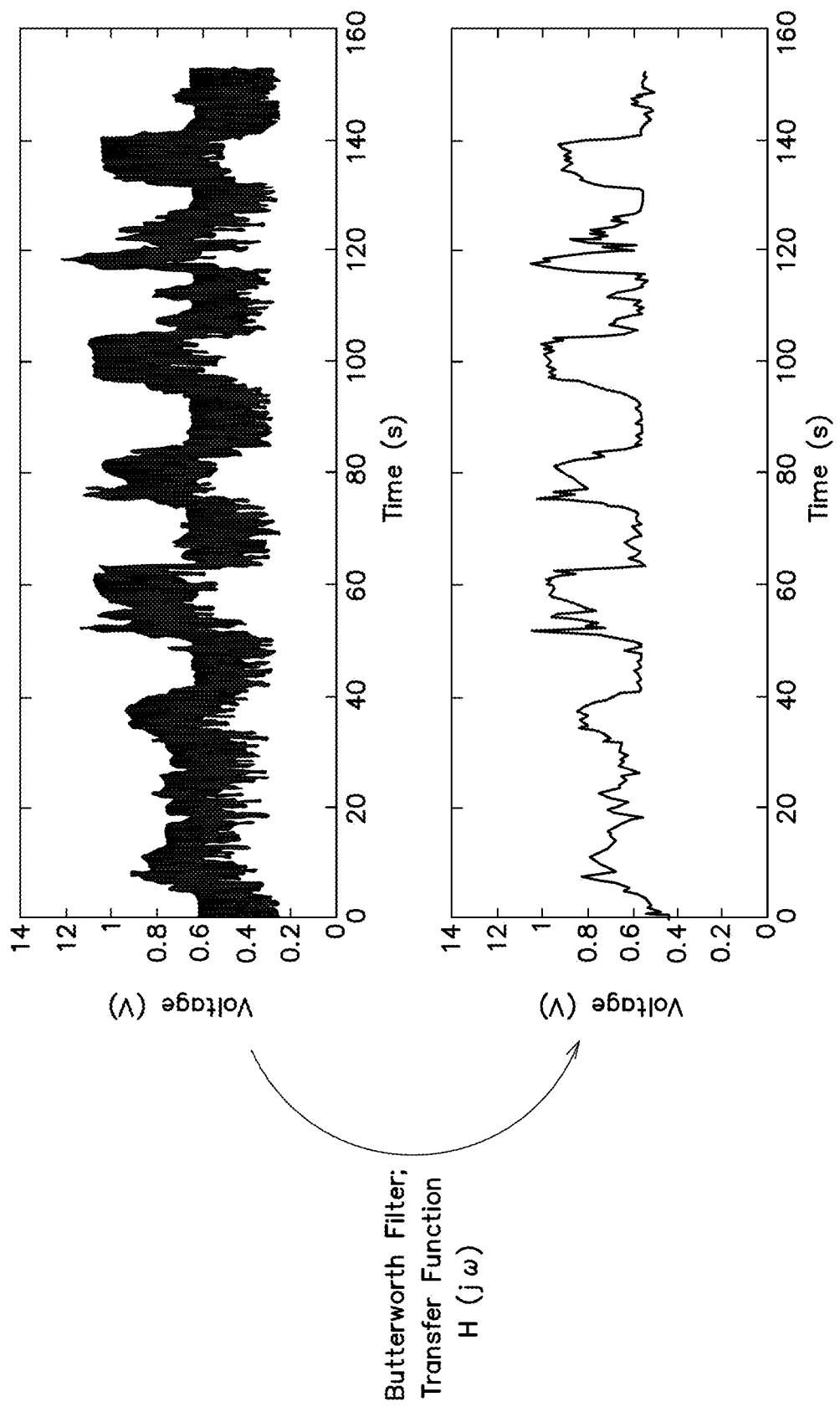
FIG. 57 illustrates example electrical impedance tomography (EIT) contact sensors in IVC data, according to the principles described herein.

FIG. 57 illustrates example filtering of EIT data. FIG. 53 illustrates filtered EIT data, where a low-pass Butterworth filter can be used to improve signal quality without sacrificing contact information. For example, a filter can be applied to measurements to extract signal from the sensing elements from the noise in the measurements.

Figure 58:
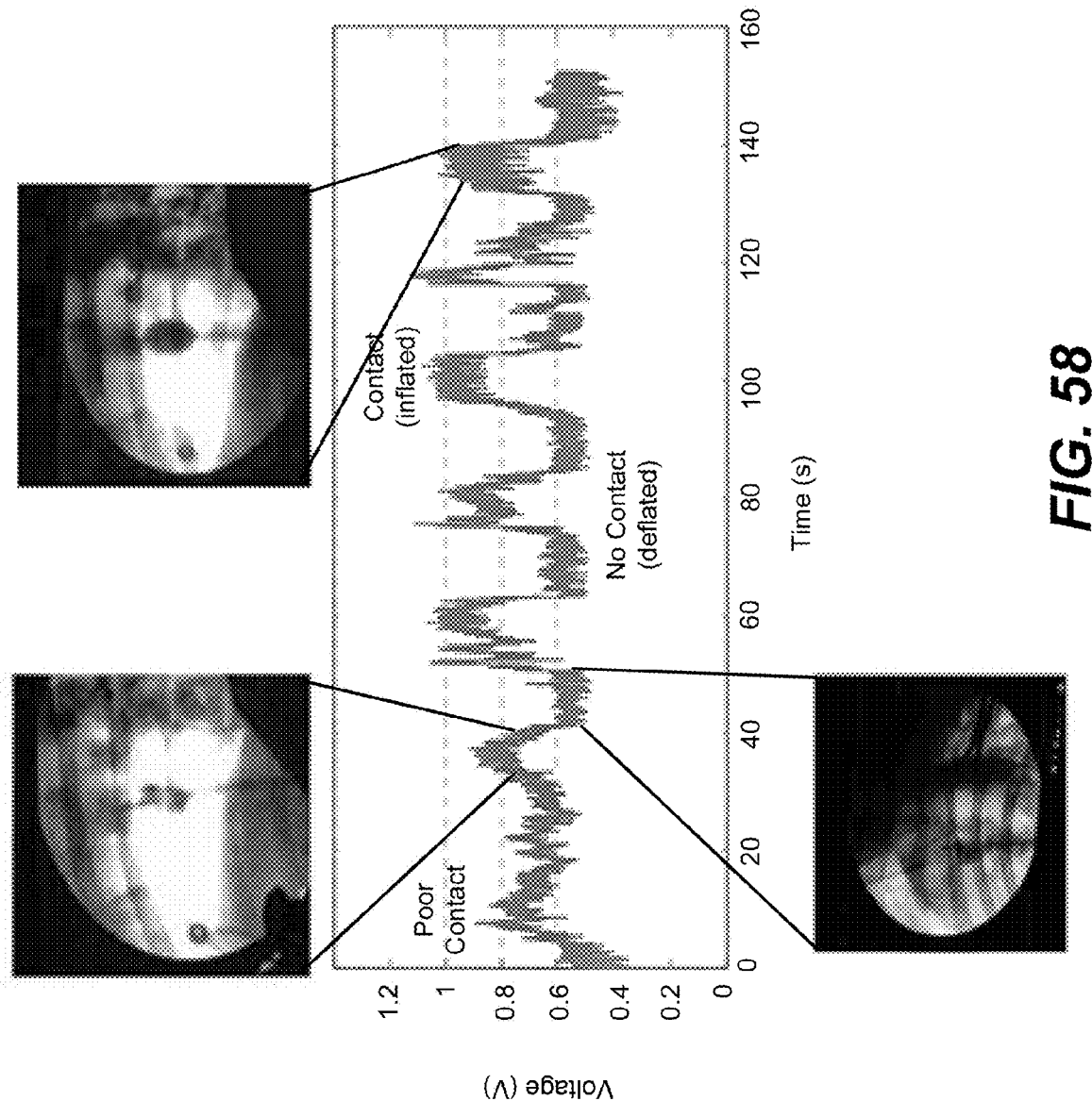
FIG. 58 illustrates example filtered EIT data, according to the principles described herein.

FIG. 58 illustrates example EIT contact sensors in IVC data. In this example, it is shown that measurements from sensing elements configured as EIT sensors can be used to distinguish among sensing elements that are in contact, no contact, or poor contact states in IVC. For example, a measurement below a first threshold value can be used to indicate a state of "no contact" for a sensing element. In this example, a value below about 0.6 mV is determined as an indicator of "no contact." In another example, a measurement above a second threshold value can be used to indicate a state of "contact" for a sensing element. In this example, a value above about 0.8 mV is determined as an indicator of "contact." In another example, a measurement between the first threshold value and the second threshold value can be used to indicate a state of "poor contact" for a sensing element. In this example, a value between about 0.6 mV and about 0.8 mV is determined as an indicator of "poor contact."

Figure 59C:
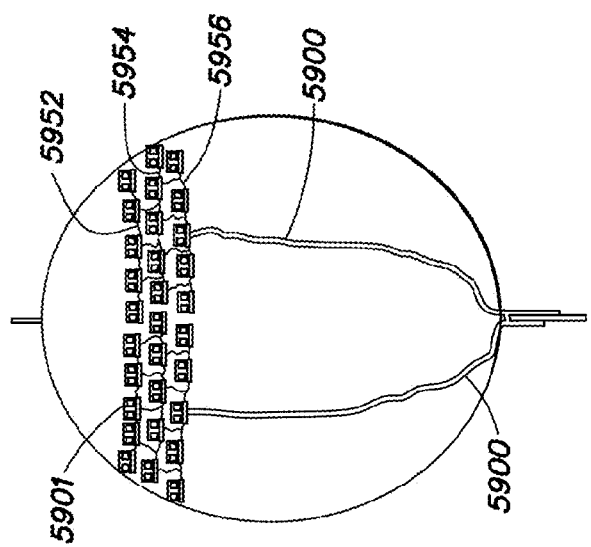
FIGS. 59A-59C illustrates additional examples of the sensor configuration on the balloon surface, according to the principles described herein.
Figure 59B:
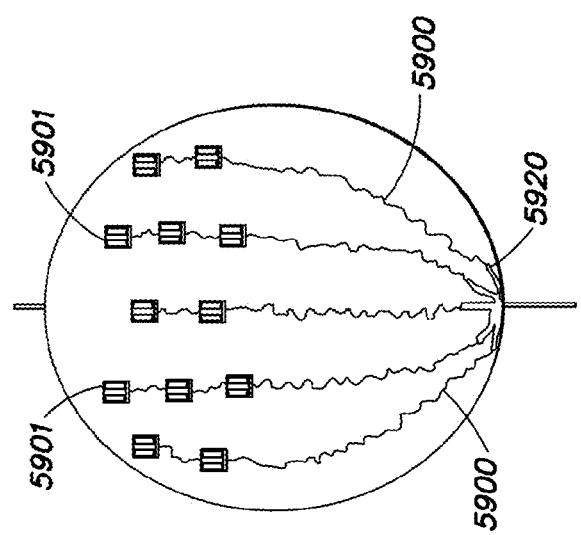
Figure 59A:
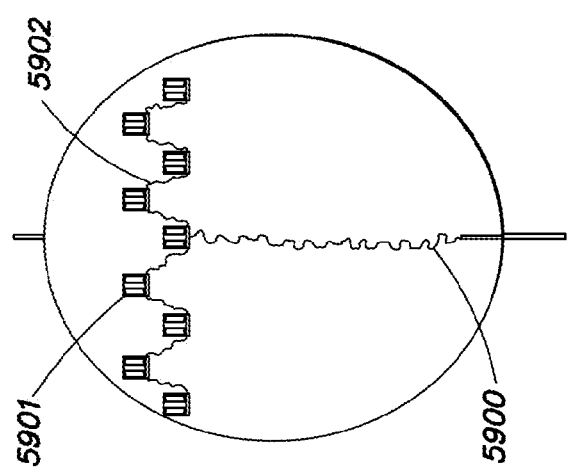

FIG. 59A-59C illustrates additional examples of sensing elements configurations on the balloon surface, according to the principles described herein. Multiple independent flex boards can be used to increase the total number of sensors. For example, FIGS. 59A-59C illustrate that the flexible interconnects 5900 leading from the sensing elements 5901 can be routed down towards the base of the inflatable body. FIG. 59A shows the sensing elements 5901 can be disposed along two different latitudes of the inflatable body, and the coupling bus 5902 can run sequentially from a sensing element at one latitude to a sensing element in another latitude. FIG. 59B shows that the flexible interconnect 5900 can be routed down towards the base of the inflatable body where a coupling bus 5920 may be located. FIG. 59C shows an example that includes more than one coupling bus. In this example, there are three coupling buses 5952, 5954, 5956, each associated with a different latitude of the inflatable body. In this example, the sensing elements 5901 are disposed along each of the three different latitudes of the inflatable body, and the sensing elements 5901 along each latitude are connected with a respective coupling bus.

FIGS. 60A-60B illustrates further additional configurations of the sensing elements array, including "L" shaped arrays, according to the principles herein. For example, FIGS. 60A-60B illustrate that the flexible interconnects 6000 leading from the sensing elements 6001 can be routed down towards the base of the inflatable body. FIG. 60A shows that the sensing elements 6001 can be disposed along two different latitudes of the inflatable body, and the coupling bus 6002 can run between the two latitudes, with other flexible interconnects 6004. FIG. 60B shows that the sensing elements 6001 can be disposed along two different latitudes of the inflatable body, and each latitude can have a respective coupling bus 6010 and 6012, with a different flexible interconnect running to each respective coupling bus 6010 or 6012.

Figure 61A:
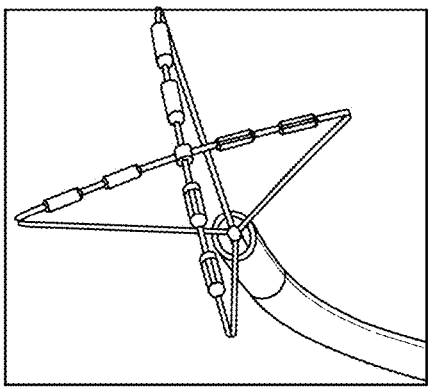
FIGS. 61A-61G illustrates examples of multi-electrode and balloon catheter devices, according to the principles described herein.
Figure 61B:
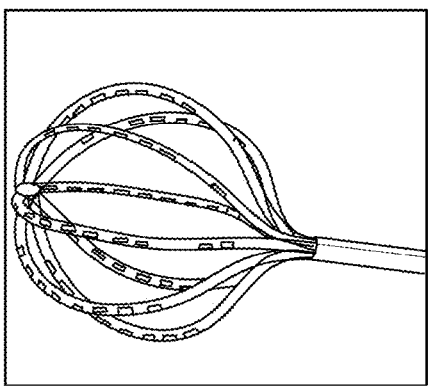
Figure 61C:
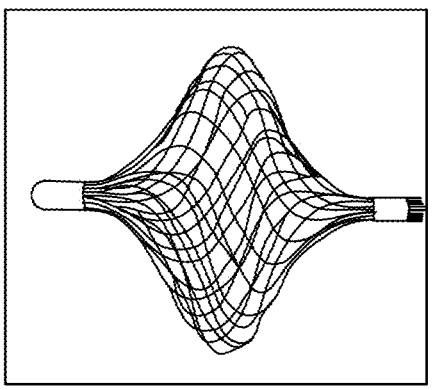
Figure 61D:
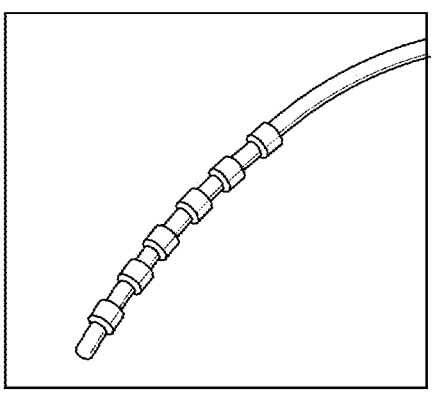
Figure 61E:
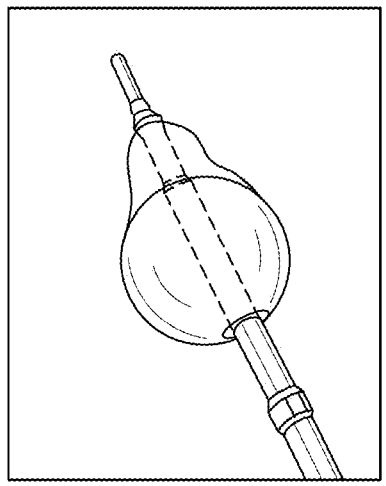
Figure 61F:
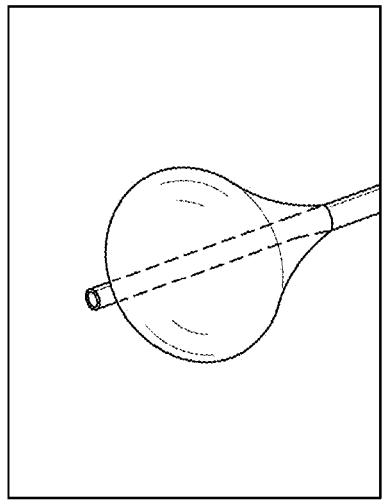
Figure 61G:
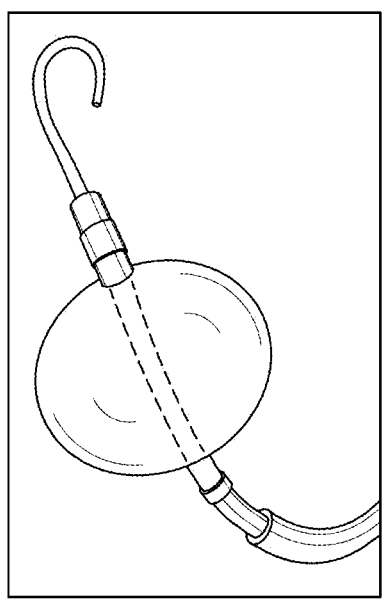

FIGS. 61A-61G illustrates examples of multi-sensing element (including multielectrode) devices and catheter devices. The devices in FIGS. 61A-61D include passive wires with polyimide-based encapsulation. The wires are exposed in select areas, thus forming electrode contacts. The electrode array can include, for example, 64 electrodes. FIGS. 61E-61G show the balloon-based ablation catheters that can be used to apply cryo-, laser-, and high intensity ultrasound—forms of therapy when deployed proximate to tissue. Any stretchable electronic system according to the principles described herein can be disposed on any of the catheters shown in FIGS. 61A-61G.

A configuration of stretchable electronic system according to the principles herein can be disposed on the surface of any of these example devises according to the principles herein. The description herein concerning determining the areas of minimal curvature of the inflatable body when in the deflated state can be applied to any of the example devices of FIGS. 61A-61G in going from a fully deployed state to a collapsed state (that has dimensions smaller than the fully deployed state), including the netting shape surface.

Examples disclosed herein provide the benefits of the multi-electrode configuration, and the advantages of balloon- and sheet-based platforms. High density mapping catheters are provided with deployable sheets. The sheets can include high-density electronics (>64 sensory nodes) along with multiplexing and amplification circuitry, which are embedded on a thin elastomeric or polymeric substrate. The substrate can have microfluidics channels that are intricately patterned with 10-100 μm channels used for delivering drugs, perfusates for cooling electronics or extremely cold or perfusates (alcohol, N2O etc) for cryoablation.

Figure 62:
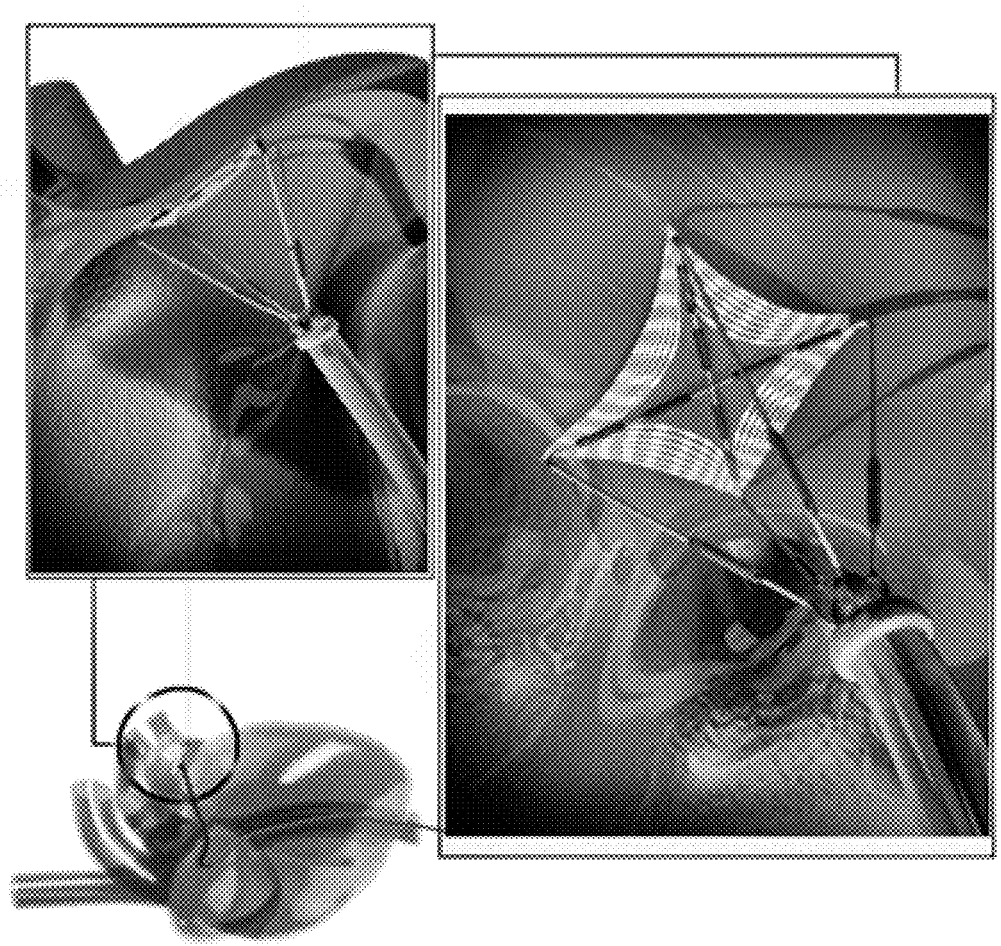
FIG. 62 illustrates example dense arrays of conformal electrodes with metal serpentine interconnects on thin polymeric sheets, according to the principles described herein.

FIG. 62 illustrates dense arrays of conformal electrodes with metal serpentine interconnects on thin polymeric sheets. The multi-electrode array design (each electrode ~100 μm$^2$ in surface area) allows for high-density spatial mapping of the interior surface of the heart. Electrodes are sub-micron (~0.5-1 μm) in thickness and can include onboard Si-based amplification circuits, row-select transistor-based transistor switches, along with other sensory structures, such as temperature and pressure sensors.

The example platform shown in FIG. 62 integrates a collection of sensors and is deployable with a nitinol cage design. The underlying substrates are thin (<100 μm) and can be made of bioabsorbable material such as silk. Silk can serve as a temporary support for the various epicardial examples disclosed herein.

Figure 63C:
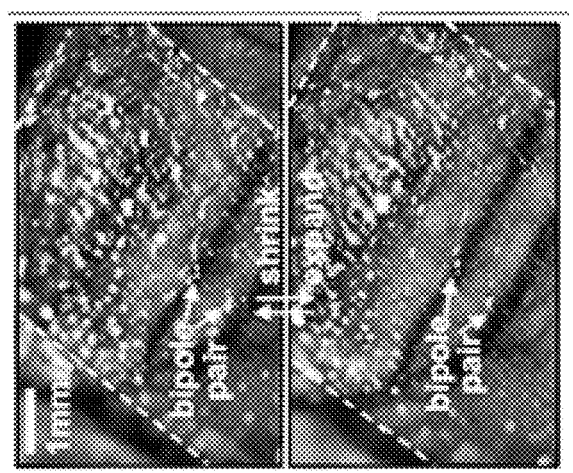
FIGS. 63A-63C illustrate example endocardial applications of the apparatus and methods, according to the principles described herein.
Figure 63B:
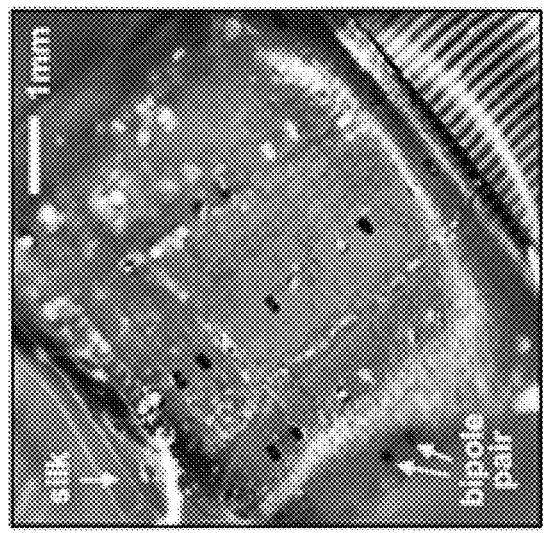
Figure 63A:
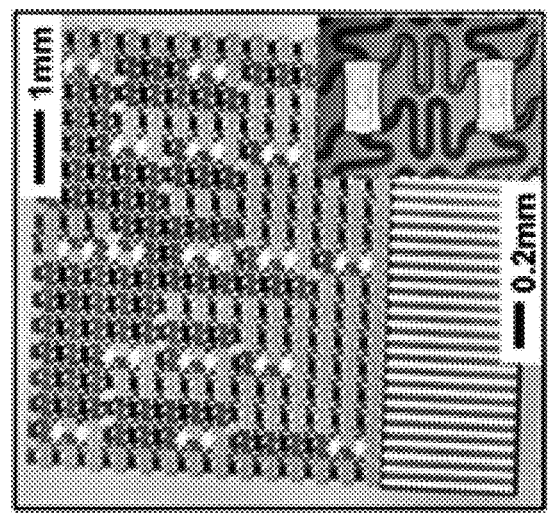

FIG. 63A-63C illustrate example endocardial applications of the apparatus and methods disclosed herein. FIG. 63A shows an image of array of electronics embedded on silk deployed on epicardial surface. FIG. 63B shows conformal/stretchable electronics capture electrical signals with broad areal coverage over 70-80% of the heart's anterior surface. FIG. 63C show how the system contracts and expands with dynamic contractions of the tissue (in this example, a live heart).

The EKG sensor array in FIG. 63A-63C include 16 electrodes. This density can be increased to thousands, for example, using the same demonstrated technology. The silk substrate dissolves within a few minutes enabling intimate mechanical coupling between the beating heart and the backside surface of the array of conformal electronics. For EKG and other sensing types, this physical coupling of devices to the surface of the heart can be beneficial. Another example that benefits from intimate physical contact is an array of lateral strain sensors that record multidirectional movements of the heart.

Figure 64C:
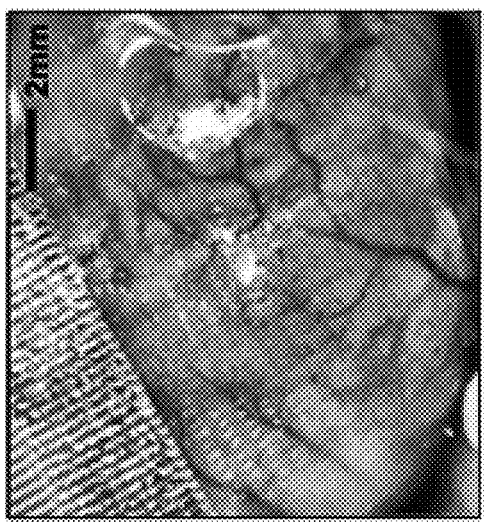
FIGS. 64A-64C show an example of an apparatus including strain sensors/gauges, according to the principles described herein.
Figure 64B:
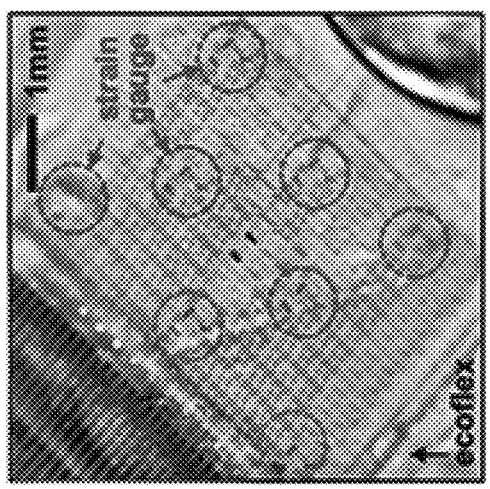
Figure 64A:
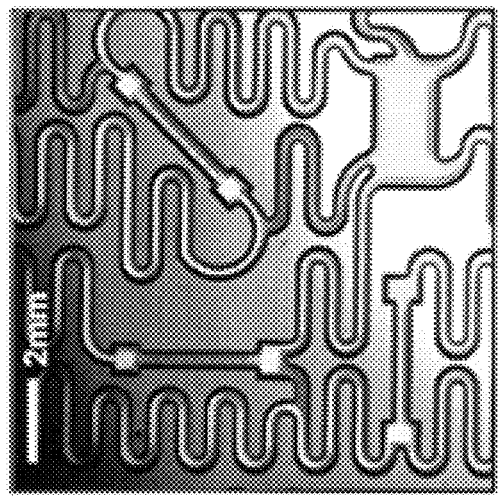

FIGS. 64A-64C show examples of such a system including strain sensors/gauges. Specifically, FIG. 64A shows strain gauges that implement stretchable silicon in an interconnected array, FIG. 64B shows an image of eight (8) groups of sensors on an ECOFLEX®. (BASF, Florham Park, N.J.) substrate. FIG. 64C shows an image of an array on the epicardial beating heart.

One capability of the lateral strain gauges is in monitoring rhythmic motions of the heart. The sensors can characterize multidirectional movements and sense heart rate increase, irregularities, or regions of the heart going through stress. Furthermore, the strain sensors can detect when the volume of the heart increases above its normal state, which can be an indication that the heart is suffering through myocardial infarct. This system can act as a 'cardiac sleeve' for implantable devices or can be deployed in the endocardium to sense when the device contacts the walls of the heart.

Figure 65C:
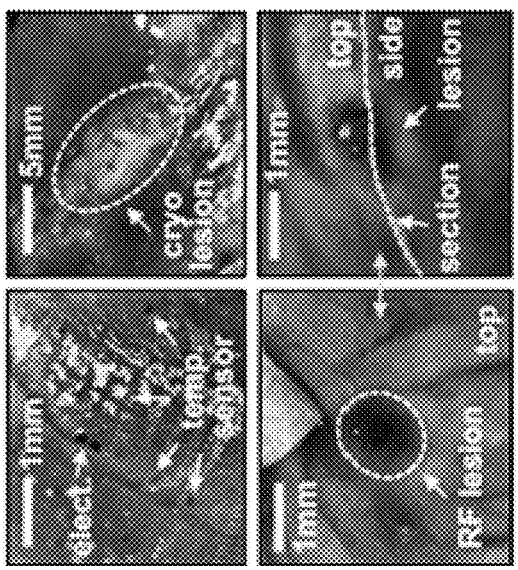
FIGS. 65A-65C illustrates example sensing modalities including temperature sensors, and RF components for wireless communications, according to the principles described herein.
Figure 65B:
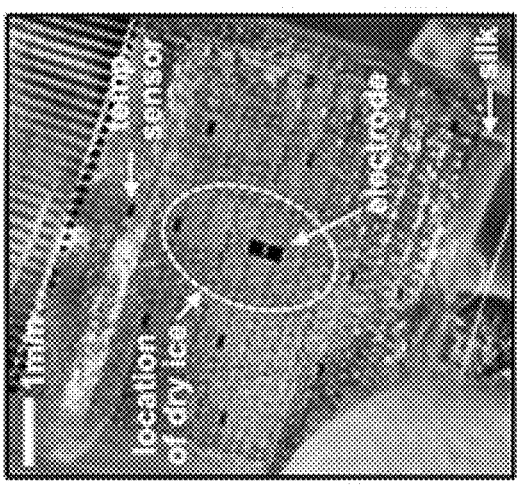
Figure 65A:
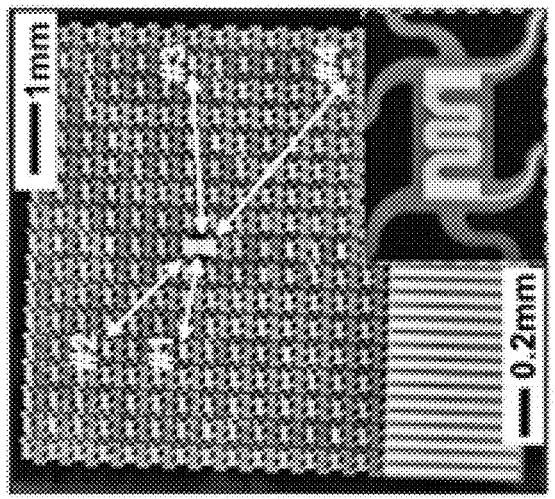

FIGS. 65A-65C show other example sensing modalities including temperature sensors, and RF components for wireless communications. FIG. 65A shows temperature sensor arrays co-located with sensing elements (including electrodes). The temperature sensors can be used to track low temperatures (to cryotemperatures) and high temperatures applied during RF ablation. FIG. 65B shows temperature sensor and electrode arrays on a silk substrate for a low-temperature measurement. FIG. 65C shows examples of applying the methods and apparatus with respect to cryo lesion and RF lesion.

In various examples disclosed herein, therapeutic apparatus are configured in the ways described herein to provide ablative therapy, which may comprise an element capable of emitting various forms of electromagnetic radiation including microwave energy, thermal energy, laser, or radio frequency (RF) electromagnetic (EM) radiation.

In other examples, the element comprises an ultrasound emitter for ultrasonic ablation. In such examples, the therapeutic facility (or element thereof) comprises an array of ultrasound transducers (e.g. piezoelectric crystals). Each island comprises a receiver that senses acoustic reflections generated by a source emitter that sends acoustic waves through the tissue at megahertz frequencies.

In still other examples, the device is configured to provide cryo-ablation. Further, by coupling delivery channels and micro-valves to the selectively operative circuitry in the manners described herein, cryo-ablation may be delivered by the therapeutic facility or selected portions thereof.

In ablative examples, the substrate may be stretchable as disclosed above and herein and provided with the stretchable circuitry described herein. Also as described herein, the stretchable circuitry is able to remain functional upon conforming to the surface of the tissue, which in examples for ablation, would comprise conformal contact with some surface of the heart or cardiovascular system, including the ostium of a pulmonary vein, any surface of a vein or artery, a septal wall of the heart, an atrial surface of a heart, or a ventricular surface of a heart.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While various inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described examples can be implemented in any of numerous ways. For example, some examples may be implemented using hardware, software or a combination thereof. When any aspect of an example is implemented at least in part in software, the software code can be executed on any suitable processor or collection of processors, whether provided in a single computer or distributed among multiple computers.

In this respect, various aspects may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various examples of the technology described above. The computer readable medium or media can be transportable, such that the program or programs stored thereon can be loaded onto one or more different computers or other processors to implement various aspects of the present technology as described above.

The terms "program" or "software" are used herein in a generic sense to refer to any type of computer code or set of computer-executable instructions that can be employed to program a computer or other processor to implement various aspects of the present technology as described above. Additionally, it should be appreciated that according to one aspect of this example, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various examples.

Also, the technology described herein may be embodied as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one example, to A only (optionally including elements other than B); in another example, to B only (optionally including elements other than A); in yet another example, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one example, to at least one, optionally including more than one, A, with no B present (and optionally including elements other than B); in another example, to at least one, optionally including more than one, B, with no A present (and optionally including elements other than A); in yet another example, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All examples that come within the spirit and scope of the following claims and equivalents thereto are claimed.

The invention claimed is:

1. An apparatus for medical diagnosis and/or treatment, the apparatus comprising:
a flexible substrate forming an inflatable body;
a coupling bus disposed along a latitude of and offset from the equator of the inflatable body;
a plurality of sensing elements disposed along at least one latitude of the inflatable body offset from the coupling bus, each sensing element comprising a pair of electrodes;
a plurality of stretchable interconnects, each stretchable interconnect electrically connecting a separate electrode of a separate sensing element of the plurality of sensing elements to the coupling bus; and
an intermediate bus disposed longitudinally about the inflatable body, the intermediate bus electrically connecting the coupling bus to a flexible printed circuit board.

2. The apparatus of claim 1, wherein the coupling bus comprises a plurality of serpentine interconnects, each coupling bus serpentine interconnect being electrically connected to a separate stretchable interconnect of the plurality of stretchable interconnects.

3. The apparatus of claim 1, further comprising an encapsulation material disposed over substantially a portion of the coupling bus.

4. The apparatus of claim 3, wherein the encapsulation material comprises polyurethane.

5. The apparatus of claim 2, further comprising:
a shaft coupled to the inflatable body,
wherein the flexible printed circuit board is disposed on the shaft, the intermediate bus comprises a plurality of serpentine interconnects, each intermediate bus serpentine interconnect being electrically connected to a separate coupling bus serpentine interconnect, and the plurality of sensing elements comprise at least one of a pressure sensor or an impedance sensor.

6. The apparatus of claim 5, wherein the shaft comprises a cryoablation device, a laser ablation device, a high intensity ultrasound or a RF device.

7. The apparatus of claim 1, wherein the sensing elements are disposed along portions of the inflatable body that experience minimal strain when the inflatable body is in a deflated state.

8. The apparatus of claim 1, wherein one or more of the sensing elements of the plurality of sensing elements comprises contact sensors.

9. The apparatus of claim 1, wherein each sensing element of the plurality of sensing elements is arranged on the flexible substrate in one of two annular rings.

10. The apparatus of claim 9, wherein sensing elements of the first annular ring are staggered on the inflatable body relative to sensing elements of the second annular ring.

11. The apparatus of claim 1, wherein the plurality of sensing elements are disposed in a helical pattern about the inflatable body.

12. The apparatus of claim 1, further comprising at least one encapsulation layer disposed over the plurality of sensing elements, wherein the encapsulation layer positions the sensing elements at a neutral mechanical plane.

13. The apparatus of claim 12, wherein the at least one encapsulation layer comprises a polymer.

14. The apparatus of claim 1, further comprising at least one intermediate layer disposed between the plurality of sensing elements and the inflatable body, wherein the at least one intermediate layer positions the sensing elements at a neutral mechanical plane.

15. The apparatus of claim 1, wherein the inflatable body is disposed near a distal end of a catheter.

16. The apparatus of claim 1, wherein the inflatable body is a balloon.

17. The apparatus of claim 16, wherein the balloon is cylindrical, onion-shaped, cone-shaped, dog-bone-shaped, or barrel-shaped.

18. The apparatus of claim 1, wherein the coupling bus has a T-configuration.

19. The apparatus of claim 1, further comprising an encapsulation material disposed over substantially a portion of the plurality of sensing elements.

20. The apparatus of claim 19, wherein the encapsulation material comprises polyurethane.

21. The apparatus of claim 1, wherein the sensing elements are formed from a conductive material.

22. The apparatus of claim 1, wherein the coupling bus is formed from a conductive material.

23. A method of performing a medical diagnosis and/or treatment on a tissue, the method comprising:
   disposing in proximity to the tissue an apparatus comprising:
      a flexible substrate forming an inflatable body;
      a coupling bus disposed along a latitude of and offset from the equator of the inflatable body;
      a plurality of sensing elements disposed along at least one latitude of the inflatable body offset from the coupling bus, each sensing element comprising a pair of electrodes;
      a plurality of stretchable interconnects, each stretchable interconnect electrically connecting a separate electrode of a separate sensing element of the plurality of sensing elements to the coupling bus; and
      an intermediate bus disposed longitudinally about the inflatable body, the intermediate bus electrically connecting the coupling bus to a flexible printed circuit board; and
   recording a measurement of at least one sensing element of the plurality of sensing elements, wherein the measurement provides an indication of a state of a portion of the tissue.

24. The method of claim 23, wherein the measurement provides an indication of a disease state of the portion of the tissue.

25. The method of claim 23, wherein the measurement provides an indication of a contact state of the portion of the tissue with the at least one sensing element of the plurality of sensing elements.

26. An apparatus for medical diagnosis and/or treatment, the apparatus comprising:
   a shaft;
   a flexible substrate forming an inflatable body disposed at a distal end of the shaft, a longitudinal axis of the inflatable body being aligned with the shaft;
   a coupling bus disposed along a latitude of the inflatable body;
   sensing elements disposed on the flexible substrate and electrically connected to the coupling bus, at least one of the sensing elements being arranged on the flexible substrate in a first one of two annular rings, and all remaining of the sensing elements on the flexible substrate being arranged in a second one of the two annular rings; and
   an intermediate bus disposed longitudinally about the inflatable body, the intermediate bus electrically connecting the coupling bus to a flexible printed circuit board,
   wherein at least one of the sensing elements located within the first one or the second one of the two annular rings is positioned on the flexible substrate to interface with an ostium of a lumen within which the apparatus is inserted, with the inflatable body in an inflated state.

27. The apparatus of claim 26, wherein each sensing element of a first of the two annular rings is about 7.5 mm from the distal pole of the inflatable body, and each sensing element of a second of the two annular rings is about 10 mm from the distal pole of the inflatable body.

28. The apparatus of claim 27, wherein the coupling bus forms an annular ring about 12 mm from the distal pole of the inflatable body.

29. The apparatus of claim 26, wherein the sensing elements of the first annular ring are staggered relative to the sensing elements of the second annular ring.

30. The apparatus of claim 26, further comprising:
   a plurality of wires connected to the flexible printed circuit board to provide and/or obtain electrical signals to the flexible printed circuit board,
   wherein the intermediate bus is electrically coupled to the flexible printed circuit board and to the sensing elements through the coupling bus, the sensing elements comprise at least one of a pressure sensor or an impedance sensor and are individually electrically connected to the flexible printed circuit board through the coupling bus and the intermediate bus, and the flexible printed circuit board is disposed over or inside the shaft.

31. The apparatus of claim 30, wherein the shaft comprises a cryoablation device, a laser ablation device, a high intensity ultrasound or a RF device.

32. The apparatus of claim 26, wherein the coupling bus is formed as an annular ring having a radius of about 12 mm from the distal pole of the inflatable body.

33. The apparatus of claim 32, wherein the coupling bus is a serpentine bus, and wherein the serpentine bus comprises a plurality of stretchable serpentine interconnects.

34. The apparatus of claim 26, wherein one or more of the sensing elements comprise contact sensors.

35. The apparatus of claim 26, wherein the coupling bus is disposed about an equator of the inflatable body.

36. The apparatus of claim 26, wherein the sensing elements are disposed in a helical pattern about the inflatable body relative to the longitudinal axis.

37. The apparatus of claim 26, wherein each sensing element includes a pair of electrodes, the apparatus further comprising:
   a plurality of stretchable interconnects, each stretchable interconnect electrically connecting a separate electrode of a separate sensing element of the sensing elements to the coupling bus.

38. The apparatus of claim 37, wherein the coupling bus comprises a plurality of serpentine interconnects, each coupling bus serpentine interconnect being electrically connected to a separate stretchable interconnect.

39. The apparatus of claim 26, further comprising at least one encapsulation layer disposed over the sensing elements, wherein the encapsulation layer positions the sensing elements at a neutral mechanical plane.

40. The apparatus of claim 26, further comprising at least one intermediate layer disposed between the sensing elements and the inflatable body, wherein the at least one intermediate layer positions the sensing elements at a neutral mechanical plane.

41. The apparatus of claim 26, wherein the inflatable body is a balloon.

42. The apparatus of claim 41, wherein the balloon is cylindrical, onion-shaped, cone-shaped, dog-bone-shaped, barrel-shaped.

43. The apparatus of claim 26, further comprising an encapsulation material disposed over substantially a portion of the sensing elements.

44. The apparatus of claim 43, wherein the encapsulation material comprises polyurethane.

45. The apparatus of claim 26, wherein the sensing elements are formed from a conductive material.

* * * * *